(12) United States Patent
Pikas et al.

(10) Patent No.: US 11,850,334 B2
(45) Date of Patent: Dec. 26, 2023

(54) IMMOBILISED BIOLOGICAL ENTITIES

(71) Applicant: CARMEDA AB, Upplands Väsby (SE)

(72) Inventors: Dagmar Pikas, Upplands Vasby (SE);
Johan Riesenfeld, Upplands Vasby (SE); Karin Leontein, Upplands Vasby (SE); Eva Koch, Upplands Vasby (SE); Stefan Oscarson, Belfield (IE)

(73) Assignee: Carmeda AB, Upplands Väsby (SE)

( * ) Notice: Subject to any disclaimer, the term of this patent is extended or adjusted under 35 U.S.C. 154(b) by 202 days.

(21) Appl. No.: 17/282,691

(22) PCT Filed: Oct. 3, 2019

(86) PCT No.: PCT/EP2019/076842
§ 371 (c)(1),
(2) Date: Apr. 2, 2021

(87) PCT Pub. No.: WO2020/070258
PCT Pub. Date: Apr. 9, 2020

(65) Prior Publication Data
US 2021/0379253 A1 Dec. 9, 2021

(30) Foreign Application Priority Data
Oct. 3, 2018 (EP) .................................. 18198421

(51) Int. Cl.
*A61L 33/00* (2006.01)
*A61L 33/06* (2006.01)
*C08L 5/10* (2006.01)

(52) U.S. Cl.
CPC ......... *A61L 33/0023* (2013.01); *A61L 33/062* (2013.01); *C08L 5/10* (2013.01); *A61L 2300/236* (2013.01); *A61L 2300/42* (2013.01)

(58) Field of Classification Search
CPC ............... A61L 33/0023; A61L 33/062; A61L 2300/236; A61L 2300/42; C08L 5/10
See application file for complete search history.

(56) References Cited

U.S. PATENT DOCUMENTS

| 4,613,665 A | 9/1986 | Olle |
| 6,461,665 B1 | 10/2002 | Scholander |
| 6,653,457 B1 | 11/2003 | Larm et al. |
| 2008/0089919 A1 | 4/2008 | Cleek et al. |

FOREIGN PATENT DOCUMENTS

| EP | 0086186 A1 | 8/1983 |
| EP | 0086187 B1 | 10/1985 |
| EP | 0495820 B1 | 5/1995 |
| WO | 91/15252 A1 | 10/1991 |
| WO | 2010/029189 A2 | 3/2010 |
| WO | 2011/110684 A1 | 9/2011 |
| WO | 2012/123384 A1 | 9/2012 |
| WO | 2020/070258 A1 | 4/2020 |

OTHER PUBLICATIONS

Walenga et al., "Development of a Synthetic Heparin Pentasaccharide: Fondaparinux", Turk J Haematol, 19(2), (2002), pp. 137-150.*
Bitter et al., "A Modified Uronic Acid Carbazole Reaction," Anal. Biochem., 4:330-334 (1962).
Farris et al., "Charge Density Quantification of Polyelectrolyte Polysaccharides by Conductometric Titration: An Analytical Chemistry Experiment," J. Chem. Educ., 89(1):121-124 (2012).
International Search Report and Written Opinion received for PCT Patent Application No. PCT/EP2019/076842, dated Dec. 18, 2019, 8 pages.
Lane et al., "Anticoagulant activities of heparin oligosaccharides and their neutralization by platelet factor 4," Biochem. J., 218:725-732 (1984).
Larsen et al., "Assay of plasmaheparin using thrombin and the chromogenic substrate H-D-Phe-Pip-Arg-pNA," (S-2238) Thromb. Res., 13:285-288 (1978).
Pasche et al., "A binding of antithrombin to immobilized heparin under varying flow conditions," Artif. Organs, 15:281-491 (1991).
Petitou et al., "1976-1983, a critical period in the history of heparin: the discovery of the antithrombin binding site," Biochimie, 85(1-2):83-89 (2003).
Petitou et al., "A Synthetic Antithrombin III Binding Pentasaccharide Is Now a Drug! What Comes Next?," Angew. Chem. Int. Ed., 43:3118-3133 (2004).
Pozsgay, "Synthesis of Glycoconjugate Vaccines against Shigella dysenteriae Type 1," J. Org. Chem., 63(17):5983-5999 (1998).
Smith et al., Quantitation of Glycosaminoglycan Hexosamine Using 3-Methyl-2-Benzothiazolone Hydrazone Hydrochloride, Anal. Biochem., 98:478-480 (1979).
Thunberg et al., "The Molecular Size Of The Antithrombin-Binding Sequence In Heparin," FEBS Letters, 117:203-206 (1980).
Hirsh et al., "Guide to Anticoagulant Therapy: Heparin A Statement for Healthcare Professionals From the American Heart Association", Circulation, vol. 103, No. 24, 2001, pp. 2994-3018.

* cited by examiner

*Primary Examiner* — Patrick D Niland

(57) ABSTRACT

There is provided inter alia an anticoagulant surface which surface has covalently bound thereto a plurality of fragments of heparin, wherein said fragments consist of 5-18 saccharide units and at least some of said plurality of fragments comprise polysaccharide sequence A, which surface catalyses the inhibition of FIIa and FXa by AT.

32 Claims, 9 Drawing Sheets

Fondaparinux

IMMOBILISED BIOLOGICAL ENTITIES

CROSS-REFERENCE TO RELATED APPLICATIONS

This application is a national phase application of PCT Application No. PCT/EP2019/076842, internationally filed on Oct. 3, 2019, which claims priority to EP Application No. 18198421.2, filed Oct. 3, 2018, which is herein incorporated by reference in its entirety for all purposes.

FIELD OF THE INVENTION

The present invention relates to surfaces having covalently bound thereto a plurality of fragments of heparin, solid objects comprising such surfaces and to processes for preparing such surfaces. In particular, the present invention relates to surfaces having covalently bound thereto a plurality of fragments of heparin, wherein said surfaces catalyse the inhibition of FIIa and FXa by AT.

BACKGROUND OF THE INVENTION

When a medical device is implanted in the body or is in contact with body fluids, a number of different reactions are set into motion, some of them resulting in inflammation and some in the coagulation of the blood in contact with the device surface. In order to counteract these serious adverse effects, the well-known anticoagulant compound heparin has for a long time been administered systemically to patients before the medical device is implanted into their body, or when it is in contact with their body fluids, in order to provide an antithrombotic effect.

One of the most successful processes for rendering a medical device non-thrombogenic has been the covalent binding of a heparin to a modified surface of the device. The general method and improvements thereof are described in European patents: EP-B-0086186, EP-B-0086187, EP-B-0495820 and U.S. Pat. No. 6,461,665 (herein incorporated by reference).

These patents describe the preparation of surface modified substrates by first, a selective cleavage of the heparin polysaccharide chain, e.g. using nitrous acid degradation, leading to the formation of terminal aldehyde groups. Secondly, the introduction of one or more surface modifying layers carrying primary amino groups on the surface of the medical device, and thereafter reacting the aldehyde groups on the polysaccharide chain with the amino groups on the surface modifying layers followed by a reduction of the intermediate Schiff's bases to form stable secondary amine bonds.

Factor IIa ("FIIa", also known as thrombin) and Factor Xa ("FXa") are two of several coagulation factors, all of which work together to result in the formation of thrombi at a surface in contact with the blood. Antithrombin (also known as antithrombin III, "ATIII" or "AT") is the most prominent endogenous coagulation inhibitor. It neutralizes the action of FIIa, FXa and other coagulation factors and thus restricts or limits blood coagulation. The capacity of heparin to catalyse the inhibition of activated coagulation factors such as FIIa and FXa by antithrombin (AT) is dependent on a specific pentasaccharide structure, depicted in FIG. 1, called the active sequence (also referred to herein as the "active pentasaccharide sequence" or "pentasaccharide sequence A"). AT binds to the active sequence of heparin, resulting in a conformational change of AT, which accelerates the inhibition of the coagulation factors. The heparin-catalysed inhibitory mechanism does however differ between FIIa and FXa. The inhibition of FXa by AT is catalysed by heparin fragments, containing the active sequence, of the size of a pentasaccharide (5 sugar units) or larger. However, the mechanism for inhibition of FIIa requires heparin fragments of a minimum size of 18 sugar units to achieve detectable inhibition (Lane D. A. et al, Biochem J (1984) 218, 725-732), because AT and FIIa are required to bind to the same heparin chain in a ternary bridging complex (Petitou, M. and van Boeckel C. A. A., Angew. Chem. Int. Ed. 2004, 43, 3118-3133). However, the level of inhibition achieved by fragments of 18 sugar units is still very low. To achieve substantial inhibition of FIIa, then fragments must contain more than 18 sugar units. Thus, the prior art teaches that heparin fragments containing the active sequence, but comprising no more than 18 saccharide units, have inhibitory capacity towards FXa, but low or absent inhibitory capacity towards FIIa.

WO 91/15252 discloses the incorporation of oligosaccharides derived from heparin into the backbone of a polymer, wherein the polymer may then be applied to a surface. This approach is distinct from that of the present invention, wherein heparin fragments are covalently bonded or grafted on to a surface.

SUMMARY OF THE INVENTION

The present inventors have surprisingly found that fragments of heparin, devoid of the capacity to catalyse the inhibition of FIIa by AT in solution, are capable of catalysing this same reaction when they are immobilized to a surface. The immobilized fragments are organized in a way which may allow them to act synergistically, to accomplish that which requires substantially longer molecules in solution.

According to one aspect of the invention, there is provided an anticoagulant surface which surface has covalently bound thereto a plurality of fragments of heparin, wherein said fragments consist of 5-18 saccharide units and at least some of said plurality of fragments comprise polysaccharide sequence A:

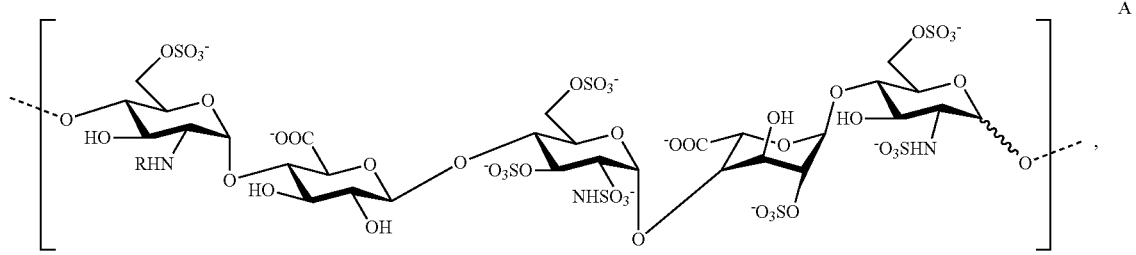

wherein R=Ac or SO₃-
which surface catalyses the inhibition of FIIa and FXa by AT (hereinafter "a surface according to the invention" or "a surface of the present invention").

Surfaces of the present invention may, in at least some embodiments, have one or more of the following advantages.
 (i) Inhibition of FIIa;
 (ii) Inhibition of FXa;
 (iii) Increased anticoagulant activity of heparin fragments when immobilized;
 (iv) Increased ease of production;
 (v) Increased suitability for coating a solid object;
 (vi) Increased suitability for implantation;
 (vii) Increased stability;
 (viii) Utilisation of fragments of heparin;
 (ix) Utilisation of non-animal derived material;
 (x) Increased biocompatibility, e.g. blood compatibility;
 (xi) Increased blood contact performance.

Furthermore, at least some of the embodiments of the present invention may have one or more of the following advantages.
 (a) Heparin fragments of a synthetically feasible size i.e. below 18 sugar units, can be utilized in a FIIa- and FXa-inhibitory coating;
 (b) An anticoagulant coating that inhibits both FIIa and FXa can be obtained from non-animal derived heparin fragments;
 (c) A coating with enhanced inhibitory activity towards FIIa can be obtained;
 (d) Immobilized heparin fragments from a synthetic source can produce a coating with a more defined mechanism of action or more predictable activity, by controlling and accurately quantifying the amount of polysaccharide sequence A present
 (e) A coating with high anticoagulant entity activity such as heparin activity can be obtained e.g. as determined using Evaluation Method J;
 (f) An anticoagulant coating which does not leach heparin fragments, due to its covalent attachment, and therefore remains active for a long period may be obtained;
 (g) A coating of heparin fragments having uniform distribution and being comparatively smooth can be obtained e.g. as determined using Evaluation Method I.

DETAILED DESCRIPTION OF THE INVENTION

Heparin and Fragments Thereof

Figure 1:
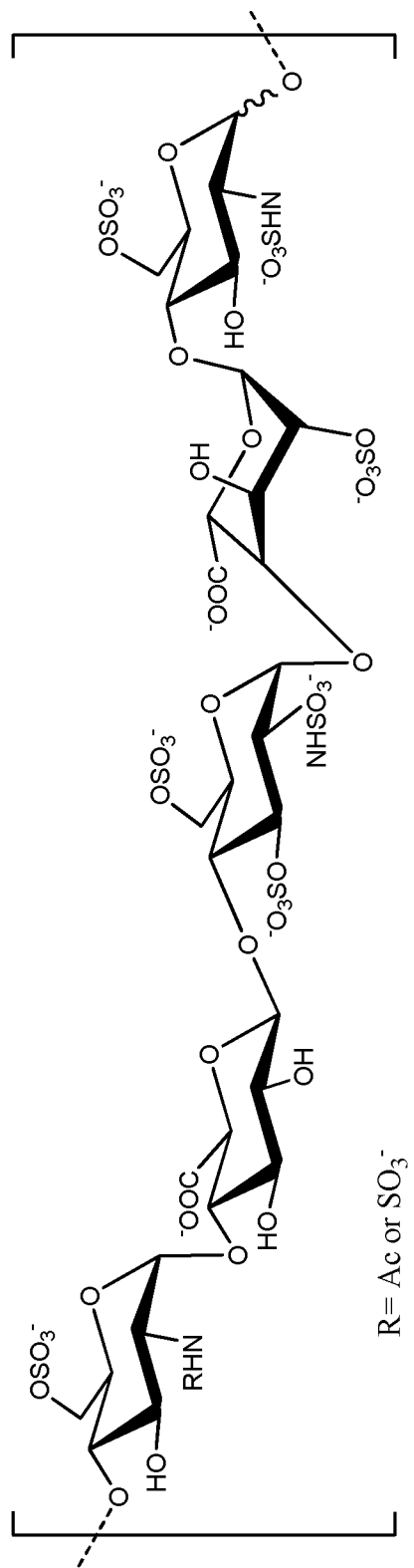
FIG. 1: The active sequence (A) of heparin
Figure 2:
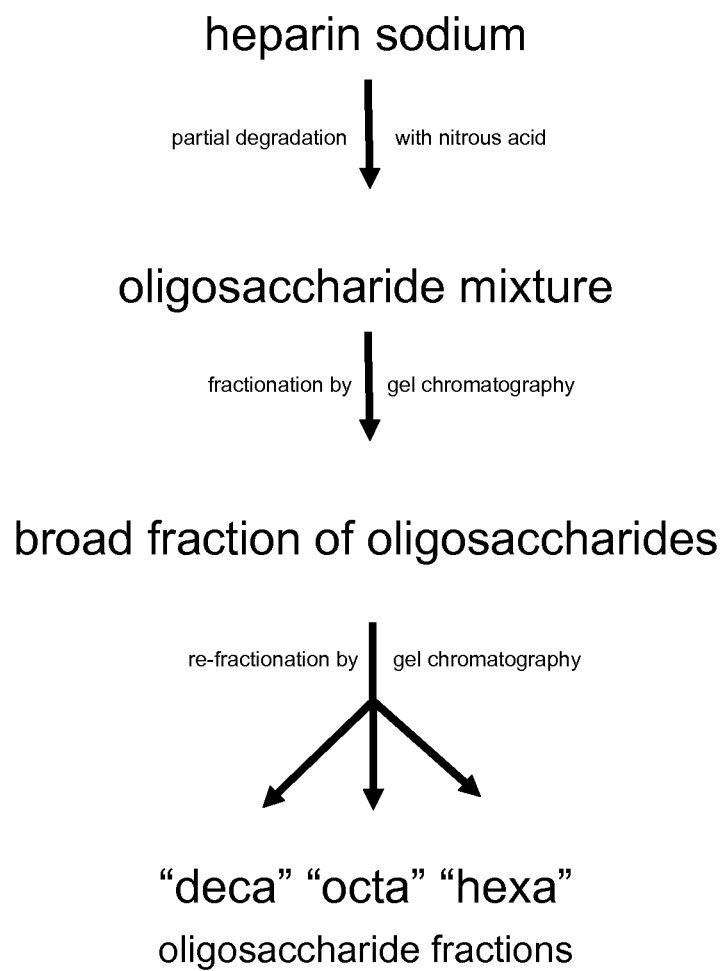
FIG. 2: Schematic illustration of the preparation of oligosaccharide fractions from heparin sodium
Figure 3:
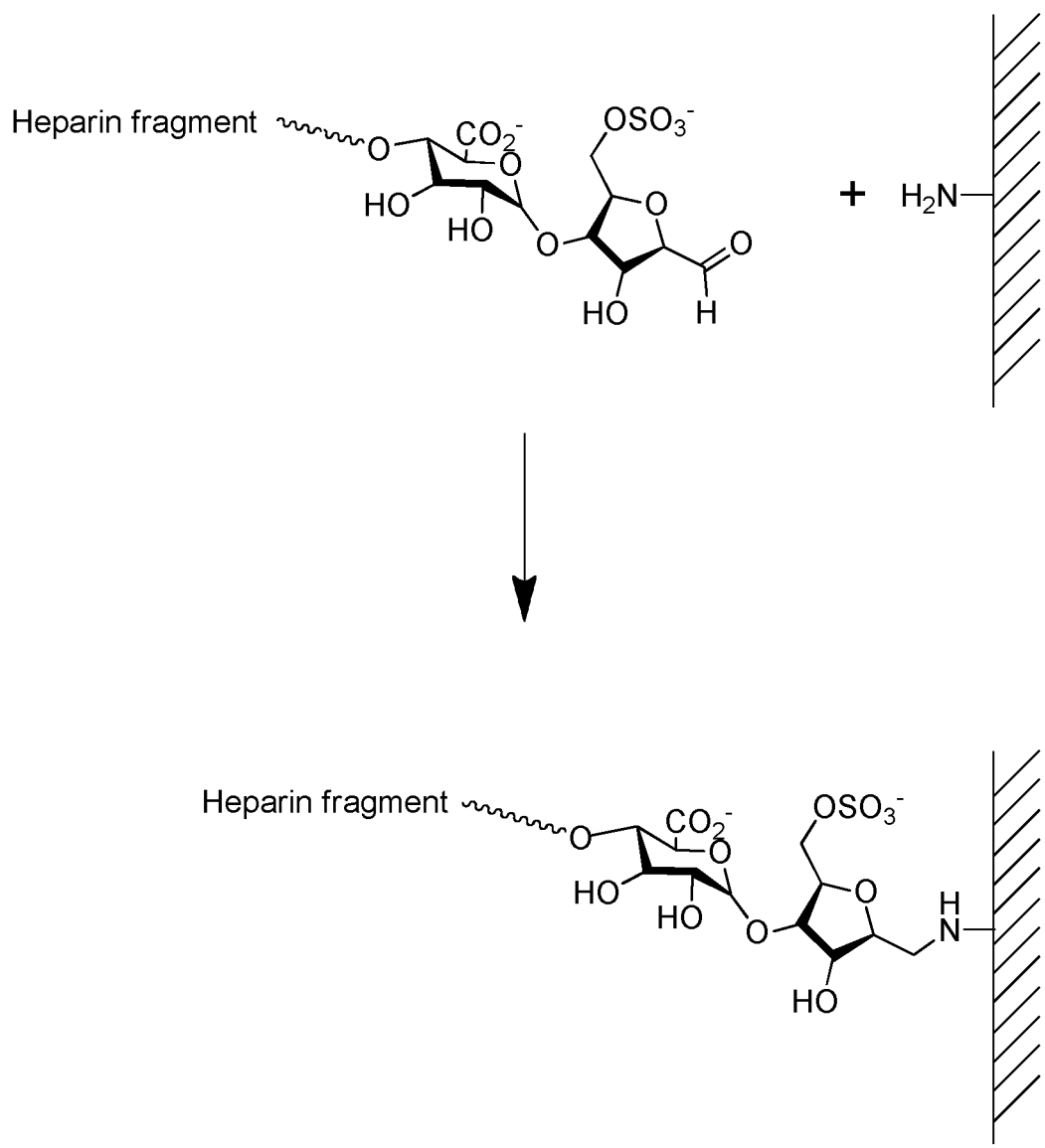
FIG. 3: Fragment of heparin derived from nitrous acid degradation, being immobilized to a surface

Heparin is a member of the glycosaminoglycan family of carbohydrates and consists of a variably sulfated repeating disaccharide unit. Heparin and fragments thereof are built up from alternating hexuronic acid and D-glucosamine units. The hexuronic acid units consist of D-glucuronic acid and L-iduronic acid. These are respectively beta- and alpha-(1,4)-bound to the glucosamine units. A large proportion of the L-iduronic acid residues are O-sulfated in the 2-position. The D-glucosamine units are N-sulfated, O-sulfated in the 6-position and are alpha-(1,4)-bound to the hexuronic acid residues. Certain D-glucosamine units are also O-sulfated in the 3-position. The anticoagulant activity of heparin is mainly dependent on an AT binding sequence, FIG. 1, which is present in only about one-third of the heparin chains constituting the heparin utilized in clinic.

Fragments of heparin may be derived from full length heparin (native heparin) or any variant of heparin. Particularly suitable variants of heparin from which fragments may be derived include an alkali metal or alkaline earth metal salt of heparin (e.g. sodium heparin (e.g. Hepsal or Pularin), potassium heparin (e.g. Clarin), lithium heparin, calcium heparin (e.g. Calciparine) or magnesium heparin (e.g. Cutheparine)), a low molecular weight heparin (e.g. ardeparin sodium, tinzaparin or dalteparin), heparan sulfate, a heparinoid, a heparin-based compound, heparin having a hydrophobic counter-ion, a synthetic heparin composition capable of antithrombin-mediated inhibition of FXa, a synthetic heparin derivative comprising at least the active pentasaccharide sequence from heparin (see for example Petitou et al., Biochimie, 2003, 85(1-2):83-9), heparin modified by means of e.g. mild nitrous acid degradation (U.S. Pat. No. 4,613,665A, incorporated herein by reference in its entirety) or periodate oxidation (U.S. Pat. No. 6,653,457B1, incorporated herein by reference in its entirety).

In some embodiments all of the fragments of heparin contain the active pentsaccharide sequence. In other embodiments only a fraction of the fragments of heparin contain the active pentasaccharide sequence. In the case of heparin fragments produced by fragmentation methods, relatively low proportions of the active pentasaccharide sequence may be present.

Suitably at least 1%, more suitably at least 5%, more suitably at least 10%, more suitably at least 15%, more suitably at least 20%, more suitably at least 30% of the fragments of heparin contain the active pentasaccharide sequence. In the case of heparin fragments produced by synthetic means, higher proportions of the active pentasaccharide sequence may be present. Suitably at least 60%, more suitably at least 70%, more suitably at least 80%, more suitably at least 90%, more suitably at least 95%, more suitably at least 99% of the fragments of heparin contain the active pentasaccharide sequence.

In such embodiments, the concentration of fragments containing the active sequence may be increased by, for example, purification with AT binding affinity columns.

In some embodiments, the fragments of heparin are homogenous in structure (i.e. the fragments of heparin are substantially identical, more suitably identical) and all comprise polysaccharide sequence A. In other embodiments the fragments of heparin are heterogeneous in structure (i.e. the fragments of heparin are comprised within a mixture wherein the mixture comprises at least two different fragments of heparin). If the fragments of heparin are heterogenous in structure, in one embodiment only a fraction of the fragments of heparin contain the active pentasaccharide sequence, as described above. In a more suitable embodiment, the fragments of heparin are heterogenous in structure and all contain polysaccharide sequence A.

The fragments of heparin may be produced using techniques known in the art. Suitably the fragments are fragments of native heparin produced by a process comprising degrading (e.g. fragmentation of) native heparin. As illustrated in the examples below, fragments of heparin may be prepared by partial nitrous acid cleavage of native heparin, optionally followed by fractionation by gel chromatography.

Alternatively, the fragments of heparin may be synthetically produced. Synthetic production may be achieved by chemo enzymatic or organic chemistry methods, such as those detailed in the Examples.

According to the invention the fragments consist of 5-18 saccharide units. Suitably the fragments consist of at least 6 saccharide units, more suitably at least 7, more suitably at least 8 saccharide units. Suitably the fragments consist of no more than 17 saccharide units, more suitably no more than 16 saccharide units, more suitably no more than 15 saccharide units, more suitably no more than 14 saccharide units, more suitably no more than 13 saccharide units, more suitably no more than 12 saccharide units, more suitably no more than 11 saccharide units, more suitably no more than 10 saccharide units, more suitably no more than 9 saccharide units, more suitably no more than 8 saccharide units. In an embodiment the fragments consist of 5 saccharide units. In an embodiment, the fragments consist of 5-18 e.g. 5-17 e.g. 5-16 e.g. 5-15 e.g. 5-10 e.g. 5-8 saccharide units. In another embodiment, the fragments consist of 6-18 e.g. 6-17 e.g. 6-16 e.g. 6-15 e.g. 6-10 e.g. 6-8 saccharide units.

Fragments of heparin may be produced by nitrous acid cleavage. In practice an octasaccharide is the shortest fragment that can contain a functional active sequence, when produced by nitrous acid cleavage (Thunberg L. et al, FEBS Letters 117 (1980), 203-206), since the degradation by diazotization to form a free terminal aldehyde group are consuming one of four D-glucosamine unit. The remaining D-glucosamine will, if they have the right sulfatation pattern, be part of the active AT-binding sequence, see FIG. 1. In practice only a few of the octasaccharide fragment will contain the active sequence, since the major part of the heparin from which it is made, are devoid of the active sequence.

Immobilization of Heparin Fragments

The fragments of heparin may be covalently bound to the surface using techniques known in the art. As illustrated in the examples below, fragments of heparin may for example be bound to a surface having an outermost layer of polyamine via reductive amination (see e.g. Larm et al in EP0086186A1 and EP0495820B1). The fragments of heparin are covalently bound to a surface, therefore the fragments of heparin do not substantially elute or leach from the surface.

Suitably the fragments of heparin are single-point attached, more suitably end-point attached. More suitably the fragments of heparin are covalently bound to the surface via their reducing end and more suitably the fragments of heparin are covalently bound to the surface via position C1 of their reducing end, see FIG. 6. The advantage of end-point attachment, especially reducing end-point attachment, is that the biological activity of the fragments of heparin is maximized due to enhanced availability of the antithrombin interaction sites as compared with attachment elsewhere in the fragments of heparin.

A representative end-point attachment process is described in EP0086186B1 (Larm; incorporated herein by reference in its entirety) which discloses a process for the covalent binding of oligomeric or polymeric organic substances to substrates of different types containing primary amino groups. The substance to be coupled, which may be heparin, is subjected to degradation by diazotization to form a substance fragment having a free terminal aldehyde group. The substance fragment is then reacted through its aldehyde group with the amino group of the substrate to form a Schiff's base, which is then converted (via reduction) to a secondary amine.

WO 91/15252 discloses the incorporation of oligosaccharides derived from heparin into the backbone of a polymer, wherein the polymer may then be applied to a surface. This approach is distinct from that of the present invention, wherein heparin fragments are covalently bonded or grafted on to a surface (see page 5, paragraph 2 of WO 91/15252).

Suitably a surface of the invention comprises pendant functional groups to which the fragments of heparin are covalently bound. Suitably the fragments of heparin are covalently bound or grafted to the surface (suitably via a modified reducing terminal residue).

Suitably the fragments of heparin are not incorporated into the surface. Suitably the fragments of heparin are not incorporated into a polymeric backbone (particularly a polymeric backbone comprising acrylamide). Suitably the surface does not comprise a copolymer (particularly a copolymer comprising fragments of heparin, more particularly a copolymer comprising fragments of heparin and acrylamide). Suitably a surface of the invention is not produced by incorporation of fragments of heparin into a polymeric backbone. Suitably the surface is not a polymer as disclosed in WO 91/15252.

The antithrombogenic properties of the surface of the invention may be enhanced with increased heparin fragment density. In particular, inhibition of FIIa (e.g. determined by Evaluation Method H) may be enhanced by increased heparin density. Accordingly, suitably a surface according to the invention has heparin fragment concentration of at least 1 µg/cm$^2$, e.g. at least 2 µg/cm$^2$, at least 4 µg/cm$^2$, at least 5 µg/cm$^2$, or at least 6 µg/cm$^2$, suitably measured according to Evaluation Method H.

In one embodiment there is provided a method of making an anticoagulant surface comprising covalently binding to a surface a plurality of fragments of heparin, wherein said fragments consist of 5-18 saccharide units and at least some of said plurality of fragments comprise polysaccharide sequence A:

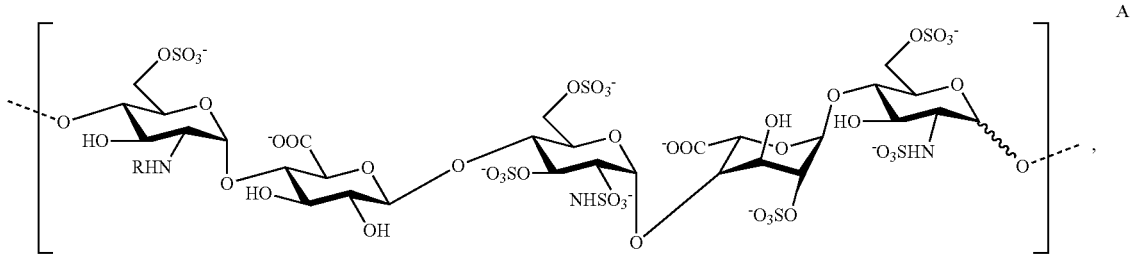

wherein R=Ac or SO$_3^-$
which surface catalyses the inhibition of FIIa and FXa.

Suitably the surface is a solid surface.

In one embodiment there is provided an anticoagulant surface obtainable by covalently binding to a surface a plurality of fragments of heparin, wherein said fragments consist of 5-18 saccharide units and at least some of said plurality of fragments comprise polysaccharide sequence A:

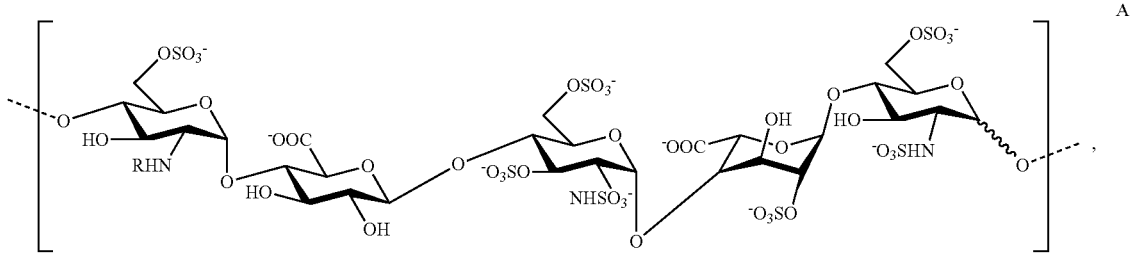

wherein R=Ac or SO$_3^-$
which surface catalyses the inhibition of FIIa and FXa by AT.

Suitably the surface is a solid surface.

Linkers and Spacers
Linkers

In one embodiment the fragments of heparin may be covalently bound to the surface via a linker. The linker facilitates covalent binding of the fragments of heparin to the surface.

Suitably the linker does not interfere with the heparin activity of the heparin fragments (i.e. AT binding).

In one embodiment the linker consists of an alkylene chain which is optionally substituted and in which one or more carbon atoms of the chain may be replaced by heteroatoms selected from oxygen, sulphur and nitrogen. In one embodiment the linker consists of atoms selected from hydrogen, oxygen, carbon, sulphur and nitrogen. In one embodiment the linker consists of a branched or unbranched C$_{1-15}$ alkylene chain, wherein optionally one or more carbons (for example 1, 2 or 3 carbons, suitably 1 or 2, in particular 1) is/are replaced by a heteroatom selected from O, N or S, especially O or N, wherein said chain is optionally substituted by one or more groups (for example 1 to 3, such as 2 groups) independently selected from oxo, halogen, an aryl group, a heteroaryl group, a carbocyclyl group or a heterocyclyl group. Alkylene as used herein refers to straight chain or branched chain alkylene, such as, without limitation, methylene, ethylene, propylene, iso-propylene, butylene, and tert-butylene. In one embodiment alkylene refers to straight chain alkylene.

As used herein "alkylene chain" means a saturated chain of carbon atoms which has two points of attachment to other groups. Thus, for example, ethylene means the moiety —CH$_2$CH$_2$—.

In one embodiment, the linker comprises a secondary amine. A representative procedure for covalently bonding a heparin moiety to a polymer via a secondary amine is described in EP0086186B1 (incorporated herein by reference in its entirety).

In one embodiment, the linker comprises a secondary amide. Thus, a further representative procedure for covalently bonding a heparin moiety to a surface via an amidation reaction involving N-succinimidyl 3-(2-pyridyldithio) propionate (SPDP) or 1-ethyl-3-(3-dimethylaminopropyl)-carbodiimide (EDC) is set out in WO2012/123384A1 (incorporated herein by reference in its entirety). The same procedures may be applied to fragments of heparin.

In one embodiment, the linker comprises a 1,2,3-triazole. A representative procedure for covalently bonding a heparin moiety to a polymer via a 1,2,3-triazole linkage is described in WO2010/029189A2 (Carmeda AB, incorporated herein by reference in its entirety). The same procedure may be applied to heparin fragments. The document describes the azide- or alkyne-functionalization of a polyimine, the preparation of alkyne- and azide-functionalized heparin (both native and nitrous acid degraded heparin); and reactions to link the derivatised heparin to the derivatised polymer via a 1,2,3-triazole linker.

In one embodiment, the linker comprises a thioether. A representative procedure for covalently bonding a heparin moiety to a polymer via a thioether linkage is described in WO2011/110684A1 (Carmeda A B et al., incorporated herein by reference in its entirety). The same procedure may be applied to heparin fragments.

In one embodiment, the plurality of fragments of heparin are not covalently bound to the surface via a thioether nor a 1,2,3-triazole. In one embodiment, the plurality of fragments of heparin are not covalently bound to the surface via a linker comprising a thioether nor a linker comprising a 1,2,3-triazole.

The linker can be attached to the reducing or to the non-reducing end of the heparin fragments, suitably the reducing end. Suitably the linkers are single-point attached, more suitably end-point attached to the heparin fragments. More suitably the linkers are bound to the heparin fragments via the reducing end of the heparin fragments and more suitably the linkers are bound to the heparin fragments via position C1 of the reducing end of the heparin fragments. In such embodiments the linker may suitably be incorporated during the synthesis of the heparin fragments. In such embodiments the linker structure and point of attachment to the heparin fragment will be compatible with the reaction conditions utilized in the synthesis.

In one embodiment the linker has a molecular weight of 14 to 200, suitably 14 to 100 Da. In one embodiment the linker has a length of 10 to $10^3$ Å, more suitably 20 to $10^2$ Å, more suitably 30 to 100 Å. In one embodiment the linker consists of 3 to 50 atoms, suitably 6 to 36 atoms, suitably 9 to 30 atoms, suitably 12 to 22 atoms, suitably about 19 atoms.

In one embodiment the fragments of heparin are covalently bound to the surface via a linker and the linker comprises formula (I)

$$(CH_2)_n NHCO(CH_2)_m \qquad (I)$$

wherein n is 1 to 20 and m is 1 to 20.

More suitably n is 2 to 15, more suitably 3 to 9, more suitably 4 to 6, more suitably 5. Suitably m is 2 to 10, more suitably 3 to 5, more suitably 4.

Table 1 below provides examples of linkers suitable for attaching the fragments of heparin to the surface along with the functional groups from which the covalent linker is formed and the type of reaction used. See e.g. reference (ISBN: 978-0-12-370501-3, Bioconjugate techniques, 2nd ed. 2008, herein incorporated by reference in its entirety). However, radical coupling reactions may also be contemplated.

TABLE 1

Exemplary linkers

| Type of reaction | Func. group 1 | Func. group 2 | Linker |
|---|---|---|---|
| Reductive amination | *–CH$_2$–NH$_2$ | *–C(=O)–H | *–CH$_2$–NH–CH$_2$–* |
| Amidation | *–CH$_2$–NH$_2$ | *–C(=O)–OH | *–CH$_2$–NH–C(=O)–CH$_2$–* |
| Michael addition | *–CH$_2$–NH$_2$ | *–C(=O)–C(=CH$_2$)–* | *–CH$_2$–NH–CH$_2$–CH(*)–C(=O)–* |
| Michael addition | *–CH$_2$–SH | *–C(=O)–CH=CH–* | *–CH$_2$–S–CH(*)–C(=O)–* |
| Thiol-Ene Click | *–CH$_2$–SH | *–CH=CH$_2$ | *–CH$_2$–S–CH$_2$–CH$_2$–* |
| Thio-Bromo | *–CH$_2$–SH | *–CH$_2$–Br | *–CH$_2$–S–CH$_2$–* |
| Thiol-Yne Click | *–CH$_2$–SH | *–C≡CH | *–CH$_2$–S–CH(–S–CH$_2$–*)–* |
| CuAAC Click | *–CH$_2$–N$_3$ | *–C≡CH | *–triazole–CH$_2$–* |
| Amidation (NHS-activated) | *–CH$_2$–NH$_2$ | *–CH$_2$–C(=O)–O–NHS | *–CH$_2$–NH–C(=O)–CH$_2$–* |

TABLE 1-continued

Exemplary linkers

| Type of reaction | Func. group 1 | Func. group 2 | Linker |
|---|---|---|---|
| Amidation/ Disulfide (SPDP) | 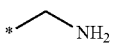 | 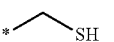 | 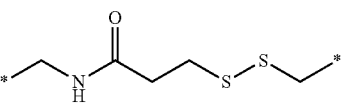 [SMILES: *CNC(=O)CCSSC*] |

For each linker, one of the functional end groups is on the surface and the other is on the heparin fragment. In principle, either way round is possible i.e. by reference to Table 1, functional groups 1 and 2 may respectively be on the surface and on the heparin fragment or may respectively be on the heparin fragment and on the surface.

Illustrative chemistries are discussed below:

—C—NH—C— Linkage

Reductive amination: A reductive amination, also known as reductive alkylation, is a form of amination that involves the conversion of a carbonyl group to an amine linker via an intermediate imine (Schiff's base). The carbonyl group is most commonly a ketone or an aldehyde.

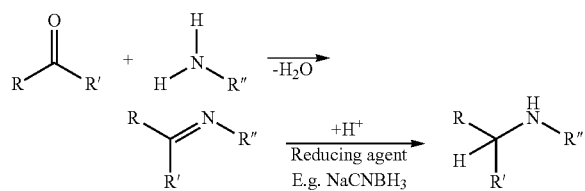

—C—NH—CHR—CHR—C(=O)— Linkage

Michael addition: The Michael reaction or Michael addition is the nucleophilic addition of a carbanion or another nucleophile (e.g. primary amine or thiol) to an alpha, beta unsaturated carbonyl compound. It belongs to the larger class of conjugate additions. This is one of the most useful methods for the mild formation of C—C bonds.

—C—S—C— Linkage

Thio-bromo: Thioether linkages are typically prepared by the alkylation of thiols. Thiols may react with bromide compounds to generate thioether linkages. Such reactions are usually conducted in the presence of base, which converts the thiol into the more nucleophilic thiolate.

Thiol-Ene and Thiol-Yne: Alternatively, thioether linkages may be prepared by reaction of a first compound containing a thiol group with a second compound containing an alkene or an alkyne group. The first and second compounds can each be the surface and the heparin fragment as appropriate.

Suitably the reaction takes place in the presence of a reducing agent such as tris(2-carboxyethyl)phosphine hydrochloride, or alternatively dithiothreitol or sodium borohydride, to avoid or reverse the effective of undesirable coupling of two thiol groups through oxidation.

In one embodiment the reaction is initiated with a radical initiator. An example of a radical initiator is 4,4'-azobis(4-cyanovaleric acid). Further examples are potassium persulfate, 2,2'-azobis[2-(2-imidazolin-2-yl)propane] dihydrochloride, azobisisobutyronitrile (AIBN), 1,2-bis(2-(4,5-dihydro-1H-imidazol-2-yl)propan-2-yl)diazene dihydrochloride, 2,2'-(diazene-1,2-diyl)bis(2-methyl-1-(pyrrolidin-1-yl)propan-1-imine) dihydrochloride, 3,3'-((diazene-1,2-diylbis(1-imino-2-methylpropane-2,1-diyl))bis (azanediyl))dipropanoic acid tetrahydrate, benzophenone and derivatives of benzophenone such as 4-(trimethyl ammoniummethyl) benzophenone chloride.

A further example is ammonium persulfate.

In another embodiment, the reaction is not initiated with a radical initiator. Instead, conditions of higher pH (e.g. pH 8-11) are used. This type of reaction is more suitable when an activated alkene or alkyne is used for reaction with the thiol.

The reaction between a first compound containing a thiol group and a second compound containing an alkyne group may be represented as follows:

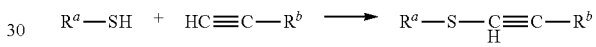

where one of $R^a$ and $R^b$ is the surface and the other of $R^a$ and $R^b$ is the heparin fragment.

When an alkene containing linker is formed, this compound may undergo a further chemical transformation with e.g. a thiol or an amine. Where the second compound is derivatised with an alkene, in one embodiment an activated alkene is used. An example of a suitable activated alkene is a maleimide derivative.

The reaction between a first compound containing a thiol group and a second compound containing a maleimide group may be represented as follows:

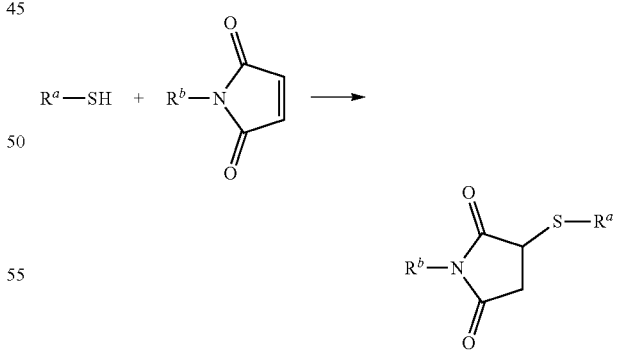

where one of $R^a$ and $R^b$ is the surface and the other of $R^a$ and $R^b$ is the heparin fragment. The reaction is generally carried out in the presence of tris(2-carboxyethyl)phosphine hydrochloride as reducing agent, and 4,4'-azobis(4-cyanovaleric acid) as radical initiator, and under acidic conditions.

Triazole Linkage (CuAAC Coupling)

Azide-Alkyne: 1,2,3-triazole linkages may be prepared by reaction of an alkyne and an azido compound. The reaction to form the linker may be between an alkyne group on the heparin fragment or the surface and an azido group on the other of the heparin fragment or the surface. Methods for carrying out this reaction are similar to the methods described in WO 2010/029189 (herein incorporated by reference in its entirety).

The reaction between the azide and the alkyne groups may be carried out at elevated temperatures (T>60° C.) or in the presence of a metal catalyst, for example a copper, e.g. a Cu(I) catalyst using reaction conditions conventionally used in the Huisgen cycloaddition (the 1,3-dipolar cycloaddition of an azide and a terminal alkyne to form a 1,2,3-triazole). The Cu(I) catalyst may, if desired, be produced in situ, e.g. by reduction of a corresponding Cu(II) compound for example using sodium ascorbate. The reaction may also, if desired, be carried out under flow conditions.

The CuAAC reaction may, for example be carried out at a temperature of from about 5 to 80° C., preferably at about room temperature. The pH used in the reaction may be from about 2-12, preferably about 4-9 and most preferably at about 7. Suitable solvents include those in which the entity attached to the azide or alkyne is soluble, e.g dimethylsulfoxide, dimethylformamide, tetrahydrofuran and preferably water or mixtures of water with one of the above. The proportion of the entity to the surface may be adjusted to provide the desired density of the entity on the surface.

—C(=O)—N— Linkage

Amidation: Amides are commonly formed via reactions of a carboxylic acid with an amine. Carboxylic acids and carboxylic acid derivatives may undergo many chemical transformations, usually through an attack on the carbonyl breaking the carbonyl double bond and forming a tetrahedral intermediate. Thiols, alcohols and amines are all known to serve as nucleophiles. Amides are less reactive under physiological conditions than esters.

Amidation using activated acid: Activated acids (basically esters with a good leaving group e.g. NHS-activated acids) can react with amines to form amide linkers, under conditions where a normal carboxylic acid would just form a salt.

—C—S—S—CH$_2$—CH$_2$—C(=O)—N— Linkage

Coupling using SPDP reagents: The N-succinimidyl 3-(2-pyridyldithio) propionate (SPDP) and its analogues belong to a unique group of amine- and thiol-reactive heterobifunctional link forming reagents that produce disulfide-containing linkages.

Reductive amination, Michael addition, thio-bromo reactions, amidation using NHS-activated acid, coupling using SPDP reagent, CuAAC and thiol-ene couplings are all suitable to provide benign coupling conditions and high yield of linker formation.

The groupings detailed above are for illustrative purposes only and alternative or variant functionalities may of course be employed. For example, the amine groups may be positioned on a secondary carbon or the aliphatic chains illustrated may be replaced by aromatic groups.

Free Radical Initiated Reactions

As mentioned briefly above, the functional end groups of the surface may be coupled to a heparin fragment by a linker formed through a free radical initiated reaction. Radicals may be created for example via heat, photolysis (e.g. Norrish type I and/or Norrish type II reactions), ionization, oxidation, plasma or electrochemical reactions. For example when a surface that has free primary amine groups is treated with benzophenone, radicals such a e.g. carbon or oxygen radicals are created which may participate in free radical initiated reactions (such as reaction with alkenes).

In one embodiment the linker comprises a secondary amine linkage. In particular, the linker may comprise a —NH— group; in another embodiment, the linker comprises an amide linkage. In particular, the linker may comprise a —NH—C(O)— group; in another embodiment the linker comprises a thioether linkage. In another embodiment, the linker comprises a 1,2,3-triazole linkage. The term "thioether linkage" refers to a connection between a sulfur and two carbon atoms. This connection is sometimes referred to as "sulfide". The sulfur may be attached to two saturated carbon atoms (i.e. —C—S—C—) or it may be attached to a saturated and an unsaturated carbon atom (i.e. —C—S—C=). The term "thiol" refers to an —S—H moiety. The term "secondary amine linkage" refers to a connection between an NH group and two carbon atoms, i.e. —C—NH—C—. The term "amide linkage" refers to a connection between two carbon atoms of the type —C—C(O)NH—C—.

In one embodiment, the linker between the heparin fragment and a functional end group of the surface is an unbranched linker. The linker can be biodegradable or non-biodegradable but is more suitably non-biodegradable in order that a coated device is non-thrombogenic for a long period of time.

Where there is a multiplicity of linkers it is possible for some or all of them to be of a different type. In one embodiment, all of the linkers are of the same type.

The fragments of heparin may be bound to the surface directly (i.e. without a linker). Accordingly, in one embodiment, the fragments of heparin are not covalently bound to the surface via any linker.

Covalent binding to the surface must not destroy the active pentasaccharide sequence. Suitably the covalent binding does not interfere with the active pentasaccharide sequence. In the case of a fragment of heparin consisting of 5 saccharide units, since all the sugar units in the pentasaccharide are essential for AT binding, immobilisation must be achieved such that the active sequence is not destroyed. In practice therefore, it is preferable to use a linker in conjunction with pentasaccharide fragments at either the reducing or the non-reducing end-points, so that the immobilisation does not destroy the active sequence. Accordingly, in one embodiment, if the plurality of fragments of heparin include any pentasaccharides, these pentasaccharides are covalently bound to the surface via a linker. Suitably the pentasaccharide is a synthetically produced pentasaccharide and the linker is incorporated into the structure during its synthesis. Suitably the linker is incorporated in a terminal saccharide, suitably at the reducing terminal saccharide and for example at the C1 position.

Figure 4:
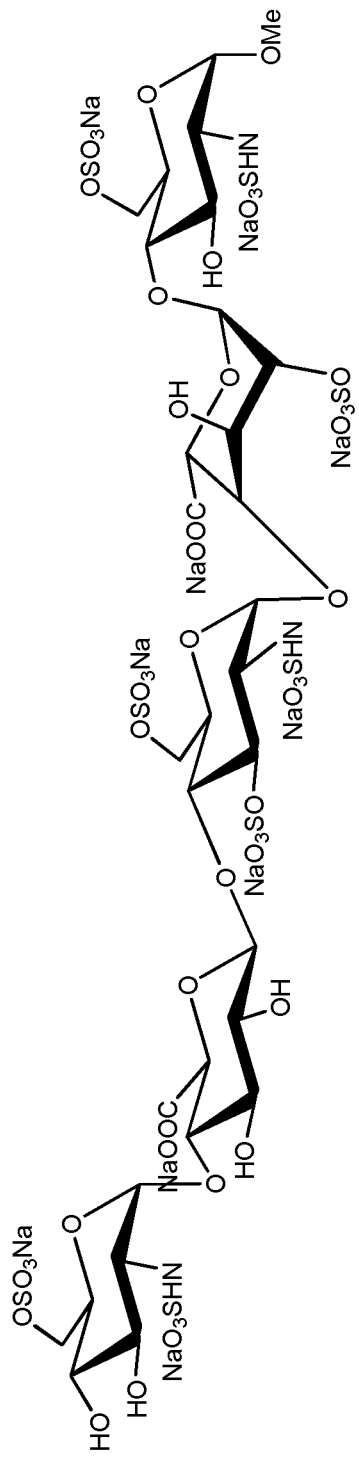
FIG. 4: Fondaparinux sodium/Arixtra®, a synthetically made anticoagulant

Various fragments of heparin may be immobilised on a surface directly or via a linker, including the linkers discussed herein. However, in some circumstances this may not be possible in practice if suitable points of attachment on the heparin fragment are blocked. An example of this is the pentasaccharide Fondaparinux (a synthetically prepared heparin fragment, FIG. 4) which contains the active sequence of heparin. In native Heparin the only position in the structure where synthetic end-point modification is possible is the anomeric carbon in the reducing end, In Fondaparinux this anomeric centre has been modified with a methyl group, protecting the reactive aldehyde group at the reducing end and effectively blocking further modifications. Thus, Fondaparinux is not a suitable heparin fragment for immobilization.

An advantage with immobilizing a synthetically derived heparin fragment is that every heparin fragment can potentially contain the active site that mediates the interaction with AT. As the inventors have shown that immobilization can overcome the disadvantage of shorter heparin fragments (i.e. that they cannot inhibit FIIa when in solution), it is attractive to immobilize a synthetically derived heparin fragment containing the active sequence A on a surface.

Figure 5:
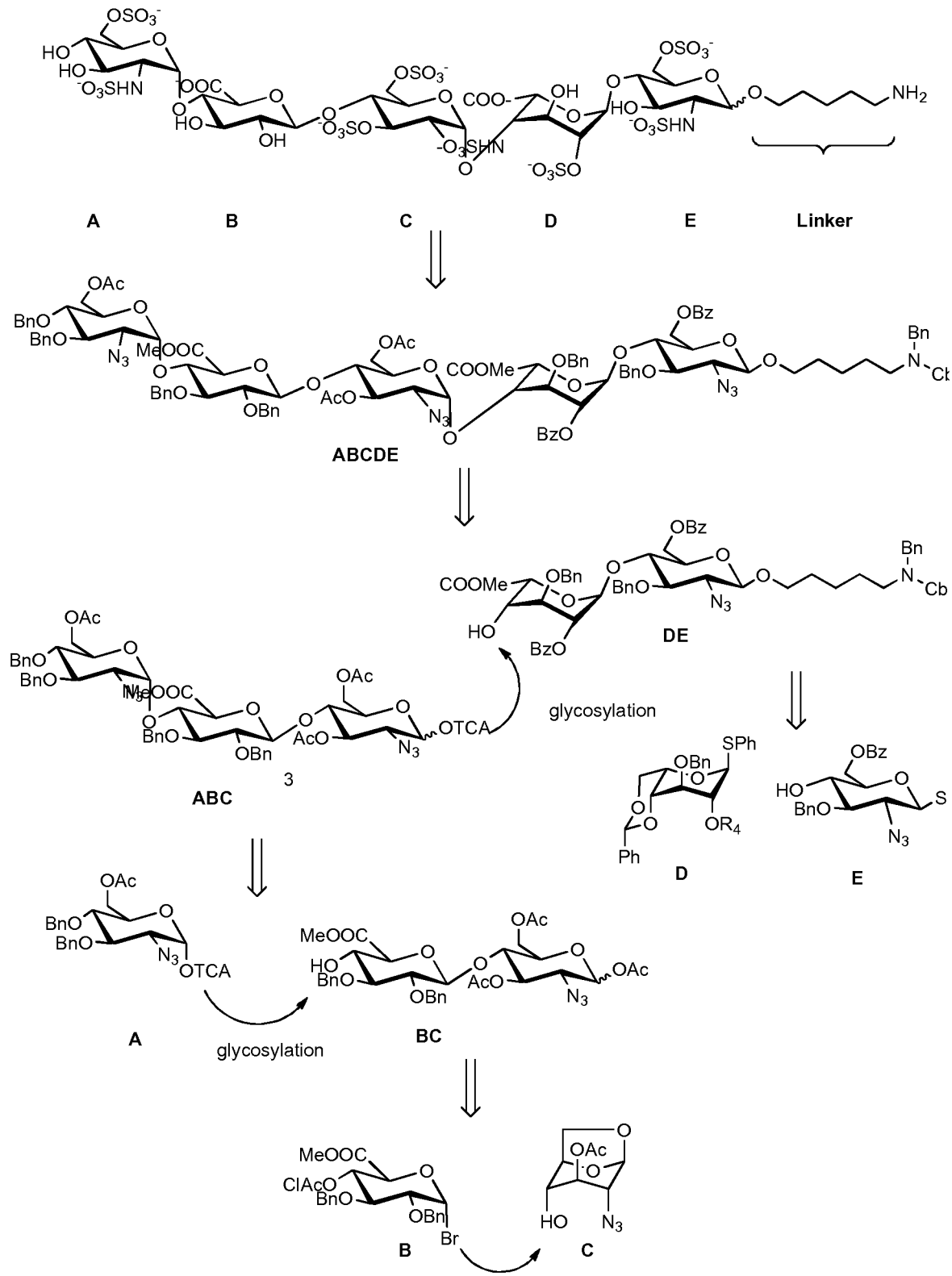
FIG. 5: Retrosynthetic scheme of a pentasaccharide with a linker synthetically incorporated at the reducing end

The Examples below include the synthesis of a pentasaccharide containing the active sequence of heparin, substituted with a linker. Like Fondaparinux, this synthetic pentasaccharide retained the ability to inhibit FXa in solution. FIG. 5 shows a retrosynthetic scheme including the building blocks (A-E), which were coupled to form the pentasaccharide with a linker. The linker was successfully incorporated in the reducing end, enabling end-point attachment to the surface without destroying the active sequence A.

In one embodiment there is provided a method of making an anticoagulant surface comprising covalently binding to a surface a plurality of fragments of heparin, wherein said fragments consist of 5-18 saccharide units and at least some of said plurality of fragments comprise polysaccharide sequence A:

oxygen, carbon, sulphur and nitrogen. In one embodiment the spacer consists of a branched or unbranched $C_{1-15}$ alkylene chain, wherein optionally one or more carbons (for example 1, 2 or 3 carbons, suitably 1 or 2, in particular 1) is/are replaced by a heteroatom selected from O, N or S, especially O or N, wherein said chain is optionally substituted by one or more groups (for example 1 to 3, such as 2 groups) independently selected from oxo, halogen, an aryl group, a heteroaryl group, a carbocyclyl group or a heterocyclyl group. Alkylene as used herein refers to straight chain or branched chain alkylene, such as, without limitation, methylene, ethylene, propylene, iso-propylene, butylene, and tert-butylene. In one embodiment alkylene refers to straight chain alkylene.

The spacer suitably includes functional groups which at one end connect to the heparin fragment (or linker) and at the other end enable covalent binding to the surface.

In one embodiment the spacer consists of a straight alkyl chain which at either end is substituted with functional groups which at one end connect to the heparin fragment (or linker) and at the other end enable covalent binding to the surface.

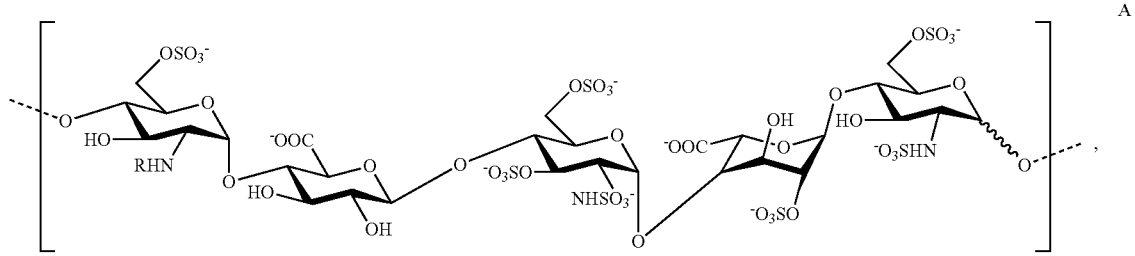

wherein R=Ac or $SO_3^-$
which surface catalyses the inhibition of FIIa and FXa, wherein the fragments of heparin are covalently bound to the surface via linkers.

In one embodiment the fragments of heparin and the linkers attached thereto are simultaneously synthesised, followed by covalently binding the fragments of heparin with linkers to the surface. In one embodiment there is provided an anticoagulant surface obtainable by this method. In one embodiment there is provided an anticoagulant surface obtained by this method.

Spacers

The covalent bond between the functional end group of the surface and the heparin fragment may be direct, or may be via a linker as discussed above. However, optionally the linker may be separated by a spacer from the surface. Accordingly, all embodiments described above relating to the linker being bound to the surface under the 'Linkers' section may equally be applied to the linker being bound to the spacer and/or the spacer being bound to the surface.

The purpose of the spacer, if employed, is usually to significantly increase the separation between the surface and the heparin fragments. For example, the molecular weight of the spacer may be from 50 to $10^6$ Da, typically 100 to $10^6$ Da e.g. 100 to $10^4$ Da. The length of the spacer may for example be from 10 to $10^3$ Å. Suitably the spacer is a straight chain.

In one embodiment the spacer consists of an alkylene chain optionally substituted and in which one or more carbon atoms of the chain may be replaced by heteroatoms selected from oxygen, sulphur and nitrogen. In one embodiment the spacer consists of atoms selected from hydrogen, In some embodiments the spacer is hydrophilic, for example, it may comprise a PEG chain. In one aspect, the covalent connection between the functional end group of the surface and the heparin fragments may be viewed as having three portions—"spacer A" between the functional end group of the surface and the linker, the linker, and "spacer B" between the linker and the heparin fragment. In one embodiment the molecular weight of spacer A is between 50 and $10^3$ Da. In another embodiment the molecular weight of spacer B is between 50 and $10^3$ Da. In one embodiment spacer A comprises one or more aromatic rings. In another embodiment spacer A does not comprise any aromatic rings. In one embodiment spacer B comprises one or more aromatic rings. In another embodiment spacer B does not comprise any aromatic rings. In one embodiment spacer A is hydrophilic. In another embodiment spacer B is hydrophilic. In one embodiment spacer A comprises a PEG chain. In another embodiment spacer B comprises a PEG chain. In one embodiment spacers A and B are both hydrophilic, for example they each comprise a PEG chain. As used herein, a PEG chain refers to a polymeric chain obtainable by polymerisation of ethylene oxide, typically of weight between 100 and $10^6$ Da. In another aspect, the covalent connection may comprise one or more triazole rings.

In cases where spacers are present, they may be straight chain spacers of about 10 to $10^3$ Å. In one embodiment the spacer has a molecular weight of 14 to 200, suitably 14 to 100 Da. In one embodiment the spacer consists of 3 to 50 atoms, suitably 6 to 36 atoms, suitably 9 to 30 atoms, suitably 12 to 22 atoms, suitably about 19 atoms.

A specific merit of having a spacer that comprises a PEG chain (or other hydrophilic polymer) is to provide the surface with lubricious properties.

The spacer can be biodegradable or non-biodegradable but is more suitably non-biodegradable in order that a coated device is non-thrombogenic for along period of time (i.e. the coated device has preserved non-thromogenic properties).

Figure 6:
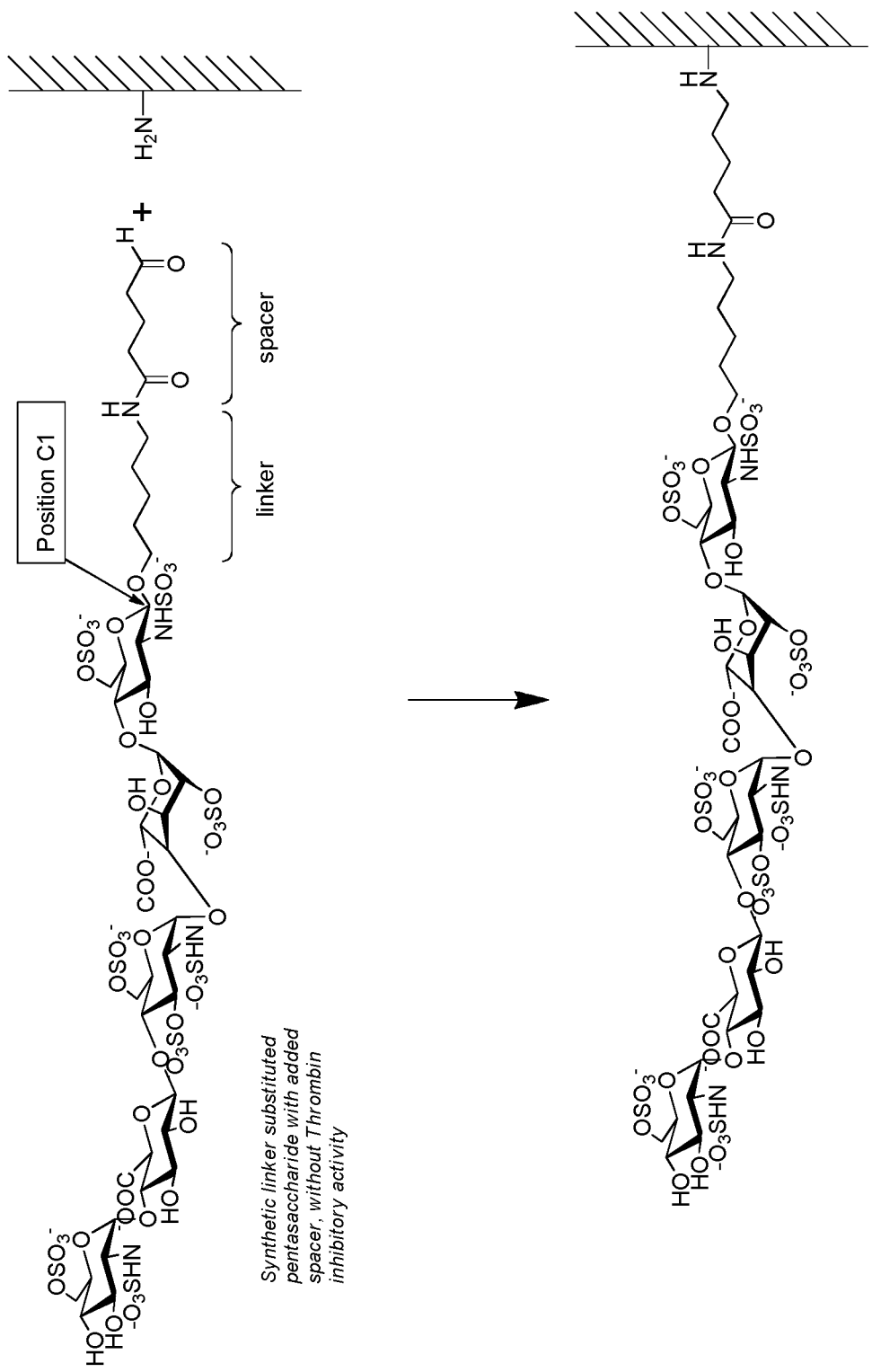
FIG. 6: Synthetic pentasaccharide with a linker at the C1 position of the reducing end containing a functional group that enables immobilization

A pentasaccharide substituted with a linker can be reacted with a spacer substituted with an aldehyde which enables immobilization to the outermost layer of a polyamine via reductive amination, essentially as described by Larm et al in EP0086186A1 and EP0495820B1 (herein incorporated by reference in their entirety), see FIG. 6.

The spacer may be bound to the linker and/or the surface by various means. In one embodiment, the spacer comprises a secondary amine. A representative procedure for covalently bonding a heparin moiety to a polymer via a secondary amine is described in EP0086186B1 (incorporated herein by reference in its entirety). In one embodiment, the spacer comprises a secondary amide. In one embodiment, the spacer comprises a 1,2,3-triazole. In one embodiment, the spacer comprises a thioether. In one embodiment, the plurality of fragments of heparin are not covalently bound to the surface via a spacer comprising a thioether nor a spacer comprising a 1,2,3-triazole.

The spacer can be attached to the reducing or to the non-reducing end of the heparin fragments, suitably the reducing end. Suitably the spacers are single-point attached, more suitably end-point attached to the heparin fragments. More suitably the spacers are bound to the heparin fragments via the reducing end of the heparin fragments and more suitably the spacers are bound to the heparin fragments via position C1 of the reducing end of the heparin fragments.

The exemplary linkers provided above in Table 1 also represent examples of spacers suitable for attaching the spacer to the linker and/or surface. For each spacer in this table, one of the functional end groups is on the surface and/or linker and the other is on the spacer. The illustrative chemistries provided below Table 1 may also be applied in attaching the spacer to the linker and/or surface.

Anticoagulant Properties

As discussed above, the present inventors have surprisingly found that a preparation of heparin-derived oligosaccharides (i.e. heparin fragments), capable of catalysing the inhibition of FXa by AT but devoid of the capacity to catalyse the inhibition of FIIa by AT in solution, is capable of catalysing both reactions when immobilized to a surface. Accordingly, when such a preparation is immobilized to a surface according to the invention, said surface gains anticoagulant properties.

Without wishing to be bound by theory, it is thought that the immobilized oligosaccharides are organized in a way that allows them to act synergistically and/or by coming into close contact with one another thereby forming 'bridges' between oligosaccharides to permit binding and AT mediated inhibition of FIIa. Such activity apparently requires substantially longer molecules in solution. This concept is demonstrated in the Examples below in respect of various fragments of heparin. In particular, octasaccharide fragments of heparin have been prepared and covalently bound to surfaces. Further, a pentasaccharide containing the active sequence of heparin, substituted with a linker, has been synthesized (having the ability to, like Fondaparinux, inhibit FXa in solution but not FIIa in solution). It has been demonstrated that heparin fragments, when covalently bound to a surface according to the invention, are surprisingly capable of inhibiting both FXa and FIIa.

It is important to note that surfaces of the invention comprising heparin fragments are not only anticoagulant by virtue of inhibiting FXa, but their anticoagulant properties are enhanced by their also being capable of inhibiting FIIa. Anticoagulant properties of a surface may be evaluated by various means. The anticoagulant properties of exemplary surfaces of the invention are demonstrated using the Evaluation Methods provided under the Examples.

In one embodiment there is provided a surface according to the invention wherein the surface inhibits FIIa activity by at least 10%, more suitably at least 20%, more suitably at least 30%, more suitably at least 40%, more suitably at least 50%, more suitably at least 60%, more suitably at least 70%, more suitably at least 80%, more suitably at least 90% or more suitably at least 95% when measured according to Evaluation Method G.

Suitably the surface of the invention is for use in catalysing the inhibition of FIIa by AT.

In one embodiment there is provided the use of an anticoagulant surface which surface has covalently bound thereto a plurality of fragments of heparin, wherein said fragments consist of 5-18 saccharide units and at least some of said plurality of fragments comprise polysaccharide sequence A
wherein R=Ac or $SO_3^-$
for catalysing the inhibition of FIIa by AT.

In one embodiment there is provided an anticoagulant surface which surface has covalently bound thereto a plurality of fragments of heparin, wherein said fragments consist of 5-18 saccharide units and at least some of said plurality of fragments comprise polysaccharide sequence A
wherein R=Ac or $SO_3^-$
for use in catalysing the inhibition of FIIa by AT.

In one embodiment there is provided a composition comprising a plurality of fragments of heparin for use in increasing the FIIa inhibition activity of a surface, wherein the plurality of fragments of heparin are covalently bound to the surface and wherein said fragments consist of 5-18 saccharide units and at least some of said plurality of fragments comprise polysaccharide sequence A
wherein R=Ac or $SO_3^-$.

In one embodiment there is provided the use of a composition comprising a plurality of fragments of heparin for increasing the FIIa inhibition activity of a surface, wherein the plurality of fragments of heparin are covalently bound to the surface and wherein said fragments consist of 5-18 saccharide units and at least some of said plurality of fragments comprise polysaccharide sequence A
wherein R=Ac or $SO_3^-$.

In one embodiment there is provided a surface according the invention wherein the surface inhibits FXa activity by at least 10%, more suitably at least 20%, more suitably at least 30%, more suitably at least 40%, more suitably at least 50%, more suitably at least 60%, more suitably at least 70%, more suitably at least 80%, more suitably at least 90% or more suitably at least 95% when measured according to Evaluation Method F.

Suitably the fragments of heparin to be bound to the surface according to the invention have FXa inhibitory activity before they are bound to the surface (i.e. when they are in solution). Accordingly, suitably the fragments of heparin have a FXa inhibitory activity before immobilisation of at least 1 IU/mg, more suitably 5 IU/mg, more suitably 10 IU/mg, more suitably 15 IU/mg, more suitably >100 IU/mg when measured according to Evaluation Method C.

The fragments of heparin immobilized according to the invention will have the ability to bind AT (expressed as pmol AT/surface unit), which may also be referred to as 'heparin activity'. Accordingly, the surface according to the invention may have a heparin activity of at least 0.1 pmol/$cm^2$ of surface, suitably at least 1 pmol/cm$^2$ of surface, suitably at least 2 pmol/cm$^2$ of surface, for binding of AT, when measured according to Evaluation Method J.

Surfaces

Any surface may have covalently bound thereto a plurality of fragments of heparin according to the invention. Suitably the surface comprises functional groups, such as amine, thiol or hydroxy groups which are reacted with the reducing end of the heparin fragments (orthe linker or spacer attached thereto).

In certain embodiments, the surface may be coated and the fragments of heparin may be covalently bound to the coating. The coating may suitably comprise anionic and/or cationic polymers and/or non charged polymers like e.g. polydopamine or fluorine containing polymers.

In certain embodiments of the invention, the surface (also ref erred to as a 'anticoagulant surface' herein) may exhibit a direct pharmacologic inhibition of the coagulation response by immobilization of the anticoagulant entities (the fragments of heparin). In certain embodiments of the invention, the anticoagulant surface does not cause any appreciable clinically-significant adverse reactions such as thrombosis, haemolysis, platelet, leukocyte, and complement activation, and/or other blood-associated adverse event when in contact with blood.

Solid Object

In one embodiment there is provided a solid object comprising a surface according to the invention. Any solid object can potentially be coated with a surface (also referred to as an 'anticoagulant surface' herein) according to the invention, although such coatings are particularly useful for medical devices, analytical devices, separation devices, and other industrial articles including membranes. Most suitably the solid object is a medical device. The surface may refer to a coating on the solid object, or the surface of the solid object itself.

In one embodiment, the solid object is a medical device. When the solid object is a medical device, it is suitably an anticoagulant medical device. Thus, in one embodiment the solid object is an anticoagulant medical device. As used herein, the term "medical device" refers to intracorporeal or extra-corporeal devices but more suitably to intracorporeal medical devices.

Intracorporeal medical devices are devices which are used within the anatomy e.g. within the vasculature or other body lumen, space or cavity, typically to provide a therapeutic effect. Intracorporeal devices may be of long-term or temporary use. Devices of long-term use are left, in part or in whole, in the anatomy after the immediate surgical procedure to deliver them e.g. stents or stent-g rafts. Devices for temporary or short-term use include those which are transiently inserted into a treatment region (i.e. inserted and then removed in the same surgical procedure), such as a medical balloon. In one embodiment, the solid object is an intracorporeal medical device.

Examples of intracorporeal medical devices which can be permanent or temporary intracorporeal medical devices include stents including bifurcated stents, balloon-expandable stents, self-expanding stents, neurovascular stents and flow diverting stents, stent-grafts including bifurcated stent-grafts, grafts including vascular grafts and bifurcated grafts, sheaths including retractable sheaths such as interventional diagnostic and therapeutic sheaths, large and standard bore endovascular delivery sheaths, arterial introducer sheaths with and without hemostatic control and with or without steering, micro-introducer sheaths, dialysis access sheaths, guiding sheaths, and percutaneous sheaths, dilators, occluders such as vascular occluders, embolic filters, embolectomy devices, catheters, artificial blood vessels, blood indwelling monitoring devices, valves including artificial heart valves, pacemaker electrodes, guidewires, cardiac leads, cardiopulmonary bypass circuits, cannulae, plugs, drug delivery devices, balloons, tissue patch devices, blood pumps, patches, lines such as chronic infusion lines or arterial lines, placement wires, devices for continuous subarachnoid infusions, feeding tubes, CNS shunts such as ventriculopleural shunts, ventriculoatrial (VA) shunts, ventriculoperitoneal (VP) shunts, ventricular atrial shunts, portosystemic shunts and shunts for ascites.

Examples of catheters include, but are not limited to, microcatheters, central venous catheters, peripheral intravenous catheters, hemodialysis catheters, catheters such as coated catheters include implantable venous catheters, tunnelled venous catheters, coronary catheters useful for angiography, angioplasty, or ultrasound procedures in the heart or in peripheral veins and arteries, catheters containing spectroscopic or imaging capabilities, hepatic artery infusion catheters, CVC (central venous catheters), peripheral intravenous catheters, peripherally inserted central venous catheters (PIC lines), flow-directed balloon-tipped pulmonary artery catheters, total parenteral nutrition catheters, chronic dwelling catheters (e.g. chronic dwelling gastrointestinal catheters and chronic dwelling genitourinary catheters), peritoneal dialysis catheters, CPB catheters (cardiopulmonary bypass), urinary catheters and microcatheters (e.g. for intracranial application).

In one embodiment, the solid object is an intracorporeal medical device selected from the group consisting of stents, stent-grafts, sheaths, dilators, occluders, valves, embolic filters, embolectomy devices, catheters, artificial blood vessels, blood indwelling monitoring devices, valves, pacemaker electrodes, guidewires, cardiac leads, cardiopulmonary bypass circuits, cannulae, plugs, drug delivery devices, balloons, tissue patch devices, blood pumps, patches, lines, placement wires, devices for continuous subarachnoid infusions, feeding tubes and shunts. In a specific embodiment, the solid object is a stent or a stent-graft.

In one embodiment, said intracorporeal medical device can be used in neurological, peripheral, cardiac, orthopaedic, dermal, or gynaecologic applications. In one embodiment, said stents can be used in cardiac, peripheral or neurological applications. In one embodiment, said stent-grafts can be used in cardiac, peripheral or neurological applications. In one embodiment, said sheaths can be used in carotid, renal, transradial, transseptal, paediatric or micro applications.

Examples of extracorporeal medical devices are blood treatment devices, and transfusion devices. In one embodiment, said intracorporeal medical device can be used in neurological, peripheral, cardiac, orthopaedic, dermal, or gynaecologic applications. In one embodiment the extracorporeal medical device is an oxygenator. In another embodiment the extracorporeal medical device is a filter capable of removing viruses, bacteria, sepsis-causing pro-inflammatory cytokines and toxins.

A membrane can be, for example, a haemodialysis membrane.

An analytical device can be, for example, a solid support for carrying out an analytical process such as chromatography or an immunological assay, reactive chemistry or catalysis. Examples of such devices include slides, beads, well plates and membranes.

A separation device can be, for example, a solid support for carrying out a separation process such as protein purification, affinity chromatography or ion exchange. Examples of such devices include filters and columns.

The solid object may comprise or be formed of a metal, a synthetic or naturally occurring organic or inorganic polymer, a ceramic material, a protein-based material, or a polysaccharide-based material, inter alia.

Suitable metals include, but are not limited to, biocompatible metals such as titanium, stainless steel, high nitrogen stainless steel, cobalt, chromium, nickel, tantalum, niobium, gold, silver, rhodium, zinc, platinum, rubidium, copper and magnesium, and combinations (alloys) thereof.

Suitable alloys include cobalt-chromium alloys such as L-605, MP35N, Elgiloy, titanium alloys including nickel-titanium alloys (such as Nitinol), tantalum alloys, niobium alloys (e.g. Nb-1% Zr), and others. In one embodiment, said biocompatible metal is a nickel-titanium alloy, such as Nitinol.

Synthetic or naturally occurring organic or inorganic polymers include polyolefins, polyesters (e.g. polyethylene terephthalate and polybutylene terephthalate), polyester ethers, polyester elastomer copolymers (e.g. such as those available from DuPont in Wilmington, Del. under the tradename of HYTREL®), fluorine-containing polymers, chlorine-containing polymers (e.g. polyvinyl chloride (PVC)), block copolymer elastomers (e.g. such as those copolymers having styrene end blocks, and midblocks formed from butadiene, isoprene, ethylene/butylene, ethylene/propene), block copolymers (e.g. styrenic block copolymers such as acrylonitrile-styrene and acrylonitrile-butadiene-styrene block copolymers, or block copolymers wherein the particular block copolymer thermoplastic elastomers in which the block copolymer is made up of hard segments of a polyester or polyamide and soft segments of polyether), polyurethanes, polyamides (e.g. nylon 12, nylon 11, nylon 9, nylon 6/9 and nylon 6/6), polyether block amides (e.g. PEBAX®), polyetheresteramide, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylamide, polyacrylic acid, polystyrenes, polytetrafluoroethylene, poly(methyl)methacrylates, polyacrylonitriles, poly(vinylacetates), poly(vinyl alcohols), polyoxymethylenes, polycarbonates, phenolics, amino-epoxy resins, cellulose-based plastics, and rubber-like plastics, bioresorbables (e.g. poly(D,L-lactide) and polyglycolids, and copolymers thereof and copolymers thereof), derivatives thereof and mixtures thereof. Combinations of these materials can be employed with and without cross-linking. Some of these classes are available both as thermosets and as thermoplastic polymers. As used herein, the term "copolymer" shall be used to refer to any polymer formed from two or more monomers, e.g. 2, 3, 4, 5 and so on and so forth.

Fluorinated polymers (fluorine-containing polymers) include fluoropolymers such as expanded polytetrafluoroethylene (ePTFE), polytetrafluoroethylene (PTFE), fluorinated ethylene-propylene (FEP), perfluorocarbon copolymers (such as tetrafluoroethylene perfluoroalkylvinyl ether (TFE/PAVE) copolymers and copolymers of tetrafluoroethylene (TFE) and perfluoromethyl vinyl ether (PMVE)), and combinations of the above with and without crosslinking between the polymer chains.

In one embodiment, the solid object comprises a polyether-block-amide, such as PEBAX®. In another embodiment, the solid object comprises a chlorine-containing polymer (e.g. PVC) or a fluorine-containing polymer (e.g. ePTFE).

Polymeric substrates may optionally be blended with fillers and/or colorants. Thus, suitable substrates include pigmented materials such as pigmented polymeric materials.

Ceramic substrates may include, but are not limited to, silicone oxides, aluminium oxides, alumina, silica, hydroxyapapitites, glasses, calcium oxides, polysilanols, and phosphorous oxide.

Protein-based materials include silk and wool. Polysaccharide-based materials include agarose and alginate.

Cationic and Anionic Polymers

Suitably the surface comprises a layer of one or more cationic and/or anionic polymer. Suitably the fragments of heparin are bound to the outermost layer of cationic polymer, suitably via a linker. In one embodiment there is provided a solid object wherein the surface comprises a layer by layer coating, the outer coating layer being a cationic polymer to which the fragments of heparin are covalently bound. Suitably the layer by layer coating is an alternating layer of cationic and anionic polymers. More suitably the cationic polymer layers are layers of cationic polymeric amines and/or the anionic polymer layers are layers of dextran sulfate.

The cationic polymer may be a straight chain polymer but is more usually a branched polymer such as a hyperbranched polymer. In one embodiment the branched polymer has a consistent branched structure with defined features such as core moieties. In another embodiment the branched polymer has a consistent or randomly branched structure lacking defined features such as core moieties. A 'core moiety' is a group which may be present in a branched polymer molecule (typically at the center) from which the tree like branching structure of a branched polymer emanates.

In one embodiment the cationic polymer is a branched cationic polymer. The cationic polymer is optionally cross-linked. In one embodiment, the cationic polymer comprises primary/secondary amine groups. In one embodiment, the cationic polymer is a polyamine, which is optionally cross-linked, suitably with a difunctional aldehyde. The cationic polymer (e.g. polyamine), suitably has molecular weight of 5 kDa-3,000 kDa, such as 5 kDa-2,000 kDa, 5 kDa-1,500 kDa, 5 kDa-1,000 kDa, 5 kDa-800 kDa, 5 kDa-500 kDa, 5 kDa-300 kDa, 5 kDa-200 kDa or 800 kDa-3,000 kDa. The cationic polymer (e.g. polyamine), suitably has molecular weight of at least 5 kDa, such as at least 10 kDa, such as at least 25 kDa, such as at least 50, such as at least 60, such as at least 70 kDa. The cationic polymer (e.g. polyamine), suitably has molecular weight of no more than 2000 kDa, such as no more than 1500 kDa, such as no more than 1300 kDa, such as no more than 1200 kDa, such as no more than 1100 kDa, such as no more than 1000 kDa. When the cationic polymer (e.g. polyamine) is cross-linked, it is suitably cross-linked using an aldehyde cross-linker such as crotonaldehyde and/or glutaraldehyde. In one embodiment, the cationic polymer is a polyalkyleneimine e.g. polyethyleneimine.

Suitably the fragments of heparin are covalently attached to the outermost layer of cationic polymer.

The cationic polymer may form part of a layer-by-layer coating of cationic polymer and anionic polymer, which is formed by alternately treating the surface of the solid object with layers of cationic and anionic polymer. A bilayer is defined herein as one layer of cationic polymer and anionic polymer. In the layer-by-layer coating, the cationic polymer is typically applied before the anionic polymer i.e. a surface of the solid object is typically first treated with a first layer of cationic polymer (step i), upon which a first layer of anionic polymer is applied (step ii). Depending on the number of bilayers required, further layers of cationic polymer and anionic polymer may be applied (step iii). When the final (which may be also the first) bilayer of cationic and anionic polymer is completed, a layer of cationic polymer is then applied (step iv). This layer (i.e. the outermost layer) of cationic polymer is then treated with heparin fragments, so as to covalently attach the heparin fragments to the layer of cationic polymer. Thus, the outer coating layer of cationic polymer can be said to "comprise" fragments of heparin. In the layer-by-layer coating, the innermost layer is a layer of cationic polymer and the outermost layer is an outer coating layer of cationic polymer to which the fragments of heparin are covalently attached.

In one embodiment, the cationic polymer of step i is a polyamine, which is optionally cross-linked. In one embodiment, the cationic polymer of step iv is a polyamine, which is optionally cross-linked. In one embodiment, the cationic polymer of step i is the same as the cationic polymer of step iv.

WO2012/123384A1 (Gore Enterprise Holdings, Inc. et al., incorporated herein by reference in its entirety) discloses a device with a coating comprising a plurality of hyperbranched polymer molecules bearing anticoagulant entities, in particular heparin. Such hyperbranched polymer molecules may be utilised in the outermost layer of cationic polymer i.e. such hyperbranched polymers may be used as the cationic polymer of step iv, and then modified to bear fragments of heparin in step v.

Anionic polymers suitable for the invention carry deprotonated functional groups from the groups consisting of —COOH, —SO$_3$H and —PO$_3$H$_2$. Thus, in one embodiment, the anionic polymer is a polymer comprising groups selected from —CO$_2^-$, —SO$_3^-$, —PO$_3$H$^-$ and —PO$_3^{2-}$.

The anionic polymer is suitably an anionic glycosaminoglycan or polysaccharide. The anionic characteristics of the polymer typically derive from carboxylate or sulfate groups along the polymer chain. Thus, in one embodiment, the anionic polymer is a glycosaminoglycan or polysaccharide bearing carboxylate and/or sulfate groups, in particular a glycosaminoglycan bearing carboxylate and/or sulfate groups. The anionic polymer may be branched or unbranched. In one embodiment, the anionic polymer is optionally cross-linked.

In one embodiment, the anionic polymer is selected from the group consisting of dextran sulfate, hyaluronic acid, poly(2-acrylamido-2-methyl-1-propanesulfonic acid), poly(2-acrylamido-2-methyl-1-propanesulfonic acid-co-acrylonitrile) acrylonitrile, poly(acrylic acid), polyanetholesulfonic acid, poly(sodium 4-styrenesulfonate), poly(4-styrenesulfonic acid-co-maleic acid), poly(vinyl sulfate), polyvinylsulfonic acid and salts thereof. Suitably, the anionic polymer is dextran sulfate. Dextran sulfate is a sulfated polymer of anhydroglucose. The degree of sulfation and consequently the sulfur content of the dextran sulfate can vary.

In one embodiment, the anionic polymer is characterized by having a total molecular weight of 550 kDa-10,000 kDa, such as 650 kDa-10,000 kDa, such as 750 kDa-10,000 kDa, such as 1,000 kDa-10,000 kDa. In one embodiment, the anionic polymer is characterized by having a total molecular weight of 650 kDa-1,000 kDa, e.g. 750 kDa-1,000 kDa. In one embodiment, the anionic polymer is characterized by having a total molecular weight of 1,000 kDa-4,500 kDa e.g. 2,000 kDa-4,500 kDa. In one embodiment, the anionic polymer is characterized by having a total molecular weight of 4,500 kDa-7,000 kDa. In one embodiment, the anionic polymer is characterized by having a total molecular weight of 7,000 kDa-10,000 kDa. In one embodiment, the anionic polymer is characterized by having a total molecular weight of greater than 1,000 kDa, such as greater than 2,000 kDa, such as greater than 3,000 kDa, such as greater than 3,500 kDa. Suitably the anionic polymer is characterized by having a total molecular weight of less than 7,000 kDa, such as less than 6,000 kDa, such as less than 5,000 kDa, such as less than 4,500 kDa. Suitably, the total molecular weight of the anionic polymer is measured according to Evaluation Method K.

In one embodiment, the anionic polymer is characterized by having a solution charge density of 1 µeq/g to 7 µeq/g, such as 2 µeq/g to 4 µeq/g or else >4 µeq/g to 7 µeq/g such >5 µeq/g to 7 µeq/g. Suitably, the solution charge density of the anionic polymer is measured according to Evaluation Method L In some embodiments the sulfur content in the cationic and/or anionic polymers is between 10% and 25% by weight, e.g. the sulfur content is between 15% and 20% by weight.

The layer by layer coating may comprise one or more coating bilayers, e.g. 2 or more, 3 or more, 4 or more, 5 or more, 6 or more, 7 or more, 8 or more, 9 or more or 10 or more coating bilayers.

Typically, the coating layer will have an average total thickness of about 10 nm to about 1000 nm, e.g. about 10 nm to about 800 nm, e.g. about 10 mM to about 500 nm, about 10 nm to about 400 nm, about 10 nm to about 300 nm, about 10 nm to about 200 nm or about 10 nm to about 100 nm. Coating thickness can be measured using a suitable coating thickness analyser or gauge, by using X-ray photoelectron spectroscopy with depth profiling or by using Quartz Crystal Microbalance with Dissipation.

In one embodiment the surface does not comprise a layered coating.

In one embodiment the surface does not comprise a layered coating wherein the outer coating layer comprises a plurality of cationic hyperbranched polymer molecules characterized by having a core moiety of molecular weight 14-1,000 Da and a ratio of total molecular weight to core moiety molecular weight of at least 80:1.

In one embodiment the surface does not comprise a layered coating wherein the outer coating layer comprises a plurality of cationic hyperbranched polymer molecules characterized by having (i) a core moiety of molecular weight 14-1,000 Da (ii) a total molecular weight of 1,500 to 1,000,000 Da (iii) a ratio of total molecular weight to core moiety molecular weight of at least 80:1 (e.g. at least 100:1) and (iv) functional end groups, whereby one or more of said functional end groups have an anti-coagulant entity covalently attached thereto.

Therapeutic Methods

Surfaces according to the invention are of use in medical therapy. In one aspect of the invention there is provided a solid object (in particular a medical device such as a stent, graft or stent-graft) according to the invention for use in treating tissue in the human or animal body. The tissue to be treated includes any body cavity, space, or hollow organ passage(s) such as blood vessels, the urinary tract, the intestinal tract, nasal cavity, neural sheath, intervertebral regions, bone cavities, oesophagus, intrauterine spaces, pancreatic and bile ducts, rectum, and those previously intervened body spaces that have implanted vascular grafts, stents, prosthesis, or other type of medical implants. In yet another aspect of the invention, a solid object (in particular a medical device such as a stent, graft or stent-graft) according to the invention may be deployed to treat aneurysms in the brain.

The solid object (in particular a medical device such as a stent, graft or stent-graft) according to the invention can be of use in the removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters.

In one embodiment is provided a solid object (in particular a medical device such as a stent, graft or stent-graft) according to the invention for use in the prevention or treatment of stenosis or restenosis in a blood vessel of the human body. In another embodiment is provided a solid object (in particular a medical device such as a stent, graft or stent-graft) according to the invention for use in the prevention or treatment of stenosis or restenosis in a blood vessel of the human body, where previously placed eluting constructs have failed. In another embodiment, a solid object (in particular a medical device such as a stent, graft or stent-graft) according to the invention can be used to establish or maintain arteriovenous access sites, e.g. those used during kidney dialysis. In a further embodiment, a solid object (in particular a medical device such as a stent, graft or stent-graft e.g. a vascular graft) according to the invention may be used to redirect flow around an area of blockage or vessel narrowing. In another embodiment, a solid object (in particular a medical device such as a stent, graft or stent-graft) according to the invention may be deployed to restore patency to an area of diseased vessel or to exclude an aneurysm. In yet another embodiment, a sold object (in particular a medical device such as a stent, graft or stent-graft) according to the invention may be deployed to reinforce a diseased vessel following angioplasty. In yet another embodiment, a solid object (in particular a medical device such as a stent, graft or stent-graft) according to the invention may be deployed in the brain using balloon assisted or coil assisted procedures.

In one embodiment, a solid object (in particular a medical device) according to the invention can be used for Percutaneous Transluminal Angioplasty (PTA) in patients with obstructive disease of the peripheral arteries.

In another aspect of the invention is provided a method for the prevention or treatment of stenosis or restenosis which comprises implanting into a blood vessel in the human or animal body a solid object (in particular a medical device) according to the invention.

Abbreviations
  Ac Acetyl
  ACN Acetonnitrile
  Ac₂O Acetic anhydride
  AcOH Acetic acid
  AgOTf Silver triflate
  AT, ATIII antithrombin III
  BAIB bis(acetoxy)iodobenzene
  BDMA Benzaldehyde dimethyl acetal
  Bn Benzyl
  Bu Butyl
  Bz Benzoyl
  Cbz Carboxybenzyl
  CNS central nervous system
  COSY COrrelated SpectroscopY
  CPB cardiopulmonary bypass
  Cq quarternary Carbon
  CSA (+/−)-10-Camphorsulfonic acid
  CVC central venous catheter
  Da Dalton
  DBU 1,8-Diazabicyclo(5.4.0)undec-7-ene
  DMF Dimethylformamide
  DMAPA Dimethylaminopropylamine
  EDC 1-ethyl-3-(3-dimethylaminopropyl)-carbodiimide
  EDA Ethylenediamine
  Et Ethyl
  Et₂O Diethylether
  EtOAc Ethyl acetate
  EtOH Ethanol
  Eq Equivalent
  FEP fluorinated ethylene-propylene
  FIIa coagulation factor IIa, Thrombin
  FXa coagulation factor Xa
  GPC gel permeation chromatography
  HMBC Heteronuclear multiple bond correlation spectroscopy
  HSQC Heteronuclear single quantum coherence
  HRMS High Resolution Mass Spectrometry
  HSA Human serum albumin
  HSEt Ethanethiol
  HSPh Thiophenol
  M molar concentration
  MBTH 3-methyl-2-benzothiazolinone hydrazone hydrochloride
  Me Methyl
  Ms Mesyl
  NIS N-iodosuccinimide
  NMR Nuclear magnetic resonance
  OTCA trichloroacetimidate
  OTf Triflate, trifluoromethanesulfonate
  PAVE perfluoroalkylvinyl ether
  PES-Na sodium polyethylene sulfate
  Ph. Eur. European Pharmacopoeia
  Phth Phtalic
  PTA percutaneous transluminal angioplasty
  PMVE perfluoromethyl vinyl ether
  PPM parts per million
  PTFE polytetrafluoroethylene
  PVC polyvinyl chloride
  $R_f$ Retention factor
  rt Room temperature
  SPDP N-succinimidyl 3-(2-pyridyldithio)propionate
  TBDMS tert-Butyldimethylsilyl
  TBSOTf tert-Butyldimethylsilyl triflate
  TEA Triethylamine
  TEMPO (2,2,6,6-Tetramethylpiperidin-1-yl)oxyl
  TFE tetrafluoroethylene
  THF Tetrahydrofuran
  TLC Thin layer Chromatography
  TMB 3,3',5,5'-tetramethylbenzidine
  TMS Trimethylsilyl
  TMSOTf Trimethylsilyl triflate
  Tol Toluene
  Tris tris(hydroxymethyl)aminomethane, buffer solution
  p-TsOH para-Tolenesulfonic acid
  USP United States Pharmacopeia
  VA ventriculoatrial
  VP ventriculoperitoneal Clauses Clauses describing further embodiments of the invention are as follows:
  1. An anticoagulant surface which surface has covalently bound thereto a plurality of fragments of heparin, wherein said fragments consist of 5-18 saccharide units and at least some of said plurality of fragments comprise polysaccharide sequence A:

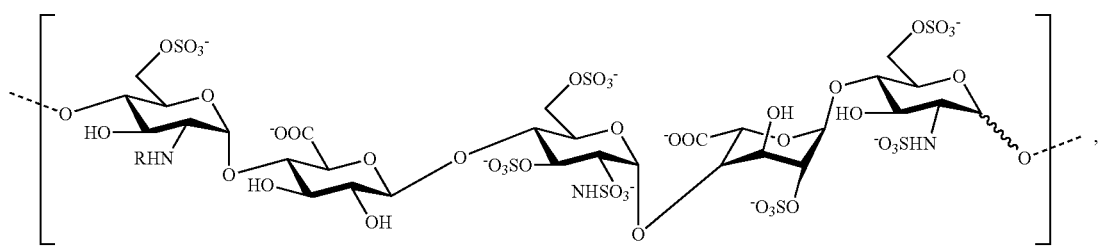

wherein R=Ac or $SO_3^-$
which surface catalyses the inhibition of FIIa and FXa by AT.
2. A surface according to clause 1 wherein the surface inhibits FIIa activity by at least 50% when measured according to Evaluation Method G.
3. A surface according to either clause 1 or 2 wherein the fragments of heparin are heterogeneous in structure.
4. A surface according to either clause 1 or 2 wherein said fragments of heparin are homogeneous in structure and all comprise polysaccharide sequence A.
5. A surface according to any one of clauses 1 to 4 wherein said fragments of heparin are fragments of native heparin produced by a process comprising degrading native heparin.
6. A surface according to any one of clauses 1 to 4 wherein said fragments of heparin are synthetically produced.
7. A surface according to any one of clauses 1 to 6 wherein the fragments of heparin are covalently bound to the surface via a linker.
8. A surface according to any one of clauses 1 to 7 wherein the fragments of heparin are single-point attached.
9. A surface according to clause 8 wherein the fragments of heparin are end-point attached.
10. A surface according to clause 9 wherein the fragments of heparin are covalently bound to the surface via their reducing end.
11. A surface according to any one of clauses 1 to 10 which has heparin activity of at least 1 pmol/cm$^2$ of surface e.g. at least 2 pmol/cm$^2$ of surface, at least 3 pmol/cm$^2$ of surface, at least 4 pmol/cm$^2$ of surface, or at least 5 pmol/cm$^2$ of surface for binding of AT, suitably measured according to Evaluation Method J.
12. A surface according to any one of clauses 1 to 11 which has a heparin concentration of at least 1 µg/cm$^2$, e.g. at least 2 µg/cm$^2$, at least 4 µg/cm$^2$, at least 5 µg/cm$^2$, or at least 6 µg/cm$^2$, suitably measured according Evaluation Method H.
13. A surface according to any one of clauses 1 to 12 wherein said fragments of heparin consist of at least 6 saccharide units.
14. A surface according to any one of clauses 1 to 13 wherein said fragments of heparin consist of no more than 14 saccharide units.
15. A surface according to clause 7 wherein the linker comprises formula (I)

wherein n is 1 to 20 and m is 1 to 20.

EXAMPLES

General Procedures
Evaluation Methods
When preparing the reaction mixtures in Evaluation Methods C-G below, the enzyme solutions (FXa and FIIa) were consistently added last, immediately before initiation of the incubation.

Evaluation Method A: Molecular Weight Determination of the Heparin Fragment Fractions
The molecular weight of Heparin fragment fractions are determined by analytical gel permeation chromatography (GPC) on a system consisting of two Superdex columns in series (S-75 and S-200) essentially according to USP<209> Low Molecular Weight Heparin Molecular Weight Determinations. Peak positions are identified based on the elution profile of the 2$^{nd}$ International Standard for Low Molecular Weight Heparin for Molecular Weight Calibration (NIBSC, UK), where the least retarded peak of the standard is a disaccharide.
Evaluation Method B: Heparin Fragment Concentration Determination
The quantities of isolated heparin fragment in solution are estimated by analyzing the uronic acid content by the carbazole assay (Bitter, T.; Muir, N. M., Anal. Biochem., 1962, (4), 330-334), related to a heparin standard curve.
Evaluation Method C: Anti-FXa Activity Determination of Heparin Fragments in Solution, Compared with International Standard
The anticoagulant activity of the heparin fragments are determined in an anti-FXa assay. This method measures anti-FXa activity of heparin essentially according to USP<208> Anti-FXa and Anti-FIIa assays for unfractionated and low molecular weight heparins. The method is based on heparin's ability to accelerate antithrombin inhibition of FXa in vitro, where the residual FXa activity is detected using a chromogenic FXa substrate (CS 11(65)). The results expressed as IU/mg (international unit/mg) are calculated using the parallel-line model, towards the Low Molecular Heparin 2nd International Standard.
Evaluation Method D: Determination of Anti-FXa Activity of Heparin Fragments in Solution
A reaction mixture containing the heparin fragment (at a final concentration of 0.2 mg/ml), AT (0.03 IU/mL), FXa (0.5 µg/mL), Tris (17 mM, pH 7.4), NaCl (60 mM), HSA (1 mg/mL)) and PEG-6000 (2 mg/mL) is incubated at the time interval of 0, 5, 10, 20 and 30 min at room temperature essentially as Method C, 250 µl of the reaction mixtures are transferred to test tubes on ice. The residual FXa activity is then determined by transferring 150 µl of the incubated solutions to wells in a microtiter plate containing 150 µl a chromogenic FXa substrate (CS 11(65), 0.5 mM). The absorbance at 405 nm is recorded kinetically for two minutes in a plate reader giving the FXa activity as mOD/min (mean Optical density/min).
Evaluation Method E: Determination of Anti-FIIa Activity of Heparin Fragments in Solution
A reaction mixture containing heparin fragments (0.2 mg/ml) in a solution containing AT (0.02 IU/mL), FIIa (2.5 IU/ml), Tris (17 mM, pH 7.4), NaCl (60 mM), HSA (1 mg/mL)) and PEG-6000 (2 mg/mL), is incubated at room temperature essentially as Method C, at the time interval of 0, 5, 10, 20 and 30 min. The reaction mixtures are transferred to a test tube on ice. The residual FIIa activity is then determined by transferring the incubated solutions to wells in a microtiter plate containing a chromogenic FIIa substrate (CS 11(38), final concentration 0.25 mM). The absorbance at 405 nm is recorded kinetically for two minutes in a plate reader giving the FIIa activity as mOD/min (mean Optical density/min).

Evaluation Method F: Determination of Anti-FXa Activity of Immobilized Heparin Fragments Loops are prepared from pieces of tubing (16.5 cm including 1.5 cm required to connect end-to-end using short pieces of 2 mm i.d. PE tubing). Aliquots of the reaction mixture (1.5 mL), containing AT (0.03 IU/mL), FXa (0.5 µg/mL), Tris (17 mM, pH 7.4), NaCl (60 mM), HSA (1 mg/mL)) and PEG-6000 (2 mg/mL) are transferred to the loops and circulated for 10 minutes. At the end of the incubation, reaction mixtures are transferred to test tubes in an ice bath and 150 µl of the incubated solutions are transferred to wells in a microtiter plate and mixed with 150 µl FXa substrate (0.5 mM). The residual FXa activity is then determined essentially as in Evaluation Method D. As a negative control, the same reaction mixture is incubated in test tubes or loops of uncoated PVC tubing. The results are normalized to the uncoated PVC, expressing the results as % inhibition of FXa.

Evaluation Method G: Determination of Anti-FIIa Activity of Immobilized Heparin Fragments Loops (15 cm) are prepared from pieces of tubing (16.5 cm including 1.5 cm required to connect end-to-end using short pieces of 2 mm i.d. PE tubing). Aliquots of the reaction mixture, containing AT (0.02 IU/ml), FIIa (2.5 IU/ml), Tris (17 mM, pH 7.4), NaCl (60 mM), HSA (1 mg/mL)) and PEG-6000 (2 mg/mL) is transferred to the loops and circulated for 10 minutes. At the end of the incubation, the reaction mixtures (250 µl) are transferred to test tubes in an ice bath. The residual FIIa activity is then determined essentially as in Evaluation Method E. As a negative control the same reaction mixture was incubated in test tubes or loops of uncoated PVC tubing. The results are normalized to the uncoated PVC, expressing the results as % inhibition of FIIa.

Evaluation Method H: Quantification of Surface Immobilized Heparin Fragments (Heparin Density)

Quantification of surface immobilized heparin is performed by complete degradation of heparin followed by colorimetric determination of the reaction products released into solution. Degradation is achieved by reacting the heparin surface with an excess of sodium nitrite under acidic conditions. The degradation products, mainly disaccharides, are quantified calorimetrically in a reaction with MBTH (3-methyl-2-benzothiazolinone hydrazine hydrochloride), essentially as described in Smith R. L. and Gilkerson E (1979), Anal Biochem 98, 478-480, which is incorporated herein by reference in its entirety.

Evaluation Method I: Toluidine Blue Staining Test (Heparin Distribution)

Heparin distribution is evaluated using toluidine blue staining solution. The solution is prepared by dissolving 200 mg of toluidine blue in 1 L of water. The samples are subjected to the staining solution for 2 minutes prior to extensive water rinse. A blue/violet staining indicates that negatively charged heparin molecules are homogenously distributed in the outer coating layer.

Evaluation Method J: Heparin Activity Test (Immobilized Heparin Functionality)

For solid objects coated according to the process of the invention comprising a heparin fragments coating, the heparin activity of the solid object can be measured by measuring the ability, or capacity, of the heparin to bind AT as described by Pasche, et al. in "A binding of antithrombin to immobilized heparin under varying flow conditions" (Artif. Organs 1991; 15:281-491, incorporated herein by reference in its entirety) and Larsen M. L, et al. in "Assay of plasma heparin using thrombin and the chromogenic substrate H-D-Phe-Pip-Arg-pNA" (S-2238) (Thromb. Res. 1978; 13:285-288, incorporated herein by reference in its entirety. Washed samples are incubated with an excess of antithrombin in solution to saturate all available antithrombin-binding sites of the heparin surface. Non-specifically adsorbed antithrombin is rinsed away using a salt solution. Subsequently, antithrombin specifically bound to the immobilized heparin is released by incubating with a solution of heparin at high concentration. Finally, the antithrombin released from the heparin surface is measured in a thrombin inhibition assay, based on a chromogenic thrombin substrate. The results are expressed as picomoles AT bound per apparent square centimeter of device (pmol AT/cm$^2$ solid object surface). The apparent solid object surface area does not take into account multiple covered surfaces nor porosity considerations of a solid object composed of a porous material. If the surface of the solid object is porous, the effect of porosity on surface area is not considered for these calculations. For example, the apparent surface area of a cylindrical tubular ePTFE vascular graft (which is made of a porous material) with heparin immobilized on substrate material comprising the inner surface of the tubular graft is calculated as it is for any cylindrical geometry as $2\pi rL$: where r is the graft inner radius; L is the axial length; and $\pi$ is the number pi. This method can be used to measure the activity of any anticoagulant entity with AT binding activity.

Evaluation Method K: Molecular Weight of Dextran Sulfate in Solution (Molecular Weight of Anionic Polymer)

Determination of the molecular weight of a dextran sulfate sample is performed on a gel permeation chromatography (GPC) instrument. The dextran sulfate samples are dissolved in a water-based elution media and analyzed on a GPC instrument suitable for the molecular weight range 1,000 Da-100,000 Da (superose column) or 100,000 Da-2,000,000 Da (sephacryl column). A dextran sulfate standard of an appropriate molecular weight is used to verify the accuracy of the calibration curve. Polymers such as dextran sulfate are disperse molecules i.e. have a distribution of molecular weights, which can be described with different molecular weight averages. The commonly reported value is the weight average molecular weight (Mw). See Odian G., Principles of Polymerization, Third edition, Section 1.4 Molecular weight, p. 24 (incorporated herein by reference in its entirety) which explains the theory on determination of molecular weights of polymers using GPC techniques. The molecular weight of anionic polymers other than dextran sulfate can be determined using this method.

Evaluation Method L: Solution Charge Density of Dextran Sulfate in Solution (Solution Charge Density of Anionic Polymer)

Quantitative determination of charge density is performed on a Mütek Particle Charge Detector via titration of polyelectrolyte solutions (0.001 M) (polydiallyldimethylammonium chloride (Poly-Dadmac) and sodium polyethylene sulfate (PES-Na)). Samples are dissolved in water (maximum viscosity allowed 6000 mPas) to a concentration of 0.06 g/L. The pH is adjusted to 3 for all sample solutions. 10 mL per sample solution is added each measurement followed by titration of appropriate polyelectrolyte solution at an interval of 1 unit per 3 seconds. See S. Farris et al., Charge Density Quantification of Polyelectrolyte Polysaccharides by Conductometric Titration: An Analytical Chemistry Experiment, J. Chem. Educ., 2012, 89 (1), pp 121-124 (incorporated herein by reference in its entirety). The solution charge density of anionic polymers other than dextran sulfate can be determined using this method.

PREPARATIVE EXAMPLES AND TESTING

Preparation of Synthetic Pentasaccharide with Incorporated End Point Attached Linker
General Procedures Unless otherwise noted, reactions were performed with rigorous exclusion of air and moisture, under an inert atmosphere of nitrogen in oven-dried glassware with magnetic stirring. $N_2$-flushed stainless cannulas or plastic syringes were used to transfer air- and moisture-sensitive reagents. Oxygen-free nitrogen was obtained from BOC gases. Evaporation in vacuo refers to the removal of volatiles on a Buchi rotary evaporator with integrated vacuum pump. Silica gel chromatography was carried out using Davisil LC60A $SiO_2$ (40-63 μm) silica gel. All reactions were monitored by thin-layer chromatography (TLC). TLC was performed on Merck DC-Alufolien plates precoated with silica gel 60 F254. They were visualised with UV-light (254 nm) fluorescence quenching, and/or by charring with an 8% $H_2SO_4$ dip (stock solution: 8 mL conc. $H_2SO_4$, 92 mL EtOH), and/or ninhydrin dip (stock solution: 0.3 g ninhydrin, 3 mL AcOH, 100 mL EtOH)

Materials

Two disaccharides intermediates I.63 and I.66 was purchased from Heparin Building Blocks. All other chemicals for the synthesis were purchased from commercial suppliers (Acros, Carbosynth Ltd, Fischer Scientific Ltd, Merck, Sigma-Aldrich Corp, and VWR) and were used without further purification. Dry $CH_2Cl_2$, $Et_2O$ and THF reaction solvents were obtained from a PureSolv-EN™ solvent purification system. All other anhydrous solvents were used as purchased from Sigma-Aldrich in AcroSeal® bottles.

Instrumentation $^1H$ NMR spectra were recorded on a 400 MHz Varian-Inova spectrometer, 500 MHz Varian-Inova spectrometer or a 600 MHz Varian-Inova spectrometer. $^{13}C$ NMR spectra were recorded on a 400 MHz Varian-Inova spectrometer (101 MHz), 500 MHz Varian-Inova spectrometer (126 MHz), or a 600 MHz Varian-Inova spectrometer (151 MHz). Chemical shifts (δ) are reported in parts per million (ppm). $^1H$ NMR spectra were standardised against the residual solvent peak $CDCl_3$ (δ=7.26 ppm); $CD_3OD$ (δ=3.31 ppm); $D_2O$ (δ=4.79 ppm); or internal TMS (δ=0.00 ppm). $^{13}C$ NMR spectra were standardised against the residual solvent peak $CDCl_3$ (δ=77.16 ppm); or $CD_3OD$ (δ=49.00 ppm). All $^{13}C$ NMR are $^1H$ decoupled. All NMR data is represented as follows: chemical shift (δ ppm), multiplicity (s=singlet, d=doublet, t=triplet, q=quartet, dd=double doublet, m=multiplet), coupling constant in Hertz (Hz), integration. Assignments were aided by homonuclear ($^1H$-$^1H$) (COSY) and heteronuclear ($^1H$-$^{13}C$) (HSQC, HMBC) two dimensional correlation spectroscopies. High-resolution mass spectrometry (HRMS) experiments were recorded on a Waters micromass LCT LC-Tof instrument using electrospray ionisation (ESI) in either positive or negative mode.

Example 1: Synthesis of Synthetic Pentasaccharides with Incorporated End Point Attached Linker at Reducing and Non-Reducing Ends Example 1.1: 5-Aminopentyl 2-deoxy-2-sulfamido-6-O-sulfo-α-D-glucopyranosyl-(1→4)-β-D-glucopyranosyluronic acid-(1→4)-2-deoxy-2-sulfamido-3,6-di-O-sulfo-α-D-glucopyranosyl-(1→4)-2-O-sulfo-α-L-idopyranosyluronic acid-(1→4)-2-deoxy-2-sulfamido-6-O-sulfo-β-D-glucopyranoside

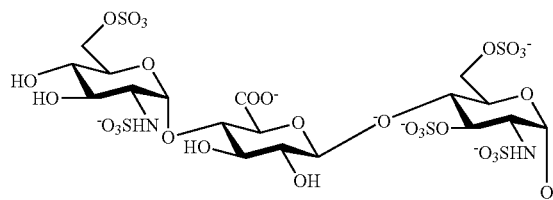
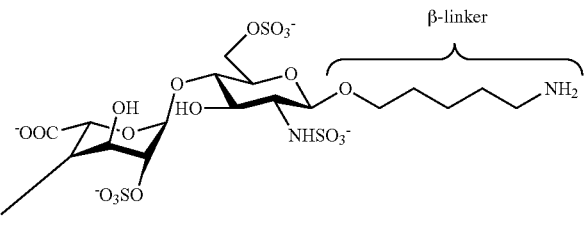

An overview of a synthetic route to this molecule is shown in FIG. 5.

(i) Synthesis of Monosaccharide Building Block B

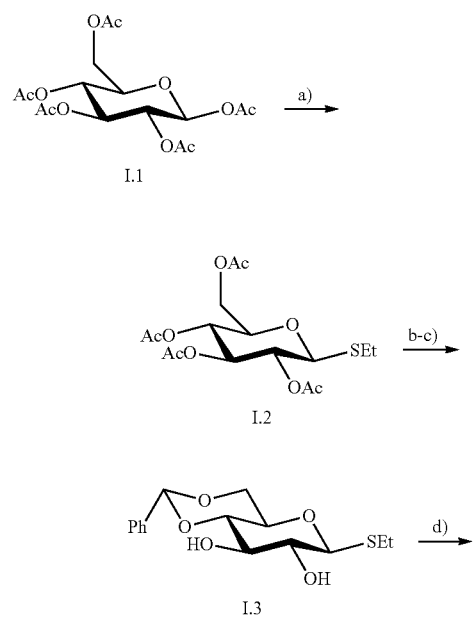

Scheme 1.

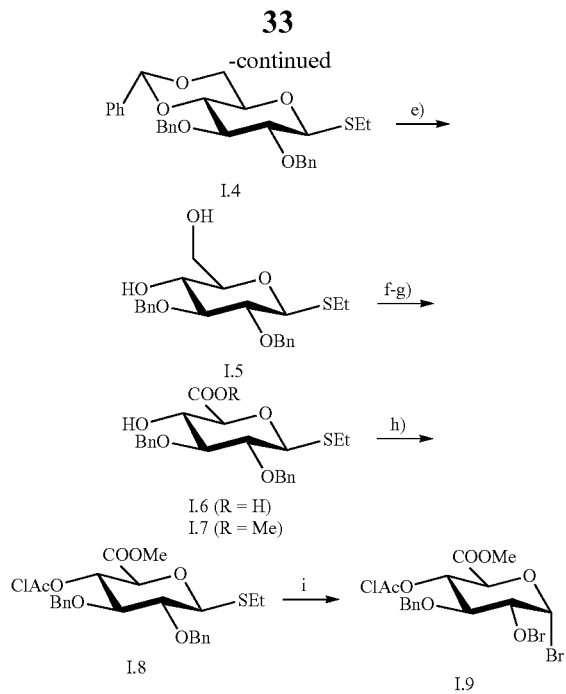

I.4

I.5

I.6 (R = H)
I.7 (R = Me)

I.8

I.9

Reagents and conditions: Synthesis of intermediate I.9.
a) EtSH, BF·Et₂O, dry CH₂Cl₂, 0° C. → rt, 1.5 h, 90%; b) CH₃ONa, CH₃OH, rt, 1 h, quant.; c) PhCH(OMe)₂, CSA, dry CH₃CN, rt, overnight, 75%; d) BnBr, NaH, DMF, 0° C. → rt, 2 h, 80%; e) AcOH 70%, 80° C., 1.5 h, 90%; f) TEMPO, BAIB, CH₂Cl₂/H₂O 3:1, rt, 1 h, 65%; g) (CH₃)₃SiCHN₂, dry CH₃OH/Toluene 1/1, 0° C., 5 min, 90%; h) ClCH₂COCl, dry Pyridine, dry CH₂Cl₂, 0° C., 15 min, 90%; i) Br₂, dry CH₂Cl₂, 0° C. → rt, 45 min, darkness, 90%;

Ethyl 4,6-O-benzylidene-1-thio-β-D-glucopyranoside, Intermediate I.3

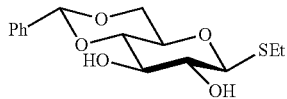

Commercially available, 1,2,3,4,6-Penta-O-acetyl-β-D-glucopyranose (I.1, 20.0 g, 0.05 mol, 1 eq) was dissolved in dry CH₂Cl₂ (100 mL, 0.5M) and ethanethiol (5.4 mL, 0.075 mol, 1.5 eq) was added under an atmosphere of nitrogen. The solution was cooled to 0° C. and boron trifluoride etherate (12.3 mL, 0.1 mol, 2 eq) was slowly added, allowing to the reaction to reach the room temperature. After 1 hour the TLC (cyclohexane/ethyl acetate 1:1) showed full conversion of starting material into product. The reaction was put on ice and quenched with TEA. Solvent was evaporated and the crude purified by flash chromatography using cyclohexane/ethyl acetate (80/20→60/40) giving intermediate I.2 (18.8 g, 0.048 mol, 96%) as a white solid (R_f (cyclohexane/ethyl acetate 6:4) 0.48. ¹H NMR in agreement with literature *J. Am. Chem. Soc.*, 2013, 135 (45), 16895-16903).

Intermediate I.2 was dissolved in methanol (100 mL, 0.5M) and sodium methoxide powder (0.5 g, 0.01 mol, 0.2 eq) was added. The reaction was stirred at room temperature overnight (TLC cyclohexane/ethyl acetate 1:1; dichloromethane/methanol 8:2). Then, reaction was neutralized with acidic resin DOWEX H⁺, filtered and concentrated. The resulting deprotected sugar was (10.7 g, 0.048 mol, 1 eq) dissolved in dry DMF (100 mL, 0.5 M), benzaldehyde dimethyl acetal (14.3 mL, 0.096 mol, 2 eq) and camphor-10-sulfonic acid (5.6 g, 0.024 mol, 0.5 eq) were added. The reaction was stirred overnight at 50° C., then put on ice and quenched with TEA until pH 7. Solvent was evaporated under reduced pressure and the crude purified by flash chromatography using cyclohexane/ethyl acetate (50/50→30/70) giving intermediate I.3 (12.6 g, 0.04 mol, 84%) as white solid (R_f (cyclohexane/ethyl acetate 1:1) 0.35. ¹H NMR (300 MHz, CDCl₃) δ 7.49 (dd, J=6.6, 3.2 Hz, 2H Ar), 7.37 (dd, J=5.1, 1.8 Hz, 3H Ar), 5.54 (s, 1H, CHPh), 4.47 (d, $J_{1,2}$=9.8 Hz, 1H, H1), 4.36 (dd, $J_{6,6'}$=10.0, $J_{5,6}$=4.6 Hz, 1H, H6), 3.84 (t, $J_{3,4}$=8.7 Hz, 1H, H4), 3.77 (t, $J_{6,6'}$=10.0 Hz, 1H, H6'), 3.60 (brt, $J_{3,4}$=8.7 Hz, 1H, H3), 3.56-3.46 (m, 2H, H2, H5), 2.77 (qd, J=7.5, 1.2 Hz, 2H, SCH₂CH₃), 1.33 (t, J=7.4 Hz, 3H, SCH₂CH₃) in agreement with the literature. *Carbohydrate Research*, 1992, 225, 229-245)

Ethyl 2,3-di-O-benzyl-4,6-O-1-thio-β-D-glucopyranoside, Intermediate I.5

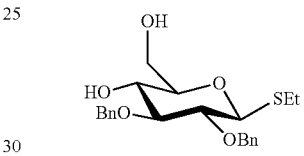

A solution of intermediate I.3 (4.28 g, 13.7 mmol, 1 eq) in dry DMF was cooled to 0° C. and NaH (60% in oil, 1.64 g, 68.5 mmol, 5 eq) was added. The suspension was stirred at 0° C. for 10 minutes, then benzyl bromide (6.3 mL, 54.8 mmol, 4 eq) was added. The reaction was stirred at room temperature for 1 hour. TLC (cyclohexane/ethyl acetate 1:1) showed the complete conversion of the starting material into the product. The reaction was put on ice and quenched with methanol (~15 mL) and water (~30 mL). The whole was diluted with EtOAc (250 mL) and extracted. The organic layer was washed with water (2×200 mL), dried on MgSO₄ and evaporated. The residue was taken up in EtOH and the resulting precipitate, intermediate I.4 (5.96 g, 12.1 mmol, 88%) was filtered and used in the next step without further purification (R_f (cyclohexane/ethyl acetate 9:1) 0.35. ¹H NMR in agreement with the literature *Carbohydrate Research*, 1992, 225, 229-245).

A solution of intermediate I.4 (2.4 g, 4.8 mmol, 1 eq) in 70% aqueous AcOH (25 mL) was refluxed at 80° C. for 4 hour (TLC cyclohexane/ethyl acetate 7:3). The solution was concentrated and the resulting residue was purified by automatic flash chromatography using cyclohexane/ethyl acetate (90/10→20/80) giving intermediate I.5 (1.6 g, 3.9 mmol, 81%) (R_f (cyclohexane/ethyl acetate 4:6) 0.46. ¹H NMR (300 MHz, CDCl₃) δ 7.48-7.04 (m, 10H, H Ar), 4.97 (d, J=11.6, 1H, CHHPh), 4.96 (d, J=10.2, 1H, CHHPh), 4.74 (d, J=10.2, 1 H, CHHPh), 4.71 (d, J=11.6, 1H, CHHPh), 4.52 (d, $J_{1,2}$=9.5 Hz, 1H, H1), 3.88 (ddd, J=12.0, 6.2, 3.6 Hz, 1H, H6), 3.75 (ddd, J=12.0, 7.0, 5.3 Hz, 1H, H6'), 3.57 (td, $J_{3,4}$=8.9, $J_{2,3}$=2.3 Hz, 1H, H3), 3.49 (t, $J_{3,4}$=8.9 Hz, 1H, H4), 3.41 (d, $J_{1,2}$=9.5 Hz, 1H, H2), 3.38-3.29 (m, 1H, H5), 2.77 (qd, J=7.4, 4.6 Hz, 2H, SCH₂CH₃), 1.33 (t, J=7.4 Hz, 3H, SCH₂CH₃) in agreement with the literature *Journal of Organic Chemistry*, 2013, 78(9), 4319-4328).

Methyl (ethyl 2,3-di-O-benzyl-1-thio-13-D-glucopyranosid)uronate, Intermediate I.7

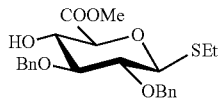

To a vigorously stirred solution of intermediate I.5 (1.6 g, 3.9 mmol, 1 eq) in $CH_2Cl_2/H_2O$ 2:1 (30 mL) TEMPO (0.2 g, 0.78 mmol, 0.2 eq) and BAIB (3.1 g, 9.7 mmol, 2.5 eq) were added. Stirring was allowed until TLC ($CH_2Cl_2$/$CH_3OH$ 9:1+1% AcOH) indicated complete conversion of the starting material to a lower running spot (~45 min). The reaction mixture was quenched by the addition of 10 ml $Na_2S_2O_3$ solution (10% in $H_2O$). The aqueous phase was acidified to pH 2 with HCl 1M and mixture was then extracted twice with $CH_2Cl_2$. The combined organic layers were dried on $MgSO_4$, filtered and concentrated. Flash column chromatography using cyclohexane/ethyl acetate (1:1+1% AcOH) afforded the pure glycuronic acid 1.6 (1.04 g, 2.48 mmol, 63%) as white foam ($R_f$ (cyclohexane/ethyl acetate (1:1+1% AcOH) 0.52. $^1H$ NMR in agreement with the literature Organic Letters, 2004, vol. 6, 13, 2165-2168).

Intermediate I.6 (1.03 g, 2.4 mmol, 1 eq) was dissolved in dry methanol/dry toluene 1:1 (12 mL, 0.2 M) and the solution was cooled to 0° C. $Me_3SiCHN_2$ 2M in diethyl ether-trimethylsilyl diazomethane- (1.5 mL, 2.9 mmol, 1.2 eq) was added. After 5 minutes TLC analysis (cyclohexane/ethyl acetate 1:1+1% AcOH) showed the formation of the product. The reaction was quenched by the addition of acetic acid and evaporated. The resulting residue was purified by automatic flash chromatography using cyclohexane/ethyl acetate 80/20 giving intermediate I.7 (0.945 g, 2.2 mmol, 90%) as a colorless oil ($R_f$ (cyclohexane/ethyl acetate 6:4) 0.48. $^1H$ NMR (400 MHz, $CDCl_3$) δ 7.41-7.25 (m, 10H, H Ar), 4.91 (d, J=10.5 Hz, 1H, CHHPh), 4.88 (s, 2H, CHHPh), 4.75 (d, J=10.5 Hz, 1H, CHHPh), 4.53 (d, $J_{1,2}$=9.5 Hz, 1H, H1), 3.90 (t, J=9.3 Hz, 1H, H4), 3.83 (s, 1H, H5), 3.81 (s, 1H, $COOCH_3$), 3.57 (t, $J_{2,3}$=8.8 Hz, 1H, H3), 3.41 (dd, 1H, $J_{1,2}$=9.5 Hz, $J_{2,3}$=8.8 Hz, H2), 2.91 (br s, 1H, OH), 2.85-2.69 (m, 2H, $SCH_2CH_3$), 1.33 (t, J=7.4 Hz, 3H, $SCH_2CH_3$) $^{13}C$ NMR (101 MHz, $CDCl_3$) δ 169.7 (COOMe), 138.5 (CqBn), 137.9 (CqBn), 128.6-128.0 (Ar), 86.1 (C1), 85.2 (C3), 80.7 (C2), 77.7 (C5), 75.73 ($CH_2Ph$), 75.71 ($CH_2Ph$), 72.1 (C4), 52.9 ($COOCH_3$), 25.4 ($SCH_2$), 15.2 ($CH_3$) in agreement with the literature Organic Letters, 2004, vol. 6, 13, 2165-2168).

Methyl (2,3-di-O-benzyl-4-O-chloroacetyl-α-D-glucopyranosyl bromide)uronate, Intermediate I.9

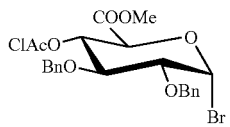

A solution of intermediate I.7 (0.800 g, 1.85 mmol, 1 eq) in dry $CH_2Cl_2$ (18 mL, 0.1 M), was cooled to 0° C. and dry pyridine (3.0 mL, 37.0 mmol, 20 eq) and chloroacetyl chloride (0.3 mL, 3.7 mmol, 2 eq) were added. The reaction was stirred at 0° C. for 10 minutes, then TLC (cyclohexane/ethyl acetate 6:4) showed the full conversion of the starting material into the product. The reaction was diluted with $CH_2Cl_2$ and washed with HCl 1 M, sat. aq. $NaHCO_3$ and Brine. The organic phase was dried on $MgSO_4$, filtered and evaporated. The crude was purified by flash chromatography using cyclohexane/ethyl acetate 8:2 afforded the pure intermediate I.8 (0.860 g, 1.68 mmol, 91%) as a white solid ($R_f$ (cyclohexane/ethyl acetate 8:2) 0.38. $^1H$ NM R and $^{13}C$ NMR in agreement with the literature Carbohydrate Research, 2003, 338, 23, 2605-2609).

To a solution of intermediate I.8 (860 mg, 1.68 mmol, 1 eq) in dry $CH_2Cl_2$ (17 mL, 0.1 M) bromine (0.095 mL, 1.85 mmol, 1.1 eq) was added. The reaction was stirred in the darkness at room temperature for 1 hour, then quenched with cyclohexene and evaporated under vacuum. The crude was purified by flash chromatography using cyclohexane/ethyl acetate 8:2 afforded the pure intermediate I.9 (822 mg, 1.55 mmol, 92%) as an oil ($R_f$ (cyclohexane/ethyl acetate 8:2) 0.39 $^1H$ NMR (400 MHz, $CDCl_3$) β 7.39-7.27 (m, 10H, H Ar), 6.32 (d, $J_{1,2}$=3.8 Hz, 1H, H1), 5.13 (dd, $J_{4,5}$=10.4, $J_{3,4}$=9.2 Hz, 1H, H4), 4.90 (d, J=11.8 Hz, 1H, CHHPh), 4.72 (d, J=8.4 Hz, 2H, $CH_2Ph$), 4.67 (d, J=11.8 Hz, 1H, CHHPh), 4.47 (d, $J_{4,5}$=10.4 Hz, 1H, H5), 4.02 (t, $J_{2,3}$=$J_{3,4}$=9.2 Hz, 1H, H3), 3.85 (d, J=14.9 Hz, 1H, $CH_2Cl$), 3.72 (d, J=14.9 Hz, 1H, CH'$_2$Cl), 3.71 (s, 3H, $COOCH_3$), 3.61 (dd, $J_{2,3}$=9.2, $J_{1,2}$=3.8 Hz, 1H, H2) $^{13}C$ NMR (101 MHz, $CDCl_3$) δ 167.2 (COOMe), 166.3 ($COCH_2Cl$), 138.1 (CqBn), 136.9 (CqBn), 128.8-128.1 (Ar), 88.9 (C1), 78.7 (C2), 78.4 (C3), 75.8 ($CH_2Ph$), 73.4 ($CH_2Ph$), 72.1 (C5), 71.2 (C4), 53.3 ($COOCH_3$), 40.4 ($ClCH_2$) ESI-MS: calc. for $C_{23}H_{25}BrClO_7$ [M]: 527.05, found 550.60 [M+Na$^+$]).

(ii) Synthesis of Monosaccharide Building Block C

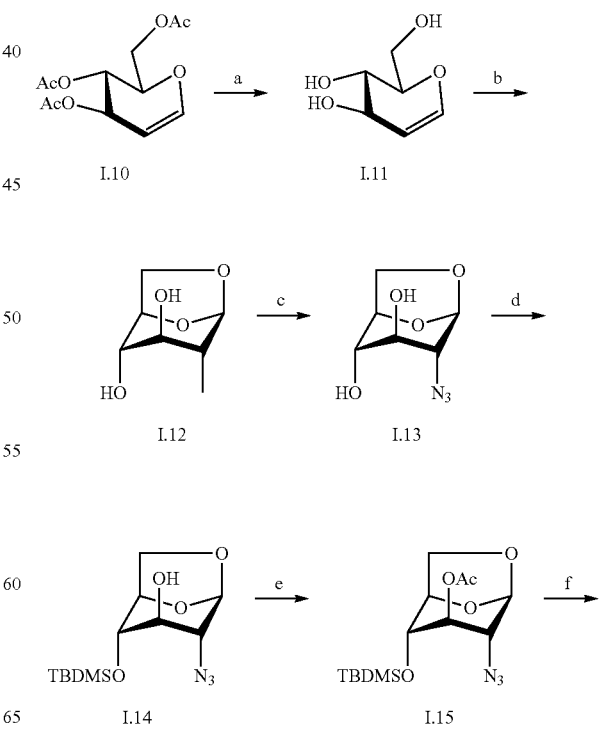

Scheme 2.

-continued

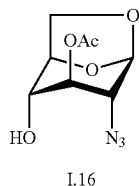

I.16

Reagents and conditions: Synthesis of intermediate I.16 a) CH₃OH/H₂O/TEA 10:10:1, rt, 1.5 h, quant.; b) Step I: Bis(tributylstannyl) oxide, dry CH₃CN, molecular sieves 3 Å, 80° C., 3 h, Step II: Iodine, rt, 1 h, 65%; c) NaN₃, DMF/H₂O 9:1, 120° C., overnight, 70%; d) TBDMSCl, Imidazole, DMF, rt, overnight, 65%; e) Ac₂O, Py, rt, overnight, 90%; f) AcOH 70%, 80° C., overnight, 75%.

1,6-Anhydro-2-deoxy-2-iodo-β-D-glucose, Intermediate I.12

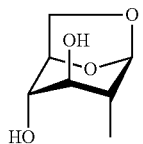

A solution of commercially available tri-O-acetyl-D-glucal (1.10, 25.0 g, 91.8 mmol, 1 eq) in 10:10:1 CH₃OH/H₂O/TEA (210 mL) was stirred for 2 hours at room temperature. TLC (CH₂Cl₂/CH₃OH 9:1) showed the complete conversion of the starting material into intermediate I.11. The solution was concentrated under vacuum and dried at the Schlenck overnight. This crude was used directly in the next step without further purification.

Intermediate I.11 was treated with bis-tri-n-butyltin oxide (37.4 mL, 73.4 mmol, 0.8 eq) and freshly activated powdered 3 Å molecular sieves in refluxing dry acetonitrile for 3 hours under N₂. The mixture was cooled to 5° C. and iodine (35 g, 137.7 mmol, 1.5 eq) was added, stirring the mixture for 2 hour at room temperature. (TLC CH₂Cl₂/CH₃OH 9:1) The mixture was filtered through Celite and solvent concentrated. Saturated aqueous Na₂S₂O₃ and cyclohexane (1:1, 300 mL) were added to the crude and the biphasic mixture was stirred overnight. The aqueous phase was extracted with ethyl acetate (500 mL×3). The organic layer was dried over MgSO₄, filtered and concentrated. Purification via chromatography using toluene/acetone (95/5→60/40) gave 1.12 (11.7 g, 43.0 mmol, 58%) as white solid (R$_f$ (toluene/acetone 7:3) 0.42. ¹H NMR (300 MHz, DMSO-d₆) δ 5.61 (s, 1H, H1), 5.51 (d, J=4.2 Hz, 1H, OH-3), 5.18 (d, J=4.2 Hz, 1H, OH-4), 4.42 (d, J$_{5,6'}$=5.9 Hz, 1H, H5), 4.01 (d, J$_{6,6'}$=7.0 Hz, 1H, H6), 3.92-3.96 (m, 1H, H3), 3.82 (brs, 1H, H2), 3.52 (dd, J$_{5,6'}$=5.9 Hz, J$_{6,6'}$=7.0 Hz, 1H, H6'), 3.44-3.47 (m, 1H, H4) in accordance with literature Macromolecules 2002, 35, 3402-3412).

1,6-Anhydro-2-azido-2-deoxy-4-O-(tert-butyldimethylsilyl)-β-D-glucose, intermediate I.14

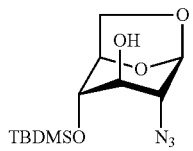

Intermediate I.12 (4.0 g, 15.0 mmol, 1 eq) was dissolved in DMF/H₂O 9:1 (30 mL, 0.5 M) and sodium azide (3.9 g, 60.0 mmol, 4 eq) was added. The reaction was stirred at 120° C. for 4 hours. TLC (toluene/acetone 7:3) showed complete conversion of the starting material into the product. The solvent was evaporated and residue was purified via chromatography using toluene/acetone (95/5→60/40) giving 1.13 (2.18 g, 11.6 mmol, 78%) as a white solid (R$_f$ (toluene/acetone 7:3) 0.39 ¹H NMR (300 MHz, CDCl₃) δ 5.51 (s, 1H, H1), 4.58 (d, J$_{5,6}$=5.4 Hz, 1H, H5), 4.22 (d, J$_{6,6'}$=7.6 Hz, 1H, H6), 3.90 (dd, J=6.7, 1.8 Hz, 1H, H4), 3.80 (dd, J$_{6,6'}$=7.6, J$_{5,6}$=5.4 Hz, 1H, H6'), 3.66 (d, J=10.4 Hz, 1H, H3), 3.51 (s, 1H, H2), 2.59 (d, J=10.4 Hz, 1H, OH), 2.42 (d, J=7.1 Hz, 1H, OH) in accordance with literature, *Tetrahedron Letters,* 2001, 42, 6487-6489).

To a solution of intermediate I.13 (2.07 g, 11.1 mmol, 1 eq) in DMF (20 mL, 0.5 M) were added imidazole (2.0 g, 13.3 mmol, 1.2 eq) and tert-butyldimethylsilyl chloride (1.5 g, 22.2 mmol, 2 eq). After being stirred overnight at room temperature, the solvent was evaporated in vacuo, and the crude was purified via chromatography using cyclohexane/ethyl acetate (95/5→60/40) giving intermediate I.14 (2.25 g, 7.4 mmol, 67%) as a colorless oil (R$_f$ (cyclohexane/ethyl acetate 7:3) 0.4 ¹H NMR (300 MHz, CDCl₃) δ 5.49 (s, 1H, H1), 4.44 (d, J$_{5,6'}$=5.4 Hz, 1H, H5), 4.04 (d, J$_{6,6}$=7.5 Hz, 1H, H6), 3.80-3.74 (m, 1H, H3), 3.71 (dd, J$_{6,6'}$=7.5 Hz, J$_{5,6}$=5.4 Hz, 1H, H6'), 3.65 (s, 1H, H4), 3.13 (s, 1H, H2), 0.93 (s, 9H, t-Bu), 0.13 (s, 3H, CH₃), 0.12 (s, 3H, CH₃)).

1,6-anhydro-3-O-acetyl-2-azido-2-deoxy-β-D-glucose, Intermediate I.16

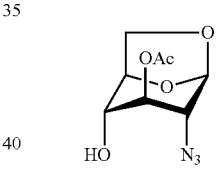

Intermediate I.14 (7.29 g, 24.2 mmol, 1 eq) was dissolved in pyridine (100 mL, 025 M) and acetic anhydride (22 mL, 10 eq) was added. The reaction was stirred overnight at room temperature, then the excess of acetic anhydride was quenched with methanol and the mixture was evaporated. The crude was purified via chromatography using cyclohexane/ethyl acetate (95/5→60/40) giving intermediate I.15 (7.68 g, 22.3 mmol, 92%) as a white solid (R$_f$(cyclohexane/ethyl acetate 7:3) 0.44. ¹H NMR and ¹³C NMR in accordance with the literature *J. Org. Chem.* 1997, 62, 992-998).

Intermediate I.15 (3.0 g, 8.7 mmol, 1 eq) was dissolved in 70% aqueous acetic acid (120 mL) and heated at 80° C. overnight. TLC (cyclohexane/ethyl acetate 6:4) showed the complete conversion of the starting material into the product. The solvent was evaporated and the crude was purified by automatic chromatography using cyclohexane/ethyl acetate (95/5→60/40) giving intermediate I.16 (1.58 g, 6.9 mmol, 80%) as an oil (R$_f$ (cyclohexane/ethyl acetate 4:6) 0.35 ¹H NMR (400 MHz, CDCl₃) δ 5.43 (s, 1H, H1), 4.84 (d, J=1.6 Hz, 1H, H3), 4.58 (d, J$_{5,6}$=5.5 Hz, 1H, H5), 4.10 (dd, J$_{6,6'}$=7.6, J$_{5,6}$=0.8 Hz, 1H, H6), 3.81 (dd, J$_{6,6'}$=7.6, J$_{5,6'}$=5.5 Hz, 1H, H6'), 3.61 (s, 1H, H4), 3.47 (brs, 1H, H2), 2.11 (s, 3H, CH₃CO) ¹³C NMR (101 MHz, CDCl₃) δ 169.9 (CO), 100.0 (C1), 76.2 (C5), 72.2 (C3), 68.7 (C4), 65.1 (C6), 59.4 (C2), 21.1 (CH₃CO) ESI-MS: calc. for C8H11N3O5

[M]: 229.07, found 251.23 [M+Na+]; 479.90 [2M+Na+] 1H NMR and 13C NMR in accordance with the literature J. Org. Chem. 1997, 62, 992-998).

(iii) Synthesis of Monosaccharide Building Block A

Scheme 3.

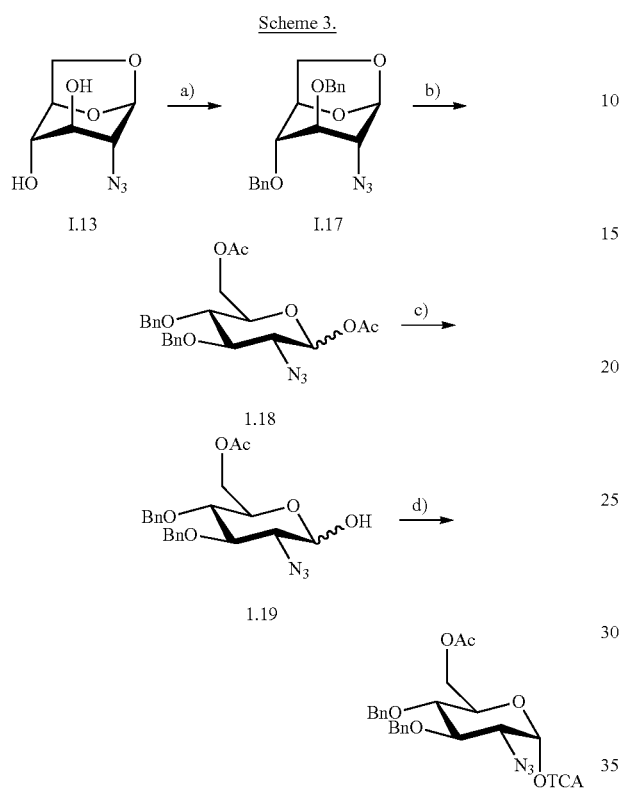

Reagents and conditions: Synthesis of intermediate I.20. a) BnBr, NaH, DMF, 0° C. → rt, 1 h, 85%; b) Ac₂O, TBSOTf, 0° C., 10′, 85%; c) EDA, AcOH, THF, rt, overnight, 75%; d) Cl₃CCN, DBU, dry CH₂Cl₂, 3 h, rt, 85%.

1,6-O-diacetyl-2-azido-3,4-di-O-benzyl-2-deoxy-glucopyranoside, Intermediate I.18

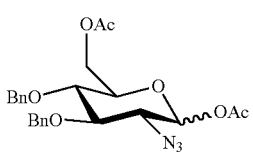

Intermediate I.13 (500 mg, 2.7 mmol, 1 eq) was dissolved in dry DMF (13.5 mL, 0.2 M) and the solution was cooled to 0° C. NaH (324 mg, 13.5 mmol, 5 eq) was added followed by the addition 10 minutes later of BnBr (1.3 mL, 10.8 mmol, 4 eq). After 30 minutes TLC (cyclohexane/ethyl acetate 4:6) showed the formation of the product. Reaction was quenched with methanol and water. The mixture was poured into a separating funnel and extracted with CH₂Cl₂ (×3). The collected organic phase was dried on MgSO₄ and evaporated. The crude was purified by automatic chromatography using cyclohexane/ethyl acetate (95/5→70/30) giving intermediate I.17 (846 mg, 2.3 mmol, 85%) as an oil (R$_f$ (cyclohexane/ethyl acetate 3:7) 0.55 ¹H NMR (400 MHz, CDCl₃) δ 7.42-7.28 (m, 10H, H Ar), 5.50 (s, 1H, H1), 4.64-4.62 (m, 1H, H5), 4.61-4.49 (m, 4H, 2 CH₂Ph), 4.02 (dd, J$_{6,6'}$=7.3, J$_{6,5}$=1.1 Hz, 1H, H6), 3.73 (dd, J$_{6,6'}$=7.3, J$_{6',5}$=5.9 Hz, 1H, H6'), 3.68-3.65 (m, 1H, H4), 3.39 (br s, 1H, H3), 3.28 (s, 1H, H2) ¹³C NMR (101 MHz, CDCl₃) δ 137.5 (CqBn), 137.4 (CqBn), 128.7 to 127.9 (Ar), 100.7 (C1), 76.4 (C4), 76.0 (O3), 74.5 (C5), 72.5 (CHPh), 71.5 (CHPh), 65.5 (C6), 60.0 (C2)).

Intermediate I.17 (846 mg, 2.3 mmol, 1 eq) was dissolved in acetic anhydride (5 mL, 0.5 M) and the solution was cooled to 0° C. TBSOTf was added and reaction was checked in TLC (cyclohexane/ethyl acetate 8:2) after 10′ showing the formation of the product. Reaction was quenched with TEA and concentrated in vacuo. The crude was purified by automated flash chromatography using cyclohexane/ethyl acetate (90:10→60:40) obtaining intermediate I.18 in α/β mixture (930 mg, 2.0 mmol, 87%) as a white foam (R$_f$ (cyclohexane/ethyl acetate 8:2) 0.35 ¹H NMR (400 MHz, CDCl₃) δ 7.44-7.21 (m, 10H, H Ar), 6.23 (d, J$_{1,2}$=3.6 Hz, 0.8H, H1α), 5.48 (d, J$_{1,2}$=8.3 Hz, 0.2H, H1(β), 4.91-4.94 (m, 2H, CH₂Ph), 4.88 (d, J=10.7 Hz, 1H, CHPh), 4.60 (d, J=10.8 Hz, 1H, CHPh), 4.31-4.18 (m, 2H, H6), 3.97 (dd, J$_{2,3}$=10.3, J$_{1,2}$=8.9 Hz, 1H, H3), 3.92 (dd, J=10.1, J=3.1 Hz, 1H, H5), 3.69-3.53 (m, 2H, H2, H4), 2.16 (s, 3H CH₃CO), 2.04 (s, 3H, CH₃CO) ¹³C NMR (101 MHz, CDCl₃) δ 170.7 (C=O), 168.9 (C=O), 137.6 (CqBn), 137.3 (CqBn), 128.7 to 128.2 (Ar), 92.5 (C1β), 90.5 (C1α), 80.7 (C3), 77.3 (C4), 75.8 (CH₂Ph), 75.4 (CH₂Ph), 71.4 (C5), 62.9 (C2), 62.4 (C6), 21.0 (CH₃CO), 20.9 (CH₃CO) ESI-MS: calc. for C₂₄H₂₇N₃O₇ [M]: 469.18, found 492.04 [M+Na⁺], 961.22 [2M+Na⁺]).

6-O-Acetyl-2-azido-3,4-di-O-benzyl-2-deoxy-α-D-glucopyranosyl trichloroacetimidate, Intermediate I.20

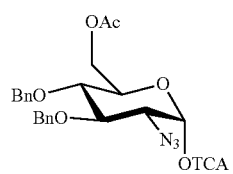

Intermediate I.18 (400 mg, 0.85 mmol, 1 eq) was dissolved in THF (8.5 mL, 0.1 M) and ethylediamine (87 μl, 1.3 mmol, 1.5 eq) and acid acetic (74 μl, 1.3 mmol, 1.5 eq) were added. Reaction was stirred at room temperature overnight, then it was diluted with CH₂Cl₂ and washed with HCl 1M. The aqueous phase was extracted twice with CH₂Cl₂. The combined organic layers were washed with NaHCO₃ aq sat and Brine, dried over MgSO₄ and evaporated. The crude was purified by automatic chromatography (cyclohexane/ethyl acetate 85/15→40/60) giving intermediate I.19 (347 mg, 0.81 mmol, 95%) as a white vax (R$_f$ (cyclohexane/ethyl acetate 6:4) 0.40. ¹H NMR (400 MHz, CDCl₃) δ 7.41-7.27 (m, 10H, H Ar), 5.30 (brs, 1H, H1α), 5.38-5.31 (m 3H, CH₂Ph, CHPh), 4.62-4.57 (m, 2H, CHPh, H113), 4.34 (dd, J$_{6a,6b}$=12.0, J$_{6a,5}$=2.2 Hz, H6a), 4.21 (dd, J$_{6a,6b}$=12.0, J$_{6b,5}$=4.4 Hz, 1H, H6b), 4.12 (ddd, J$_{5,4}$=10.2, J$_{6b,5}$=4.4, J$_{6a,5}$=2.2 Hz, 1H, H5), 4.05 (dd, J$_{2,3}$=10.2, J$_{3,4}$=8.9 Hz, 1H, H3), 3.56 (dd, J=9.9, J$_{3,4}$=8.9 Hz, 1H, H4), 3.43 (dd, J$_{2,3}$=10.2, J$_{1,2}$=3.4 Hz, 1H, H2), 2.05 (s, 3H, CH₃CO) ¹³C NMR (101 MHz, CDCl₃) δ 170.9 (C=O), 137.7 (CqBn), 137.6 (CqBn), 128.7 to 128.1 (Ar), 96.3 (C1β), 92.2 (C1α), 80.2 (C3), 78.1 (C4), 75.7 (CH$_2$Ph), 75.2 (CH$_2$Ph), 69.4 (C5), 64.1 (C2), 62.9 (C6), 21.0 (CH$_3$CO)).

Trichloroacetonitrile (0.812 mL, 8.1 mmol, 10 eq) and DBU (24 μL, 0.162 mmol, 0.2 eq) were added to a solution of intermediate I.19 (347 mg, 0.81 mmol, 1 eq) in dry CH$_2$Cl$_2$ (8 mL, 0.1 M), and the reaction mixture was stirred for 2 h under Ar at room temperature. After concentration, the residue was purified by flash chromatography eluted with cyclohexane/ethyl acetate (8:2+1% TEA) to give the 1.20 (439 mg, 95%) as 90% alpha anomer (R$_f$(cyclohexane/ethyl acetate 6:4) 0.52. $^1$H NMR (400 MHz, CDCl$_3$) δ 8.74 (s, 1H, NHCCl$_3$), 7.43-7.27 (m, 10H, Ar), 6.41 (d, 1H, $J_{1,2}$=3.5 Hz, H1α), 5.63 (d, $J_{1,2}$=8.4 Hz, H1β), 4.95 (s, 2H, CH$_2$Ph), 4.88 (d, J=10.7 Hz, 1H, CHPh), 4.61 (d, J=10.8 Hz, 1H CHPh), 4.31 (dd, $J_{6a,6b}$=12.2, $J_{6a,5}$=2.3 Hz, 1H, H6a), 4.24 (dd, $J_{6a,6b}$=12.2, $J_{6b,5}$=4.0 Hz, 1H, H6b), 4.10-4.01 (m, 2H, H-5, H-3), 3.74-3.64 (m, 2H, H-2, H-4), 2.02 (s, 3H, CH$_3$CO) $^{13}$C NMR (400 MHz, CDCl$_3$) δ 170.6 (C=O), 160.8 (C=NH), 137.6 (CqBn), 137.3 (CqBn), 128.7 to 128.2 (Ar), 94.7 (01), 80.3 (C5 or C3), 77.4 (C2 or C4), 75.8 (CH$_2$Ph), 75.5 (CH$_2$Ph), 71.9 (C5 or C3), 63.2 (C2 or C4), 62.4 (C6), 20.9 (CH$_3$CO) in accordance with literature *Carbohydrate Research* 2003, 338, 1369-1379).

(iv) Synthesis of Monosaccharide Building Block D

Scheme 4

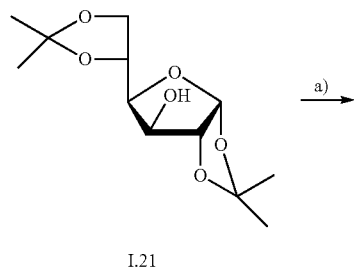

I.21

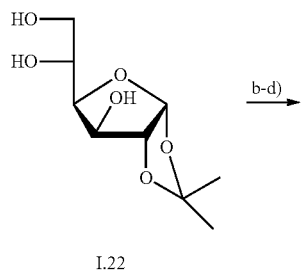

I.22

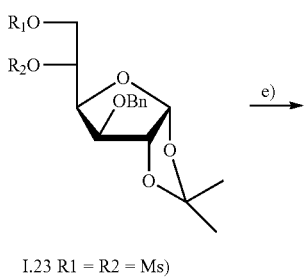

I.23 R1 = R2 = Ms)
I.24 (R1 = Ac, R2 = Ms)

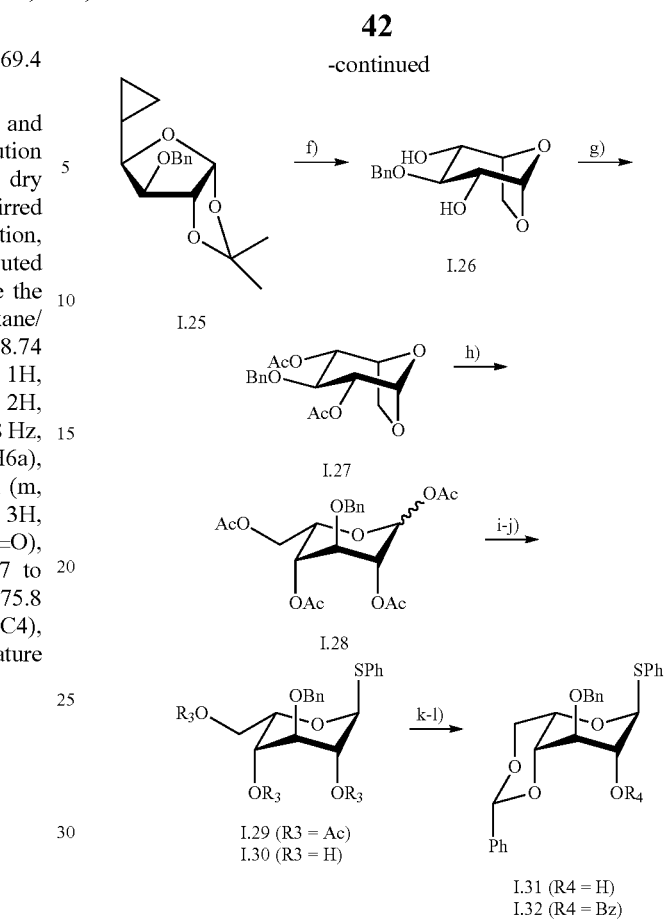

I.25

I.26

I.27

I.28

I.29 (R3 = Ac)
I.30 (R3 = H)

I.31 (R4 = H)
I.32 (R4 = Bz)

Reagents and conditions: Synthesis of intermediate I.32. a- NaH, BnBr, THF, 0° C. → rt, b) 2 hours; H$_2$O/AcOH, 40° C., overnight, 79% (2 steps); c) MsCl, pyridine, 0 → 4° C., overnight, 98%; d) KOAc, 18-crown-6, MeCN, 92° C., 24 hours, 89%; e) CH$_2$Cl$_2$, $^t$BuOK, , $^t$BuOH, 0° C., overnight, 89%; f) Dioxane, 2M H$_2$SO$_4$, 100° C., overnight, 45%; g) Pyridine, Ac$_2$O, 0° C. → rt, overnight. 91% of 27; h) TMSOTf, CH$_2$Cl$_2$, Ac$_2$O, 0° C., 20 minutes, 87%; i) BF$_3$•Et$_2$O, HSPh, CH$_2$Cl$_2$, 0° C. → rt, 4 hours, 90%; j) MeOH, NaOMe, rt, overnight, 92%; k) CSA, DMF, Naphthyl dimethyl acetal, 60° C., overnight, 84%; l) BzCl, pyridine, 0° C. → rt overnight, 89%.

3-O-benzyl-1,2-O-isopropylidene-α-D-glucofuranose, Intermediate I.22

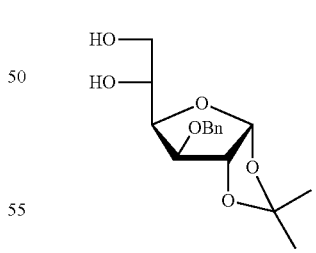

Commercially available diacetone glucose 1.21 (20 g, 76.84 mmol, 1 eq) was dissolved in dry THF (150 mL) and cooled to 0° C. 60% NaH (5.1 g, 126.8 mmol, 1.65 eq) was added and the mixture was stirred for 30 minutes. BnBr (13.7 mL, 115.3 mmol, 1.5 eq in 14 mL dry DMF) was then added slowly and the mixture was warmed back to rt and stirred for 2 hours when TLC showed no remaining starting material. The mixture was cooled to 0° C. and MeOH (264 mL, 6500 mmol, 85 eq) was added slowly to quench the reaction, stirring on ice for an additional 10 minutes. The solvents were concentrated and the resulting residue was dissolved in $CH_2Cl_2$ and washed sequentially with $H_2O$ and brine. The aqueous extracts were re-extracted with additional $CH_2Cl_2$. The combined organic layer was washed with brine and then dried on $MgSO_4$, filtered and concentrated to yield a yellow syrup which was used directly without further purification. The crude was dissolved in a $H_2O$:AcOH solution (96 mL 1:1 v/v) and stirred at 45° C. for 4.5 hours, before heating to 50° C. for 1 hour. Conversion had not yet completed and an additional 48 mL $H_2O$ was added and the reaction was stirred overnight at 40° C. Afterwards the reaction was neutralized by the careful addition of sat. aq. $K_2CO_3$ solution and transferred to a separating funnel and extracted three times with $CH_2Cl_2$. The combined organic layer was washed twice with brine and dried on $Na_2SO_4$, filtered and concentrated to yield a yellow syrup which was purified by column chromatography (Tol/EtOAc 8-66%) to yield intermediate I.22 (18.33 g (59.06 mmol, 77% over 2 steps) as a yellow syrup) ($R_f$: (Tol/EtOAc 2:1 v/v) 0.15. $^1$H NMR (500 MHz, CDCl$_3$) δ 7.37-7.27 (m, 5H, Ar), 5.91 (d, J=3.8 Hz, 1H, H1), 4.70 (d, J=11.8 Hz, 1H, PhCH$_2$), 4.60 (d, J=3.8 Hz, 1H, H2), 4.57 (d, J=11.7 Hz, 1H, PhCH$_2$), 4.13-4.08 (m, 2H, H3, H4), 4.04-3.98 (m, 1H, H5), 3.79 (dd, J=11.7, 3.3 Hz, 1H, H6a), 3.67 (dd, J=11.5, 5.5 Hz, 1H, H6b), 2.95 (d, J=5.9 Hz, 1H, OH), 2.87-2.81 (m, 1H, OH), 1.47 (s, 3H, iPr), 1.30 (s, 3H, iPr) $^{13}$C NMR (126 MHz, CDCl$_3$) 137.37 (Ar), 128.70 (Ar), 128.18 (Ar), 127.86 (Ar), 111.84 (C(CH$_3$)$_2$), 105.18 (C1), 82.20 (C2), 81.99 (C3), 80.01 (C4), 72.24 (PhCH$_2$), 69.18 (C5), 64.37 (C6), 26.77 ($^i$Pr), 26.26 ($^i$Pr)).

3-O-Benzyl-1,2-O-isopropylidene-5,6-di-O-methanesulfonyl-α-D-glucofuranose, Intermediate I.23

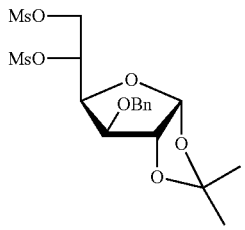

Intermediate I.22 (18.33 g, 58.97 mmol, 1 eq) was dissolved in dry pyridine (88 mL) and cooled to 0° C., after stirring at that temperature for 5 minutes MsCl (11 mL, 141.53 mmol, 2.4 eq) was added slowly. The mixture was stirred at that temperature for 30 minutes and then warmed to 4° C. and stirred overnight. The following day additional MsCl (2 mL, 25.88 mmol, 0.44 eq) was added and the reaction remained stirring at 4° C. for 2 hours before being poured onto $H_2O$ (500 mL, 50° C.) leading to the formation of a precipitate. The mixture was allowed to cool to rt and stood overnight. The solids were collected by filtration, washed with $H_2O$ and then coevaporated twice with toluene and dried to give intermediate I.23 (26.2 g, 58.68 mmol, 98%) as a white solid (Rf: (Cyclohexane/EtOAc, 3:2 v/v) 0.31. $^1$H NMR (500 MHz, CDCl$_3$) δ 7.40-7.29 (m, 5H, Ar), 5.88 (d, J=3.6 Hz, 1H, H1), 5.24 (ddd, J=7.6, 5.7, 2.1 Hz, 1H, H5), 4.69-4.59 (m, 4H, H2, PhCH$_2$, H6a), 4.44 (dd, J=11.9, 5.7 Hz, 1H, H6b), 4.40 (dd, J=7.4, 3.1 Hz, 1H, H4), 4.13 (d, J=3.2 Hz, 1H, H3), 3.08 (s, 3H, OMs), 3.00 (s, 3H, OMs), 1.49 (s, 3H, iPr), 1.31 (s, 3H, iPr) $^{13}$C NMR (126 MHz, CDCl$_3$) δ 137.02 (Ar), 128.68 (Ar), 128.33 (Ar), 112.60 ((C(CH$_3$)$_2$), 105.41 (C1), 81.61 (C2), 81.14 (C3), 78.18 (C4), 74.48 (C5), 72.57 (PhCH$_2$), 69.07 (C6), 39.20 (OMs), 37.61 (OMs), 26.97 ($^i$Pr), 26.34 ($^i$Pr)).

6-O-Acetyl-3-O-benzyl-1,2-O-isopropylidene-5-O-methanesulfonyl-α-D-glucofuranose, Intermediate I.24

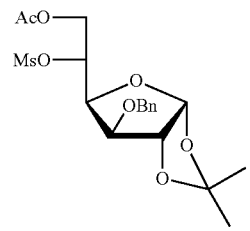

Intermediate I.23 (19.7 g, 42.23 mmol, 1 eq), dried KOAc (41.44 g, 422.3 mmol, 10 eq) and 18-Crown-6 (1.11 g, 4.22 mmol, 0.1 eq) were dissolved in MeCN (350 mL) and heated at 92° C. for 24 hours when TLC showed consumption of starting material. The reaction mixture was cooled back to rt, filtered and rinsed with additional MeCN. The filtrate was concentrated and the resulting residue was dissolved in $CH_2Cl_2$ and washed twice with water. The combined aqueous extracts were extracted with additional $CH_2Cl_2$ and the combined organic layers were dried on $MgSO_4$, filtered and concentrated. The resulting solid was recrystallized from EtOH to yield crystals, which were isolated by filtration and washed three times with chilled EtOH to yield intermediate I.24 (16.1 g, 37.4 mmol, 89%) as white crystals ($R_f$: 0.61 (Cyclohexane/EtOAc, 3:2 v/v) $^1$H NMR (500 MHz, CDCl$_3$) δ 7.39-7.28 (m, 5H, Ar), 5.89 (d, J=3.6 Hz, 1H, H1), 5.25 (ddd, J=7.8, 6.5, 2.2 Hz, 1H, H5), 4.73-4.58 (m, 4H, H2, PhCH$_2$, H6a), 4.36 (dd, J=7.8, 3.1 Hz, 1H, H3), 4.24 (dd, J=12.7, 6.5 Hz, 1H, H6b), 4.10 (dd, J=3.2, 0.6 Hz, 1H, H4), 3.02 (s, 3H, OMs), 2.10 (s, 3H, COCH$_3$), 1.50 (s, 3H, iPr), 1.31 (s, 3H, iPr) $^{13}$C NMR (126 MHz, CDCl$_3$) 170.44 (COCH$_3$), 137.23 (Ar), 128.63 (Ar), 128.18 (Ar), 128.16 (Ar), 112.42 (C(CH$_3$)$_2$), 105.44 (C1), 81.63 (C2), 81.23 (C4), 78.42 (C3), 75.57 (C5), 72.43 (PhCH$_2$), 63.62 (C6), 39.10 (OMs), 27.00 (COCH$_3$), 26.41 (iPr), 20.92 (iPr)).

5,6-Anhydro-1,2-O-isopropylidene-3-O-benzyl-β-L-idofuranose, Intermediate 1.25

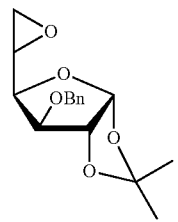

Intermediate I.24 (16.1 g 37.43 mmol, 1 eq) was dissolved in dry $CH_2Cl_2$ (170 mL) and dried $^t$BuOK (8.4 g, 74.86 mmol, 2 eq) and $^t$BuOH (80.5 mL, 842.18 mmol, 22.5 eq) were added at 0° C. and the mixture was stirred overnight at that temperature. The following day additional dried $^t$BuOK (1.5 g, 13.34 mmol, 0.36 eq) was added and the reaction was stirred for an additional 4 hours before being diluted with H₂O and CH₂Cl₂ and transferred into a conical flask. The mixture was carefully neutralised with the slow addition of AcOH. The layers were then separated and the aqueous layer extracted once with CH₂Cl₂. The combined organic layers were washed once with brine, dried on MgSO₄, filtered and concentrated. The resulting brown oil was purified by chromatography over a short plug of silica with Cyclohexane/EtOAc (3:2) giving intermediate I.25 (9.76 g (33.39 mmol, 89%) as a yellow syrup (R$_f$: (Cyclohexane/EtOAc, 3:2 v/v) 0.6. ¹H NMR (500 MHz, CDCl₃) δ 7.40-7.29 (m, 5H, Ar), 6.00 (d, J=3.3 Hz, 1H, H1), 4.75 (dd, J=12.2, 1.8 Hz, 1H, PhCH₂), 4.65-4.62 (m, 1H, H2), 4.52 (dd, J=12.2, 1.8 Hz, 1H, PhCH₂), 3.98-3.96 (m, 1H, H3), 3.84-3.78 (m, 1H, H4), 3.30-3.24 (m, 1H, H5), 2.79-2.74 (m, 1H, H6a), 2.56-2.53 (m, 1H, H6b), 1.45 (s, 3H, $^i$Pr), 1.32 (s, 3H, $^i$Pr) ¹³C NMR (126 MHz, CDCl₃) δ 137.38 (Ar), 128.66 (Ar), 128.20 (Ar), 127.81 (Ar), 112.07 (C(CH₃)₂), 105.59 (C1), 82.82 (C3), 82.54 (C2), 82.18 (C4), 72.06 (PhCH₂), 50.32 (C5), 43.31 (C6), 26.99 ($^i$Pr), 26.46 ($^i$Pr)).

2,4-Di-O-acetyl-1,6-anhydro-3-O-benzyl-/3-L-idopyranose, Intermediate I.27

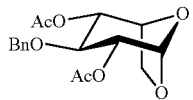

Intermediate I.25 (8.5 g, 29.1 mmol, 1 eq) was dissolved in a solution of 1,4-dioxane: 2 M H₂SO₄ (36 mL, 1:1 (v/v) and refluxed at 100° C. overnight. The following day the reaction was cooled back down to rt and neutralised by the addition of sat. aq. Ba(OH)₂·8H₂O, and the solids were removed by filtration and washed with H₂O and EtOAc. The layers were separated and the aqueous layer was extracted an additional 3 times with EtOAc and the combined organic layers were washed once with H₂O and dried on MgSO₄, filtered and concentrated. The resulting residue was recrystallized from EtOH giving intermediate I.26 as a yellow solid. The mother liquor was purified by flash chromatography (Cyclohexane/EtOAc 10-80%) to yield additional 1.26 as a yellow solid to yield in total 3.3 g (13.1 mmol, 45%) (R$_f$: 0.17 (Cyclohexane/EtOAc, 3:2 v/v). ¹H NMR and ¹³C NMR in accordance with the literature Carbohydr. Res. 2008, 343 (4), 596-606. Intermediate I.26 (2.87 g, 11.38 mmol, 1 eq) was dissolved in dry pyridine (23 mL) and cooled on ice. Ac₂O (15 mL) was added slowly and the reaction was warmed back to rt and stirred overnight. The following day the reaction was placed back on ice and quenched with H₂O (30 mL) and diluted with CH₂Cl₂ (120 mL). This was then washed sequentially with 2 M HCl, sat aq. NaHCO₃, H₂O and brine. The organic layer was dried on MgSO₄, filtered and concentrated and the residue was purified by flash chromatography (Cyclohexane/EtOAc 8-66%) to yield intermediate I.27 (3.47 g, 10.3 mmol, 91%) as a yellow solid (R$_f$: (Cyclohexane/EtOAc, 3:2 v/v) 0.37. ¹H NMR (500 MHz, CDCl₃) δ 7.37-7.24 (m, 5H, Ar), 5.44 (d, J=1.8 Hz, 1H, H1), 5.05 (ddd, J=8.7, 4.3, 1.2 Hz, 1H, H4), 4.83 (dd, J=8.3, 1.8 Hz, 1H, H2), 4.65 (d, J=1.4 Hz, 2H, BnCH₂), 4.59 (d, J=4.6 Hz, 1H, H5), 4.01 (dd, J=7.9, 0.7 Hz, 1H, H6a), 3.86 (t, J=8.5 Hz, 1H, H3), 3.72 (ddd, J=7.9, 5.0, 1.1 Hz, 1H, H6b), 2.05 (s, 3H, COCH₃), 2.01 (s, 3H, COCH₃) ¹³C NMR (126 MHz, CDCl₃) δ 170.10 (Carbonyl), 169.76 (Carbonyl), 138.12 (Ar), 128.46 (Ar), 127.85 (Ar), 127.64 (Ar), 99.26 (01), 77.11 (C3), 76.17 (C2), 74.49 (PhCH₂), 72.66 (C4), 72.65 (C5), 65.65 (C6), 20.95 (COCH₃), 20.91 (COCH₃)).

Phenyl 2,4,6-tri-O-acetyl-3-O-benzyl-1-thio-α-L-idopyranoside, Intermediate I.29

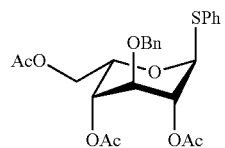

Intermediate I.27 (300 mg, 0.89 mmol, 1 eq) was dissolved in dry CH₂Cl₂ (5 mL) and placed on ice. Ac₂O (2 mL) was then added before TMSOTf (15 μL, 0.083 mmol, 0.09 eq) was added under N₂. Reaction was stirred on ice for 5 minutes before warming back to rt. After 20 minutes TLC showed consumption of the starting material and the formation of two new spots R$_f$ 0.40 & 0.33 (Tol:EtOAc, 2:1 v/v) and the reaction was quenched by the addition of NEt₃. Solvents were removed and the obtained syrup was purified by flash chromatography (Tol/EtOAc 8-66%) to yield an anomeric mixture of tetraacetate I.28 (340 mg, 0.78 mmol, 87%), which was used without any further characterisation.

Intermediate I.28 (333 mg, 0.76 mmol, 1 eq) was dissolved in dry CH₂Cl₂ (7 mL) and placed on ice. HSPh (90 μL, 0.84 mmol, 1.1 eq) was added and the mixture stirred for 5 minutes before the addition of BF₃·Et₂O (0.28 mL, 2.28 mmol, 3 eq). The reaction mixture was allowed warm back to rt and stirred for 3 hours before an additional BF₃·Et₂O (0.15 mL, 1.22 mmol, 1.6 eq) was added at rt. Once complete the reaction was placed on ice and quenched with 5 mL of sat. aq. NaHCO₃ and the layers were separated. The organic layer was washed with H₂O, dried on MgSO₄, filtered and concentrated. The resulting residue was purified by flash chromatography (Tol/EtOAc 5-40%) to yield I.29 (335 mg, 0.69 mmol, 90%) as a slightly orange syrup (R$_f$: 0.67 (Tol/EtOAc, 2:1 v/v) ¹H NMR (500 MHz, CDCl₃) δ 7.57-7.53 (m, 2H, Ar), 7.46-7.42 (m, 2H. Ar), 7.39 (ddd, J=7.6, 6.8, 1.3 Hz, 2H, Ar), 7.35-7.27 (m, 4H, Ar), 5.50 (brs, J=1.2, 0.6 Hz, 1H, H1), 5.17 (dt, J=2.5, 1.1 Hz, 1H, H2), 5.01 (ddd, J=7.7, 4.9, 1.7 Hz, 1H, H5), 4.89 (ddt, J=2.7, 1.7, 0.8 Hz, 1H, H4), 4.84 (d, J=11.8 Hz, 1H, PhCH₂), 4.73-4.68 (m, 1H, PhCH₂), 4.27 (dd, J=11.5, 7.8 Hz, 1H, H6a), 4.20 (dd, J=11.5, 5.0 Hz, 1H, H6b), 3.79 (td, J=2.8, 1.2 Hz, 1H, H3), 2.09 (s, 3H, COCH₃), 2.07 (s, 3H, COCH₃), 2.02 (s, 3H, COCH₃) ¹³C NMR (126 MHz, CDCl₃) δ 170.71 (Carbonyl), 170.19 (Carbonyl), 169.65 (Carbonyl), 135.96 (Ar), 131.55 (Ar), 129.17 (Ar), 129.03 (Ar), 128.64 (Ar), 128.36 (Ar), 128.15 (Ar), 127.58 (Ar), 85.98 (C1), 72.78 (PhCH₂), 71.60 (C3), 68.90 (C2), 67.22 (C4), 64.73 (C5), 62.94 (C6), 21.09 (COCH₃), 20.96 (COCH₃), 20.88 (COCH₃)).

Phenyl 3-O-benzyl-1-thio-α-L-idopyranoside, Intermediate I.30

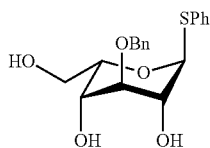

Intermediate I.29 (890 mg, 1.82 mmol, 1 eq) was dissolved in dry MeOH (9 mL) and freshly prepared NaOMe was added and the mixture was stirred overnight at rt. The following day the reaction was quenched with the addition of DOWEX 50 WX8 acid resin, filtered and washed with additional MeOH. The filtrate was concentrated to yield I.30 (606 mg, 1.67 mmol, 92%) as a yellow foam ($^1$H NMR (500 MHz, CDCl$_3$) δ 7.52-7.48 (m, 2H, Ar), 7.43-7.35 (m, 4H, Ar), 7.33-7.23 (m, 4H, Ar), 5.58 (s, 1H, H1), 4.80 (d, J=11.8 Hz, 1H, PhCH$_2$), 4.57 (d, J=11.9 Hz, 1H, PhCH$_2$), 4.54-4.50 (m, 1H, H5), 4.14-4.07 (m, 2H, H2, H4), 4.07-3.97 (m, 2H, H6a, H6b), 3.78-3.72 (m, 1H, H3) $^{13}$C NMR (126 MHz, CDCl$_3$) δ 137.60 (Ar), 136.90 (Ar), 131.18 (Ar), 129.10 (Ar), 128.63 (Ar), 128.08 (Ar), 127.83 (Ar), 127.26 (Ar), 90.32 (C1), 74.33 (C3), 72.39 (PhCH$_2$), 71.42 (C2), 68.87 (C4), 66.21 (C5), 65.92 (C6)).

Phenyl 2-O-benzoyl-3-O-benzyl-4,6-O-(1-naphthyl) methylidene-1-thio-α-L-idopyranoside, Intermediate I.32

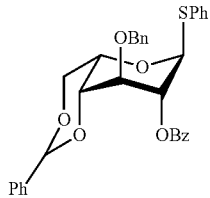

Intermediate I.30 (1.55 g, 4.38 mmol, 1 eq) was dissolved in 20 mL dry CH$_2$Cl$_2$ and the flask was covered in foil to exclude light. ZnI$_2$ (2.78 g, 17.5 mmol, 2 eq, dried for 8 hours while protected from light) was then added followed by TMSSPh (2.5 mL, 13.1 mmol, 3 eq) at room temperature. The reaction was stirred overnight. The following day TLC showed the starting material had disappeared and two new spots had appeared. The reaction mixture was passed through a pad of celite and the pad was washed with CH$_2$Cl$_2$ until the filtrate ran clear. 9 M HCl (15 mL) in H$_2$O (5 mL) and 1,4 dioxane (5 mL) was added to the filtrate and the mixture stirred vigorously at room temperature until TLC showed the disappearance of the higher spot. The layers were separated and the organic layer was washed with 2M HCl, saturated aqueous NaHCO$_3$ solution and H$_2$O. It was then dried on MgSO$_4$, filtered and concentrated and the resulting syrup was purified by column chromatography using 4:1→1:1 (cyclohexane/EtOAc) to give intermediate I.31 (1.56 g, 3.34 mmol, 75%) as a white foam ($^1$H NMR in agreement with the literature. J. Org. Chem. 2013, 78 (14), 6911-6934).

Intermediate I.31 (390 mg, 0.84 mmol, 1 eq) was dissolved in 2.5 mL dry DMF and camphorsulfonic acid (136 mg, 0.59 mmol, 0.7 eq) and benzaldehyde dimethylacetal (0.4 mL, 2.51 mmol, 3 eq) were added before heating the mixture to 60° C., stirring overnight. The following day the reaction was cooled back to room temperature and placed on ice before quenching with NEt$_3$. The solvents were removed in vacuo and the crude was coevaporated twice with cyclohexane. The crude was purified with 4:1→2:1 cyclohexane/ ethyl acetate to give intermediate I.32 (360 mg, 0.65 mmol, 78%) as a white foam ($^1$H NMR (500 MHz, CDCl$_3$) δ 7.95 (dd, J=8.3, 1.4 Hz, 2H, Ar), 7.58-7.16 (m, 18H, Ar), 5.82 (s, 1H, H1), 5.58 (s, 1H, PhCH), 5.53 (dt, J=2.3, 1.0 Hz, 1H, H2), 4.98 (d, J=11.8 Hz, 1H, PhCH$_2$), 4.70 (d, J=11.8 Hz, 1H, PhCH$_2$), 4.52 (d, J=1.7 Hz, 1H, H5), 4.38 (dd, J=12.7, 1.5 Hz, 1H, H6a), 4.19 (dd, J=12.7, 1.9 Hz, 1H, H6b), 4.11 (td, J=1.7, 0.8 Hz, 1H, H4), 3.94-3.90 (m, 1H, H3) in agreement with literature, Carbohydr. Res. 2008, 343 (4), 596-606).

(v) Synthesis of Monosaccharide Building Block E

Scheme 5

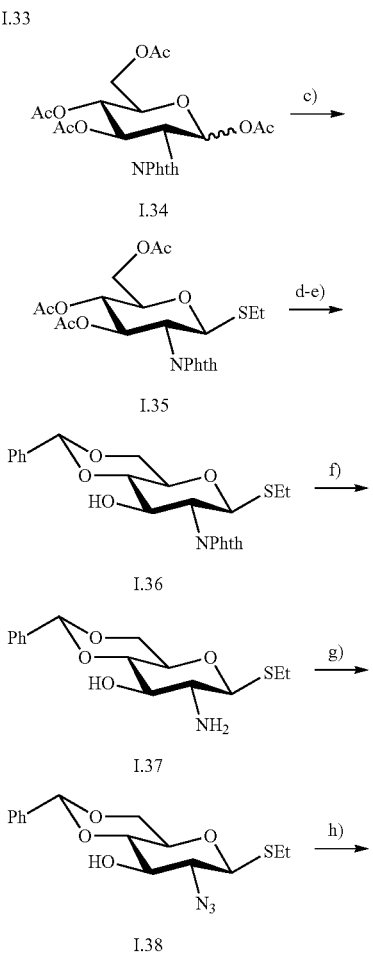

-continued

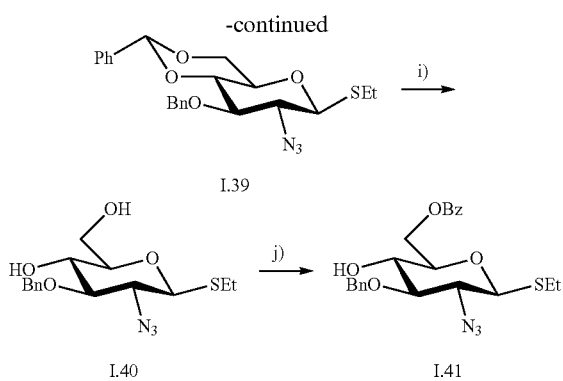

Reagents and conditions: Synthesis of intermediate I.41. a) MeOH/H₂O, NaOH, NaHCO₃, Pthalic anhydride, rt, 3 hours; b) Pyridine, Ac₂O, 0°C → rt, overnight, 47% (2 steps); c) HSEt, TMSOTf, Cl CH₂CH₂Cl, 0 → rt → 40° C., 5 hours, 86%; d) MeOH, NaOMe, rt, overnight; e) CSA, Benzaldehyde dimethyl acetal, DMF, 60° C., overnight, 77% (2 steps); f) NH₂CH₂CH₂NH₂, EtOH, 80° C., 2 hours, 95%; g) MeOH, THF, K₂CO₃, Cu(II)SO₄·5 H₂O, 0° C. → rt, 1H-imidazole-1-sulfonyl azide hydrochloride, 5 hours, 87%; h) NaH, BnBr, DMF, 0° C. → rt, 3.5 hours, 91%; i) Dry MeOH/CH₂Cl₂, CSA, rt, 5 hours, 92%; j) CH₂Cl₂, Pyridine, BzCl, -50° C., 2 hours, 88%; j)

Ethyl 3,4,6-tri-O-acetyl-2-deoxy-2-phthalimido-1-thio-/3-D-glucopyranoside, Intermediate I.35

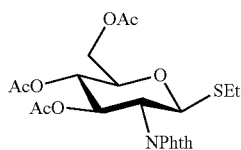

Commercially available I.33 (20 g, 92.8 mmol, 1 eq) was dissolved in 120 mL 1:2 v/v MeOH:H₂O solution to which NaOH pellets (4.3 g, 107.59 mmol, 1.16 eq) were added, stirring at rt until the pellets had dissolved completely. Phthalic anhydride (15.93 g, 107.59 mmol, 1.16 eq, dissolved in acetone) was then added to the mixture and stirred for 3 hours before additional phthalic anhydride (6.18 g, 41.74 mmol, 0.45 eq) and NaHCO₃ (15.58 g, 185.5 mmol, 2 eq) was added. The solution was then acidified with 4 M HCl to pH 1 and the volume of solvents reduced to half. The mixture was allowed to sit at rt overnight leading to a precipitate forming. The reaction vessel was cooled on an ice bath for 1 hour to aid further precipitation before filtration to collect the white solids. The solids were washed twice with chilled distilled water and cold EtOH. The obtained solid was then dried under vacuum before being suspended in pyridine (200 mL) and cooled on ice. Ac₂O (180 mL) was added slowly through a dropping funnel over 30 minutes and upon complete addition the reaction mixture was allowed to warm back to rt slowly and stirred overnight. The solvent was removed by repeated coevaporation with toluene and the resulting residue was taken up into CH₂Cl₂ and washed sequentially with 2 M HCl, sat. aq. NaHCO₃, H₂O and brine. The organic layer was dried on MgSO₄, filtered and concentrated and the resulting residue was diluted with EtOH and stirred overnight leading to the product to precipitate as a white solid. The solids were isolated by filtration and washed with cold EtOH and dried under vacuum to yield intermediate I.34 (20.8 g, 43.56 mmol, 47%) as a white solid (R$_f$: 0.26 (Cyclohexane/EtOAc, 3:2 v/v). ¹H NMR and ¹³C NMR in agreement with literature, *Synlett* 2008, 2008(10), 1483-1486).

Intermediate I.34 (21.5 g, 45.03 mmol, 1 eq) was dissolved in 220 mL dry ClCH₂CH₂Cl and placed on ice. HSEt (8.12 mL, 112.58 mmol, 2.5 eq) was added and the mixture was stirred for 5 minutes before TMSOTf (12.1 mL, 67.55 mmol, 1.5 eq) was added, stirring on ice for 30 minutes and then warmed back to rt. After 30 minutes the mixture was heated to 40° C. and starting material was no longer visible on TLC after 4 hours. Reaction mixture was cooled back to rt, placed on ice and quenched with NEt₃ (18.8 mL, 135.1 mmol, 3 eq). Solvents were evaporated and the obtained residue was dissolved in EtOAc and washed with H₂O, sat. aq. NaHCO₃ and brine. The organic layer was dried on MgSO₄, filtered and concentrated to yield a yellow syrup which was purified by flash chromatography (Tol/EtOAc 5-40%) to yield intermediate I.35 (18.5 g, 38.58 mmol, 86%) as a white foam (R$_f$: 0.24 (Tol/EtOAc, 6:1 v/v) ¹H NMR (500 MHz, CDCl₃) δ 7.88-7.83 (m, 2H, Ar), 7.77-7.70 (m, 2H, Ar), 5.82 (t, J=10.4 Hz, 1H, H3), 5.48 (d, J=10.6 Hz, 1H, H1), 5.17 (t, J=10.4 Hz, 1H, H4), 4.42-4.36 (m, 1H, H2), 4.30 (dd, J=12.3, 4.9 Hz, 1H, H6a), 4.20-4.15 (m, 1H, H6b), 3.89 (ddd, J=10.1, 4.8, 2.2 Hz, 1H, H5), 2.76-2.59 (m, 2H, SCH₂CH₃), 2.10 (s, 3H, COCH₃), 2.03 (s, 3H, COCH₃), 1.86 (s, 3H, COCH₃), 1.21 (t, J=7.5, 1.3 Hz, 3H, SCH₂CH₃) ¹³C NMR (126 MHz, CDCl₃) 170.83 (COCH₃), 170.23 (COCH₃), 169.60 (COCH₃), 134.57 (Ar), 134.41 (Ar), 123.83 (Ar), 81.32 (C1), 76.06 (C5), 71.68 (C3), 69.02 (C4), 62.43 (C6), 53.81 (C2), 24.50 (SCH₂CH₃), 20.91 (COCH₃), 20.77 (COCH₃), 20.59 (COCH₃), 15.03 (SCH₂CH₃) in agreement with literature, *Carbohydr. Res.* 1985, 139, 105-113).

Ethyl 2-amino-4,6-O-benzylidene-2-deoxy-1-thio-β-D-glucopyranoside, Intermediate I.37

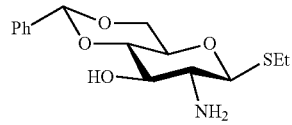

Intermediate I.35 (18.3 g, 39.32 mmol, 1 eq) was suspended in dry MeOH (180 mL) and freshly prepared NaOMe was added at rt and the mixture was stirred overnight. Afterwards the reaction was quenched by the addition of DOWEX 50WX8 acid resin until pH 7 was reached and then the mixture was filtered and washed with MeOH. The obtained filtrate was concentrated and coevaporated once with toluene. The crude material was dried overnight before being dissolved in dry DMF (140 mL). Benzaldehyde dimethyl acetal (17.7 mL, 117.96 mmol, 3 eq) and CSA (6.39 g, 27.52 mmol, 0.7 eq) were then added and the mixture was heated at 60° C. and stirred overnight. The following day the mixture was cooled to rt, placed on ice and quenched with NEt₃ (16.4 ml, 117.96 mL, 3 eq). Solvents were removed in vacuo and the obtained residue was coevaporated twice with cyclohexane. The obtained syrup was then purified by flash chromatography (Tol/EtOAc 5-40%) to yield intermediate I.36 (13.4 g, 30.4 mmol, 77%) as a white foam (R$_f$: 0.37 (Tol/EtOAc, 4:1 v/v). ¹H NMR and ¹³C NMR in agreement with literature, *European J. Org. Chem.* 2009, 2009 (7), 997-1008).

Intermediate I.36 (4.2 g, 9.51 mmol, 1 eq) was suspended in EtOH (100 mL) and ethylene diamine (24 mL, 380.4 mmol, 40 eq) was added and the mixture was stirred for 2 hours at 80° C. when TLC showed no more starting material.

The mixture was cooled back to rt and the solvents removed in vacuo and the obtained yellow residue was coevaporated twice with MeCN and once with toluene. The residue was purified by column chromatography (100 CH$_2$Cl$_2$→95:5 CH$_2$Cl$_2$/MeOH) to yield intermediate I.37 (2.8 g, 8.99 mmol, 95%) as a white solid (R$_f$: 0.10 (EtOAc) $^1$H NMR (400 MHz, CDCl$_3$) δ 7.50-7.44 (m, 2H, Ar), 7.39-7.31 (m, 2H, Ar), 5.48 (s, 1H, PhCH), 4.29-4.23 (m, 2H, H1, H6a), 3.69 (t, J=10.2 Hz, 1H, H6b), 3.56-3.44 (m, 2H, H3, H4), 3.41-3.31 (m, 1H, H5), 2.75-2.69 (m, 1H, H2), 2.68-2.59 (m, 2H, SCH$_2$CH$_3$), 1.26 (t, J=7.4 Hz, 3H, SCH$_2$CH$_3$) $^{13}$C NMR (101 MHz, CDCl$_3$) δ 137.22 (Ar), 129.25 (Ar), 128.35 (Ar), 126.33 (Ar), 101.90 (PhCH), 87.49 (C1), 81.12 (C3), 74.23 (C4), 70.52 (C5), 68.61 (C6), 56.92 (C2), 24.57 (SCH$_2$CH$_3$), 15.28 (SCH$_2$CH$_3$) in agreement with literature, *Tetrahedron*, 1997, 53 (52), 17727-17734).

Ethyl 2-azido-3-O-benzyl-4,6-O-benzylidene-2-deoxy-1-thio-β-D-glucopyranoside, Intermediate I.39

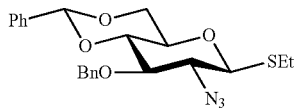

Intermediate I.37 (3.53 g, 11.34 mmol, 1 eq) was dissolved in dry THF (11 mL) and dry MeOH (43 mL), before dried Cu(II)·SO$_4$.5H$_2$O (11 mg, 0.05 mmol, 0.01 eq), dried K$_2$CO$_3$ (1.02 g, 7.23 mmol, 1.5 eq) and 1H-imidazole-1-sulfonyl azide hydrochloride (1.21 g, 5.78 mmol, 1.2 eq, prepared by the method described in *Org. Lett.*, 2007, 9(19), 3797-3800) were added at rt under N$_2$. The mixture was stirred for 5 h when TLC showed no more starting material. The reaction mixture was diluted with CH$_2$Cl$_2$ (50 mL) and washed twice with H$_2$O (30 mL). The organic layer was dried on MgSO$_4$, filtered and concentrated to yield a pale yellow solid. This was purified by flash chromatography (Tol/EtOAc 3-28%) to yield intermediate I.38 (3.33 g, 9.87 mmol, 87%) as a white solid (R$_f$: 0.42 (Tol/EtOAc, 6:1 v/v) $^1$H NMR and $^{13}$C NMR in agreement with literature, *Tetrahedron* 1997, 53(52), 17727-17734).

Intermediate I.38 (4.2 g, 12.45 mmol, 1 eq) was dissolved in dry DMF (18.6 mL) and cooled on ice. 60% NaH (in mineral oil) (1.25 g, 31.13 mmol, 2.5 eq) was added under N$_2$ and the mixture was stirred for 30 minutes on ice. BnBr (3.7 mL, 31.13 mmol, 2.5 eq) was then added slowly and after stirring for 5 minutes on ice the reaction was allowed to warm back to room temp. After 3 hours 40 minutes no more starting material could be seen on TLC and the reaction was placed on ice and carefully quenched by the addition of MeOH (10.1 mL, 249 mmol, 20 eq). Solvents were removed in vacuo and the residue was coevaporated three times with toluene. The residue was dissolved in EtOAc (150 mL) and washed twice with H$_2$O (180 mL). The combined aqueous layer was re-extracted with additional EtOAc. The combined organic layer was dried on MgSO$_4$, filtered and concentrated and the afforded residue was purified by flash chromatography (Cyclohexane/EtOAc 3-28%) to yield I.39 (4.85 g, 11.35 mmol, 91%) as a white solid (R$_f$: 0.31 (Cyclohexane/EtOAc, 6:1 v/v) $^1$H NMR (500 MHz, CDCl$_3$) δ 7.51-7.47 (m, 2H, Ar), 7.43-7.28 (m, 3H, Ar), 5.59 (s, 1H, PhCH), 4.95 (d, J=11.0 Hz, 1H, PhCH$_2$), 4.82 (d, J=11.1 Hz, 1H, PhCH$_2$), 4.39-4.33 (m, 2H, H1, H6a), 3.81-3.71 (m, 2H, H6b, H4), 3.65 (t, J=9.0 Hz, 1H, H3), 3.50-3.41 (m, 2H, H2, H5), 2.86-2.68 (m, 2H, SCH$_2$CH$_3$), 1.32 (t, J=7.4 Hz, 3H, SCH$_2$CH$_3$) $^{13}$C NMR (126 MHz, CDCl$_3$) δ 137.79 (Ar), 137.22 (Ar), 129.23 (Ar), 128.56 (Ar), 128.45 (Ar), 128.41 (Ar), 128.11 (Ar), 126.11 (Ar), 101.44 (PhCH), 85.09 (C1), 81.64 (C4), 81.02 (C3), 75.24 (PhCH$_2$), 70.58 (C5), 68.65 (C6), 65.88 (C2), 25.08 (SCH$_2$CH$_3$), 15.15 (SCH$_2$CH$_3$) in agreement with literature. *Tetrahedron* 1997, 53(52), 17727-17734).

Ethyl 2-azido-6-O-benzoyl-3-O-benzyl-2-deoxy-thio-/3-D-glucopyranoside, Intermediate I.41

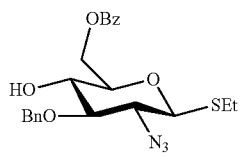

Intermediate I.39 (1.07 g, 2.5 mmol, 1 eq) was dissolved in dry MeOH:CH$_2$Cl$_2$ (24 mL, 8:1 v/v) at rt and once completely dissolved CSA (407 mg, 1.75 mmol, 0.7 eq) was added under N$_2$. After 4 h and 20 minutes additional CSA (58 mg, 0.25 mmol, 0.1 eq) was added at rt. After 30 minutes the reaction was quenched by the addition of NEt$_3$ while cooled on ice. The solvents were concentrated and the resulting syrup was purified by flash chromatography (Cyclohexane/EtOAc 8-66%) to yield intermediate I.40 (786 mg, 2.32 mmol, 92%) as a clear syrup (R$_f$: 0.20 (Cyclohexane/EtOAc, 2:1 v/v) $^1$H NMR and $^{13}$C NMR in agreement with literature, Angew. Chemie—Int. Ed. 2017, 56 (9), 2312-2317).

Intermediate I.40 (775 mg, 2.28 mmol, 1 eq) was dissolved in dry CH$_2$Cl$_2$ (3.6 mL) and dry pyridine (0.7 mL) was added before the mixture was cooled to −50° C. Once stirring at this temperature for 5 minutes BzCl (260 μL, 2.28 mmol, 1 eq) was added under N$_2$ and then remained stirring at −50° C. After 1.5 h an additional 50 μL (0.4 mmol, 0.18 eq) BzCl was added and after 20 minutes the reaction was quenched by the addition of water and CH$_2$Cl$_2$. The mixture was then washed sequentially with 2 M HCl, sat. aq. NaHCO$_3$, H$_2$O and brine. The organic layer was dried on Na$_2$SO$_4$, filtered and concentrated. The resulting residue was purified by flash chromatography (Cyclohexane/EtOAc 8-66%) to yield I.41 (887 mg, 2.00 mmol, 88%) as a white solid (R$_f$: 0.53 (Cyclohexane/EtOAc 2:1 v/v) $^1$H NMR (400 MHz, CDCl$_3$) 8.04 (dd, J=8.3, 1.4 Hz, 2H, Ar), 7.57 (ddt, J=7.9, 7.0, 1.3 Hz, 1H, Ar), 7.49-7.28 (m, 7H, Ar), 4.96 (d, J=11.1 Hz, 1H, PhCH$_2$), 4.85 (d, J=11.2 Hz, 1H, PhCH$_2$), 4.66 (dd, J=12.2, 4.5 Hz, 1H, H6a), 4.54 (dd, J=12.2, 2.0 Hz, 1H, H6b), 4.41-4.30 (m, 1H, H1), 3.63-3.49 (m, 2H, H4, H5), 3.46-3.35 (m, 2H, H2, H3), 2.87 (d, J=3.2 Hz, 1H, 4-OH), 2.83-2.66 (m, 2H, SCH$_2$CH$_3$), 1.31 (t, J=7.4 Hz, 3H, SCH$_2$CH$_3$) $^{13}$C NMR (101 MHz, CDCl$_3$) δ 167.17 (OBz), 137.87 (Ar), 133.48 (Ar), 129.94 (Ar), 129.64 (Ar), 128.83 (Ar), 128.54 (Ar), 128.35 (Ar), 128.34 (Ar), 84.59 (C1), 84.46 (C3), 78.17 (C5), 75.69 (PhCH$_2$), 70.29 (C4), 65.77 (C2), 63.80 (C6), 24.87 (SCH$_2$CH$_3$), 15.20 (SCH$_2$CH$_3$) HR-MS Calc. for C22H25N3O5NaS [M+Na]+: 466.1413 Found: 466.1396).

(vi) Synthesis of Monosaccharide E with Linker

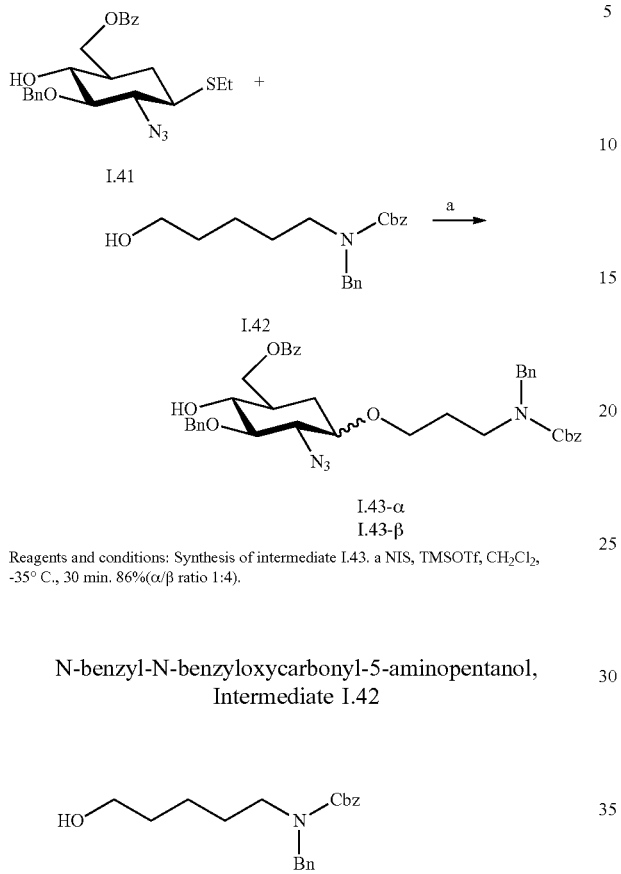

Reagents and conditions: Synthesis of intermediate I.43. a NIS, TMSOTf, CH$_2$Cl$_2$, -35° C., 30 min. 86%(α/β ratio 1:4).

N-benzyl-N-benzyloxycarbonyl-5-aminopentanol, Intermediate I.42

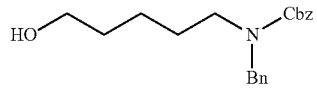 [SMILES: O=C(OCc1ccccc1)N(CCCCCO)Cc1ccccc1]

Commercially available 5-amino-pentan-1-ol (5.31 g, 51.47 mmol, 1 eq) was dissolved in 80 mL absolute EtOH and benzaldehyde (5.4 mL, 53.01 mmol, 1.1 eq) was added. The solvent was slowly removed on a rotary evaporator at 50° C. over the course of 3 hours. An additional 80 mL absolute EtOH was added and the mixture was concentrated until no more solvent condensed. The residue was then coevaporated twice with toluene under reduced pressure before dissolving in 70 mL in MeOH and cooling to 0° C. NaBH$_4$ (2.3 g, 60.74 mmol, 1.2 eq) was then added slowly in portions, allowing the evolution of gases to cease before the next addition. Once all the NaBH$_4$ had been added the reaction was warmed to room temperature and stirred for 2 hours. It was placed back on ice and AcOH (5.3 mL, 92.65 mmol, 1.8 eq) was added slowly to quench the remaining NaBH$_4$. K$_2$CO$_3$ (12.1 g, 87.5 mmol, 1.7 eq) in H$_2$O (75 mL) was added and the mixture was stirred at room temperature overnight. The following day the mixture was diluted with 100 mL Et$_2$O and the layers were separated. The aqueous layer was extracted once more with Et$_2$O. The combined organic layers were concentrated to roughly half volume. 130 mL of a saturated aqueous NaHCO$_3$ solution was added and the biphasic mixture was cooled to 0° C. CbzCl (7.3 mL, 51.5 mmol, 1.1 eq) was then added slowly and the mixture was stirred overnight, slowly warming to room temperature. The following day the mixture was diluted with 200 mL Et$_2$O and the layers were separated. The organic layer was then sequentially washed with 1M HCl, H$_2$O and brine.

After drying on MgSO$_4$ and filtering, the filtrate was concentrated and the crude material was purified by column chromatography using 3:1→1:1 cyclohexane/ethyl acetate to yield 10.64 g of intermediate I.42 as a clear syrup (32.5 mmol, 63% over 3 steps) ($^1$H NMR (500 MHz, CDCl$_3$) δ 7.41-7.15 (m, 10H, Ar), 5.18 (d, J=13.3 Hz, 2H), 4.50 (d, J=8.0 Hz, 2H), 3.57 (d, J=34.8, 6.7 Hz, 2H), 3.30-3.20 (m, 2H), 1.59-1.45 (m, 4H), 1.37-1.24 (m, 2H). In agreement with literature Org. Lett. 2013, 15 (9), 2270-2273).

N-benzoxycarbonyl-N-benzyl-5-amino-pentanyl 2-azido-6-O-benzoyl-3-O-benzyl-2-deoxy-β-D-glucopyranoside, Intermediate I.43-β

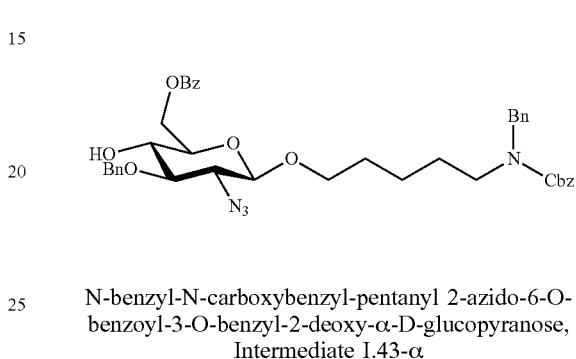

N-benzyl-N-carboxybenzyl-pentanyl 2-azido-6-O-benzoyl-3-O-benzyl-2-deoxy-α-D-glucopyranose, Intermediate I.43-α

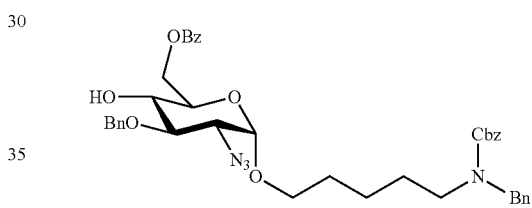

Intermediate I.41 (1.21 g, mmol, 1 eq) and Intermediate I.42 (1.79 g, mmol, 2 eq) were coevaporated together with toluene and dried under vacuum for 1 hour before being dissolved in 40 mL dry CH$_2$Cl$_2$. The mixture was cooled to −40° C. and the reaction vessel was wrapped in foil to exclude light. NIS (1.3 eq, dried under vacuum while protected light) was then added followed by TMSOTf (0.1 eq) The reaction stirred under darkness, gradually warming for 45 minutes when TLC (1:1 v/v Pentane/Et$_2$O) showed no remaining thioglycoside. The reaction was quenched by the addition of solid K$_2$CO$_3$ and 20 mL aqueous 10% Na$_2$S$_2$O$_3$ solution. The mixture was transferred to a separating funnel and shaken until it became colourless. 100 mL Et$_2$O was added and the aqueous layer was removed. The organic layer was washed with water and brine and then dried on MgSO$_4$ and filtered. The filtrate was concentrated and the resulting crude syrup was purified using automatic flash chromatography (12-100% Pentane/Et$_2$O) to first elute intermediate I.43-α material (340 mg, 0.48 mmol, 17%) and then intermediate I.43-β material (1.2 g, 1.69 mmol, 69%) as clear syrups Information for the β anomer; R$_f$=0.27 (1/1 v/v Pentane/Et$_2$O) HRMS calc for C$_{40}$H$_{45}$N$_4$O$_8$ [M+H]$^+$: 709.3237 Found 709.3204 $^1$H NMR (500 MHz, DMSO-d$_6$) δ 8.00-7.96 (m, 2H, Ar), 7.67-7.62 (m, 1H, Ar), 7.54-7.49 (m, 2H, Ar), 7.44-7.39 (m, 2H, Ar), 7.37-7.17 (m, 15H, Ar), 5.77 (d, J=6.4 Hz, 1H, 4-OH), 5.10 (bs, 2H, NCH$_2$Bn), 4.90 (d, J=11.4 Hz, 1H, BnCH$_2$), 4.72 (d, J=11.4 Hz, 1H, BnCH$_2$), 4.55 (dd, J=11.9, 2.1 Hz, 1H, H6a), 4.42 (bs, 3H, H1, OCH$_2$Bn linker), 4.38 (dd, J=11.9, 5.7 Hz, 1H, H6b), 3.72-3.60 (m, 2H, CH$_2$ linker, H5), 3.58-3.52 (m, 1H, H4), 3.47-3.41 (m, 1H, CH$_2$ linker), 3.40-3.34 (m, 2H, H2, H3), 3.14 (bs, 2H, CH$_2$ Linker), 1.43 (bs, 4H, CH$_2$ Linker×2), 1.19 (bs, 2H, CH$_2$ Linker) $^{13}$C NMR (126 MHz, DMSO-d$_6$) δ 165.49 (Carbonyl), 138.52 (Ar), 133.28 (Ar), 129.61 (Ar), 129.09 (Ar), 128.65 (Ar), 128.34 (Ar), 128.26 (Ar), 128.00 (Ar), 127.67 (Ar), 127.64 (Ar), 127.38 (Ar), 127.32 (Ar), 127.01 (Ar), 100.76 (01), 82.12 (C2), 73.90 (CH$_2$Bn), 73.40 (C5), 69.94 (C4), 68.69 (CH$_2$ Linker), 66.22 (NCH$_2$Bn), 65.19 (C3), 63.55 (C6), 49.37 (OCH$_2$Bn), 45.90 (CH$_2$ Linker), 28.61 (CH$_2$ Linker), 27.28 (CH$_2$ Linker), 22.46 (CH$_2$ Linker)).

Information for the α anomer; (R$_f$; 0.28 (1:1 v/v Pentane/Et$_2$O), [α]$_D$+51.6 (c=1, DMSO), $^1$H NMR $^1$H NMR (500 MHz, DMSO-d$_6$) δ 7.97-7.93 (m, 2H, Ar), 7.66-7.60 (m, 1H, Ar), 7.52-7.46 (m, 2H, Ar), 7.41-7.13 (m, 15H, Ar), 5.80 (d, J=7.0 Hz, 1H, 4-OH), 5.09 (d, J=13.3 Hz, 2H, NCH$_2$), 4.95 (d, J=11.3 Hz, 1H, BnCH$_2$), 4.88 (bs, 1H, H1), 4.68 (d, J=11.2 Hz, 1H, BnCH$_2$), 4.56 (dd, J=11.9, 2.1 Hz, 1H, H6a), 4.42 (s, 2H, OCH$_2$Bn), 4.36 (dd, J=11.8, 6.0 Hz, 1H, H6b), 3.81 (bs, 1H, H5), 3.70 (d, J=9.7 Hz, 1H, H3), 3.63-3.48 (m, 2H, H4, CH$_2$ Linker×1), 3.41 (dd, J=10.4, 3.5 Hz, 1H, H2), 3.33 (1H, CH$_2$ Linker, overlap with solvent peak) 3.15 (s, 2H, CH$_2$ Linker), 1.44 (m, 4H, CH$_2$ Linker×2), 1.22 (s, 2H, CH$_2$ Linker). $^{13}$C NMR (126 MHz, DMSO-d$_6$) δ 165.44 (Carbonyl), 138.43 (Ar), 138.06 (Ar), 133.30 (Ar), 129.51 (Ar), 129.03 (Ar), 128.65 (Ar), 128.35 (Ar), 128.24 (Ar), 128.03 (Ar), 127.99 (Ar), 127.67 (Ar), 127.60 (Ar), 127.36 (Ar), 127.02 (Ar), 96.86 (C1), 79.20 (C3), 73.87 (BnCH$_2$), 70.53 (C4), 70.04 (C5), 66.99 (CH$_2$ Linker), 66.20 (NCH$_2$), 63.63 (C6), 61.82 (C2), 49.37 (OCH$_2$), 45.96 (CH$_2$ Linker), 28.48 (CH$_2$ Linker), 22.65 (CH$_2$ Linker). HR-MS calc. for C$_{40}$H$_{45}$N$_4$O$_8$ [M+H]$^+$: 709.3237 found 709.3204.)

(vii) Synthesis of Disaccharide Building Block BC

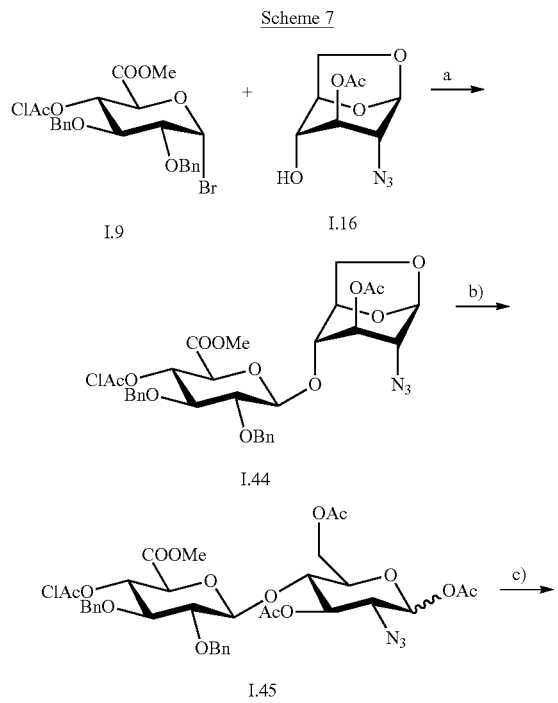

Scheme 7

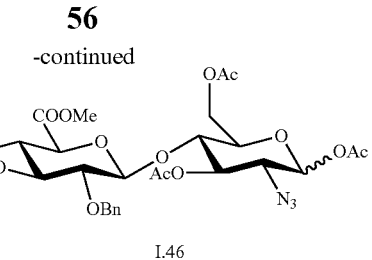

I.46

Reagents and conditions: Synthesis of intermedidate I.46 a) Ag$_2$CO$_3$, molecular sieves 4 Å, dry CH$_2$Cl$_2$, darkness b) Ac$_2$O, TBSOTf, 0° C., 10′, 70%; b) Thiourea, THF/EtOH 1:1, 80° C., 3 h 75%

Methyl 2,3-di-O-benzyl-4-O-chloroacetyl-β-D-glucopyranosyl-uronate-(1→4)-3-O-acetyl-1,6-anhydro-2-azido-2-deoxy-β-D-glucopyranose, Intermediate I.44

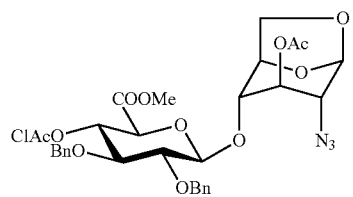

Method Using Ag$_2$CO$_3$:

A solution of intermediate I.9 (537 mg, 1.0 mmol, 1 eq), intermediate I.16 (930 mg, 4.0 mmol, 4.0 eq) and freshly activated 4 Å molecular sieves (560 mg) in dry CH$_2$Cl$_2$ (6 mL) was stirred at rt in the darkness under N$_2$ atmosphere for 30 min, then Ag$_2$CO$_3$ (560 mg, 2.0 mmol, 2 eq) was added. The mixture was stirred for 6 days, then TLC analysis showed complete conversion of the donor to the product (toluene/acetone 8:2). The reaction mixture was filtered through Celite. The filtrate was concentrated in vacuo and purified by automated flash chromatography (toluene/acetone 92/8 to 75/25) obtaining, Intermediate I.44 (343 mg, 0.5 mmol, 50% for only beta anomer) as white solid.

Method Using Ag$_2$CO$_3$/AgOTf:

Donor I.9 (444 mg, 0.84 mmol, 1.5 eq) and acceptor I.16 (130 mg, 0.56 mmol, 1.0 eq) were dried at Schlenck line overnight. 4 Å molecular sieves and dry CH$_2$Cl$_2$ (10 mL) were added and the mixture was stirred at rt under N$_2$ atmosphere for 1 hour in the darkness. Ag$_2$CO$_3$ (309 mg, 1.12 mmol, 2 eq) and AgOTf (144 mg, 0.56 mmol, 1 eq) were added and the reaction was stirred for 30 min (TLC cyclohexane/ethyl acetate 1:1). The reaction was quenched with TEA and filtered through Celite. The filtrate was concentrated in vacuo and purified by flash chromatography using cyclohexane/ethyl acetate 6:4 giving, Intermediate I.44 (178 mg, 0.26 mmol, 47% for only beta anomer) as white solid (R$_f$ (toluene/acetone 1:1) 0.33 $^1$H NMR (500 MHz, CDCl$_3$) δ 7.39-7.23 (m, 10H, H Ar), 5.50 (s, 1H, H1), 5.27 (m, 1H, H3), 5.23-5.16 (m, 1H, H3′), 5.01 (d, J=10.9 Hz, 1H, CHHPh), 4.84 (d, J=11.7 Hz, 1H, CHHPh), 4.78 (d, J=10.9 Hz, 1H, CHHPh), 4.68 (d, J$_{1,2}$=7.6 Hz, 1H, H1′), 4.64 (d, J=11.7 Hz, 1H, CHHPh), 4.58 (d, J$_{5,6b}$=5.8 Hz, J$_{5,6a}$=1.2 Hz, 1H, H5), 4.01 (dd, J$_{6a,6b}$=7.6 Hz, J$_{5,6a}$=1.2 Hz, 1H, H6a), 3.96 (d, J=10.0 Hz, 1H, H4′), 3.83 (d, J=14.9 Hz, 1H, OCHHCl), 3.78 (dd, J$_{6a,6b}$=7.5 Hz, J$_{5,6b}$=5.8 Hz, 1H, H6b), 3.72 (s, 3H, COOCH$_3$), 3.71 (d, J=14.9 Hz, 1H, OCHHCl), 3.69-3.65 (m, 3H, H2′, H5′, H4) 3.23 (br s, 1H, H2), 2.10 (s, 3H, CH₃CO) ¹³C NMR (126 MHz, CDCl₃) δ 169.4 (COCH₃), 167.4 (COOCH₃), 166.1 (COCH₂Cl), 138.2 (CqBn), 138.1 (CqBn), 128.6-128.0 (C' Ar), 103.1 (C1'), 100.3 (C1), 81.3 (C2'), 80.9 (C5' or C4), 76.2 (C5' or C4), 75.4 (CH₂Ph), 75.3 (CH₂Ph), 73.9 (C5), 72.4 (C3'), 72.1 (C4'), 70.8 (C3), 65.1 (C6), 59.0 (C2), 53.0 (COOCH₃), 40.5 (ClCH₂), 21.1 (COCH₃) HR-MS: calc. for C₃₁H₃₅ClN₃O₁₂Na [M+Na⁺]: 699.1807, found 699.1807).

Methyl 2,3-di-O-benzyl-4-O-chloroacetyl-β-D-glucopyranosyl-uronate-(1→4)-1,3,6-tri-O-acetyl-2-azido-2-deoxy-D-glucopyranose, Intermediate I.45

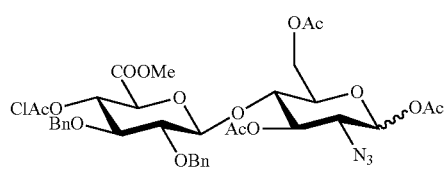

A solution of Intermediate I.44 (324 mg, 0.48 mmol, 1 eq) in acetic anhydride (5 mL, 0.1 M) was cooled to 0° C. and TBSOTf (10 μL, 0.048 mmol, 0.1 eq) was added. After 15 minutes TLC (cyclohexane/ethyl acetate 4:6) showed the formation of the product. The reaction was quenched with TEA and solvent was evaporated under vacuo. The crude was purified via chromatography (cyclohexane/ethyl acetate 80/20 to 40/60) giving 1.45 as α/β mixture 80/20 white foam (272 mg, 0.35 mmol, 73%) (R$_f$ (cyclohexane/ethyl acetate 4:6) 0.65 ¹H NMR (400 MHz, CDCl₃) δ 7.38-7.16 (m, 10H, H Ar), 6.23 (d, J$_{1,2}$=3.7 Hz, 0.80H, H1a), 5.50 (d, J$_{1,2}$=8.6 Hz, 0.20H, H1β), 5.45 (dd, J$_{2,3}$=10.7, J$_{3,4}$=8.9 Hz, 1H, H3), 5.02-5.12 (m, 1H, H4'), 4.79-4.72 (m, 3H, CH₂Ph, CHHPh) 4.59 (d, J=11.8 Hz, 1H, CHHPh), 4.37-4.31 (m, 1H, H6a), 4.34 (d, J$_{1',2'}$=7.8 Hz, 1H, H1'), 4.20 (dd, J$_{6a,6b}$=12.4, J$_{5,6b}$=3.9 Hz, 1H, H6b), 3.87-3.74 (m, 4H, H3', H5, H5', OCHHCl), 3.70 (s, 3H, COOCH₃), 3.68-3.72 (m, 2H, H4, OCHHCl), 3.54 (dd, J$_{2,3}$=10.7, J$_{1,2}$=3.7 Hz, 1H, H2), 3.48 (dd, =9.1, J$_{1',2'}$=7.8 Hz, 1H, H2'), 2.21 (s, 3H, CH₃CO), 2.20 (s, 3H, CH₃CO), 2.04 (s, 3H, CH₃CO) 13c NMR (126 MHz, CDCl₃) δ 170.4 (C=O), 170.2 (C=O), 168.7 (C=O), 167.2 (C'OOMe), 166.1 (COCH₂Cl), 138.0 (C'qBn), 137.8 (C'qBn), 128.5-127.8 (C' Ar), 102.8 (C1'), 92.4 (C1β), 90.0 (C1α), 81.8 (C2'), 81.2 (C4), 76.8 (C5), 75.7 (CH₂Ph), 75.5 (CH₂Ph), 72.6 (C5'), 72.4 (C4'), 71.3 (C3'), 69.8 (C3), 61.4 (C6), 60.5 (C2), 52.9 (COOCH₃), 40.3 (ClCH₂), 21.1 (COCH₃), 20.9 (COCH₃), 20.8 (COCH₃) HR-MS: calc. for C₃₅H₄₀ClN₃O₁₅Na [M+Na⁺]: 800.2046, found 800.2023).

Methyl 2,3-di-O-benzyl-β-D-glucopyranosyl-uronate-(1→4)-2-azido-1,3,6-tri-O-acetyl-2-deoxy-α/β-D-glucopyranose, Intermediate I.46

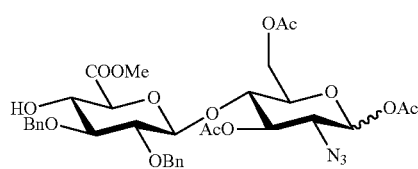

To a solution of the Intermediate I.45 (195 mg, 0.25 mmol, 1 eq) in THF/EtOH 1:1 (2.5 mL, 0.1 M) thiourea (75 mg, 1.0 mmol, 4 eq) was added. The reaction was stirred at 80° C. for 3 hours, then TLC (cyclohexane/ethyl acetate 1:1) showed the full conversion of the starting material into the product. The reaction was evaporated and the crude dissolved in CH₂Cl₂ and washed with water. The organic phase was dried on MgSO₄, filtered and evaporated. The crude was purified via chromatography (cyclohexane/ethyl acetate 7:3→6:4) giving, Intermediate I.46 as α/β mixture 80/20 white solid (140 mg, 0.20 mmol, 80%) (R$_f$: (cyclohexane/ethyl acetate 1:1) 0.43. ¹H NMR (500 MHz, CDCl₃) δ 7.35-7.26 (m, 10H, H Ar), 6.23 (d, J$_{1,2}$=3.7 Hz, 0.80H, H1a), 5.50 (d, J$_{1,2}$=8.5 Hz, 0.20H, H1β), 5.43 (dd, J$_{2,3}$=10.6, J$_{3,4}$=8.3 Hz, 1H, H3), 4.84 (d, J=11.5 Hz, 1H, CHHPh), 4.77-4.74 (m, 3H, CH₂Ph, CHHPh), 4.35 (dd, J$_{6a,6b}$=12.4, J$_{5,6a}$=1.9 Hz, 1H, H6a), 4.32 (d, J$_{1',2'}$=7.7 Hz, 1H, H1'), 4.20 (dd, J$_{6a,6b}$=12.4, J$_{5,6b}$=4.0 Hz, 1H, H6b), 3.80-3.74 (m, 7H, COOCH₃, H4', H5', H4, H5), 3.55 (dd, J$_{2,3}$=10.6, J$_{1,2}$=3.7 Hz, 1H, H2), 3.46 (dd, J$_{2',3'}$=9.2, J$_{3',4'}$=8.3 Hz, 1H, H3'), 3.37 (dd, J$_{1',2'}$=7.7, J$_{2',3'}$=9.2, 1 H, H2'), 2.20 (s, 3H, CH₃CO), 2.11 (s, 3H, CH₃CO), 2.04 (s, 3H, CH₃CO) ¹³C NMR (126 MHz, CDCl₃) δ 170.3 (C=O), 170.2 (C=O), 169.0 (C=O), 168.7 (COOMe), 138.4 (C'qBn), 138.0 (C'qBn), 128.7-127.8 (C Ar), 103.5 (01'), 92.5 (O18), 90.1 (O1a), 83.4 (C3'), 81.6 (C2'), 75.6, 75.54, 75.50, 74.7, 71.7, 71.2 (2 CH₂Ph, C4, C5, C4', C5), 70.0 (C3), 61.5 (C6), 60.5 (C2), 52.7 (COOCH₃), 21.2 (CH₃CO), 21.0 (CH₃CO), 20.8 (CH₃CO) HR-MS: calc. for C₃₃H₃₉N₃O₁₄Na [M+Na⁺]: 724.2330, found 724.2307).

(viii) Synthesis of Disaccharide Building Block DE

Scheme 8

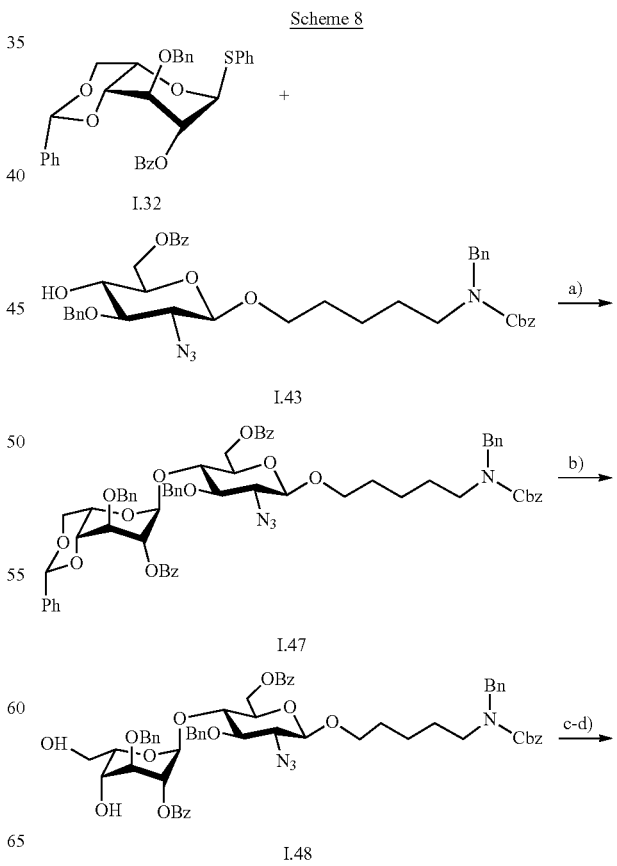

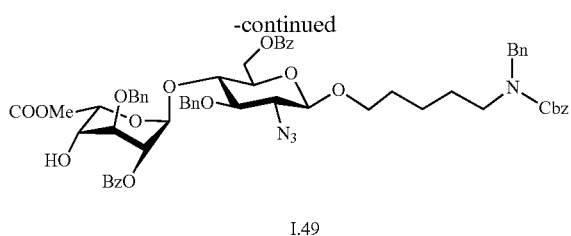

I.49

Reagents and conditions: Synthesis of I.49 a) NIS, AgOTf, CH₂Cl₂, -40° C., 80 min; b) HSEt, p-TsOH·H₂O, CH₂Cl₂, 70% over two steps; c) TEMPO/BAIB, CH₂Cl₂/H₂O 2:1 v/v, rt, 6 h; d) TMSCHN2, Tol/MeOH (1:1 v/v), 0° C., 20 minutes, 50% for two steps.

N-benzyl-N-carboxybenzyl-5-aminopentanyl 2-O-benzoyl-3-O-benzyl-4-α-L-idopyranosyl-(1→4)-2-azido-6-O-benzoyl-3-O-benzyl-2-deoxy-β-D-glucopyranoside Intermediate I.48

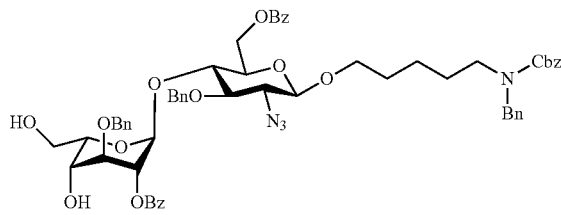

Intermediate I.32 (650 mg, 0.92 mmol, 1 eq) was coevaporated with toluene in the presence of Intermediate I.43-beta (650 mg, 1.17 mmol, 1.3 eq) and dried under vacuum with a stir bar and 1.02 g 4 Å MS for 2 hours before dry CH₂Cl₂ was added. The mixture stirred at room temperature for 45 minutes before cooling to −40° C. NIS (290 mg, 1.29 mmol, 1.4 eq) previously dried under vacuum while protected from light) was then added followed by a catalytic amount of AgOTf (dried under vacuum while protected from light before use). The reaction stirred, gradually warming, until TLC indicated no more donor was present and a new spot had formed at $R_f$=0.7 (Tol/EtOAc, 8/2 v/v). The reaction was quenched by the addition of NEt₃ and the mixture was passed through a pad of celite and diluted until the filtrate ran clear. The solvents were removed under concentration and the remaining crude was purified by column chromatography (2-20% Tol/EtOAc) and the fractions containing the product were combined and concentrated to yield intermediate I.47 as a white foam.

The crude disaccharide 1.47 (900 mg, 0.78 mmol, 1 eq) was dried under vacuum in the presence of p-TsOH·H₂O (22 mg, 0.1 eq) before dissolving in 5 mL dry CH₂Cl₂. HSEt (0.6 mL, 7.8 mmol, 10 eq) was then added at room temperature and the reaction stirred until TLC (3/2 v/v cyclohexane/ethyl acetate) showed major conversion to a lower spot. The reaction was placed on ice and NEt₃ was added to quench. The solvents were removed and the crude syrup was purified by column chromatography (cyclohexane/EtOAc 7/36/4) to give intermediate I.48 (701 mg, 0.66 mmol, 72% for 2 steps) as a white foam. ($R_f$=0.35 (3/2 v/v cyclohexane/EtOAc) HRMS calc for $C_{60}H_{64}N_4O_{14}Na$ [M+Na]+: 1087.4317 Found 1087.4357 ¹H NMR (500 MHz, CDCl₃) δ 7.97 (dd, J=8.2, 1.4 Hz, 2H, Ar), 7.91 (dd, J=8.4, 1.4 Hz, 2H, Ar), 7.57-7.45 (m, 2H, Ar), 7.43-7.11 (m, 24H, Ar), 5.19 (s, 1H, H2'), 5.16 (d, J=10.1 Hz, 2H, NCH₂Bn), 5.11 (s, 1H, H1'), 4.85-4.77 (m, 3H, CH₂Bn×2, H6a), 4.66 (d, J=11.4 Hz, 1H, CH₂Bn), 4.60 (d, J=10.4 Hz, 1H, CH₂Bn), 4.49-4.41 (m, 3H, OCH₂Bn, H6b), 4.33-4.26 (m, 2H, H5', H1), 4.01 (t, J=9.4 Hz, 1H, H4), 3.86-3.77 (m, 2H, H3', CH₂ Linker), 3.70 (d, J=9.1, 2.4 Hz, 1H, H4'), 3.64-3.59 (m, 1H, H5), 3.52-3.28 (m, 5H, H2, H3, H6a', H6b', CH₂ Linker), 3.25-3.16 (m, 2H, Ch₂ Linker), 2.64 (d, J=9.0 Hz, 1H, 4-OH), 1.55 (d, J=58.3 Hz, 4H, CH₂ Linker×2), 1.37-1.22 (m, 2H, CH₂ Linker) ¹³C NMR (126 MHz, CDCl₃) δ 166.03 (Carbonyl), 165.38 (Carbonyl), 138.07 (Ar), 137.78 (Ar), 137.66 (Ar), 133.68 (Ar), 133.23 (Ar), 129.92 (Ar), 129.86 (Ar), 129.82 (Ar), 129.15 (Ar), 128.66 (Ar), 128.64 (Ar), 128.56 (Ar), 128.50 (Ar), 128.28 (Ar), 128.17 (Ar), 128.09 (Ar), 127.96 (Ar), 102.32 (C1), 97.96 (C1'), 81.56 (C3), 75.70 (C3'), 75.62 (CH₂Bn), 73.72 (C4 and C5 overlap), 72.59 (CH₂Bn), 68.45 (C2'), 68.07 (C4'), 67.35 (NCH₂Bn), 67.27 (C5'), 66.83 (C2), 63.04 (C6), 62.84 (C6'), 50.32 (OCH₂Bn), 47.19/46.29 (CH₂ linker rotamer), 29.28 (CH₂ linker), 27.92/27.49 (CH₂ Linker rotamer), 23.27 (CH₂ Linker)).

N-benzyl-N-benzyloxycarbonyl-pentanyl (methyl (2-O-benzoyl-3-O-benzyl-α-L-idopyranosyl)uronate)-(1→4)-2-azido-6-O-benzoyl-3-O-benzyl-2-deoxy-β-D-glucopyranoside, Intermediate I.49

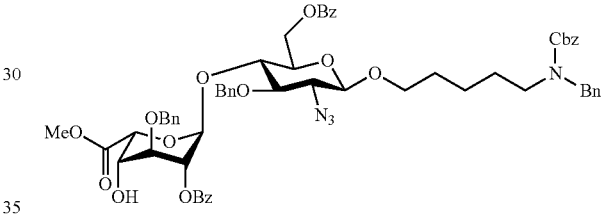

Intermediate I.48 (340 mg, 0.19 mmol, 1 eq) was dissolved in CH₂Cl₂/H₂O (3 mL, 2:1 v/v) with vigorous stirring. TEMPO (10 mg, 0.06 mmol, 0.2 eq) was then added followed by BAIB (258 mg, 0.8 mmol, 2.5 eq). The reaction stirred for 6 hours before quenching with 10 mL aqueous 10% Na₂S₂O₃ solution, stirring for an additional 15 minutes. The mixture was diluted with CH₂Cl₂ and transferred to a separating funnel. The organic layer was put to one side and the aqueous layer was acidified with 1M HCl. The aqueous layer was extracted three additional times with CH₂Cl₂. The combined organic layers were dried on MgSO₄, filtered and concentrated. The crude residue was purified to isolate the carboxylic acid with 2:1 cyclohexane/ethyl acetate→2:1 cyclohexane/ethyl acetate+1% AcOH→1:1 cyclohexane/ethyl acetate+1% AcOH. Fractions containing the carboxylic were combined and concentrated and the residue was coevaporated twice with toluene to remove residual traces of acid before drying under vacuum for 2 hours to give the intermediate acid (190 mg, 0.17 mmol).

The residue was dissolved in 1 mL dry MeOH/dry toluene (1:1 v/v) and cooled on ice. TMSCHN₂ (2M solution in Et₂O, 0.1 mL, 0.19 mmol, 1.1 eq) was then added dropwise. The reaction stirred for 20 minutes before AcOH was added dropwise until no more gas evolved and the solution's colour had faded. The reaction was diluted with additional toluene and the solvents were removed in vacuo and the crude was coevaporated 3 additional times with toluene. The crude was purified using column chromatography (3:1→2:1 cyclohexane/ethyl acetate) to yield intermediate I.49 as a white foam (180 mg, 0.16 mmol, 50% over two steps) ($R_f$=0.28 (2/1 v/v cyclohexane/EtOAc) HRMS: calc for $C_{61}H_{64}N_4O_{15}N$ a [M+Na]$^+$: 1115.4266. Found 1115.4231
$^1$H NMR (400 MHz, CDCl$_3$) δ 8.02-7.98 (m, 2H, Ar), 7.91-7.84 (m, 2H, Ar), 7.57-7.48 (m, 2H, Ar), 7.42-7.22 (m, 22H, Ar), 7.19-7.10 (m, 2H), Ar, 5.34-5.32 (m, H'1), 5.19-5.14 (m, 3H, NCH$_2$Bn, H2'), 5.02 (d, J=2.3 Hz, 1H, H5'), 4.83-4.75 (m, 4H, CH$_2$Bn×3, H6a), 4.69 (d, J=11.6 Hz, 1H, CH$_2$Bn), 4.53-4.39 (m, 3H, OCH$_2$Bn), 4.25 (bs, J=11.6 Hz, 1H, H1), 4.08-4.03 (m, 1H, H4'), 4.00 (m, 1H, H4), 3.92-3.88 (m, 1H, H3'), 3.81 (bs, J=7.1 Hz, 0H), 3.58 (m, 1H, H5), 3.49 (s, 3H, COOMe), 3.46-3.39 (m, 2H, CH$_2$ Linker, H2), 3.34 (t, J=9.3 Hz, 1H, H3), 3.27-3.14 (m, 2H, CH$_2$ Linker), 2.65 (d, J=10.8 Hz, 1H, 4-OH), 1.64-1.47 (m, 4H, CH$_2$ Linker×2), 1.35-1.23 (m, 2H, CH$_2$ Linker) $^{13}$C NMR (101 MHz, CDCl$_3$) δ 169.59 (COOMe), 166.13 (Carbonyl), 165.12 (Carbonyl), 138.04 (Ar), 137.43 (Ar), 133.81 (Ar), 133.19 (Ar), 129.92 (Ar), 129.90 (Ar), 128.88 (Ar), 128.68 (Ar), 128.66 (Ar), 128.65 (Ar), 128.56 (Ar), 128.51 (Ar), 128.37 (Ar), 128.27 (Ar), 128.16 (Ar), 128.03 (Ar), 127.95 (Ar), 127.77 (Ar), 127.61 (Ar), 102.34 (C1), 98.28 (C1'), 81.29 (C3), 75.09 (C4), 74.86 (C3'), 74.80 (CH$_2$Bn), 73.39 (C5), 72.55 (CH$_2$Bn), 69.94 (CH$_2$ Linker), 68.67 (C5'), 68.03 (C2'), 67.93 (C4'), 67.11 (NCH$_2$Bn), 66.41 (C2), 62.98 (C6), 52.21 (COOMe), 50.20 (OCH$_2$Bn), 29.27 (CH$_2$ Linker), 23.27 (CH$_2$ Linker)).

(ix) Synthesis of Trisaccharide Building Block ABC

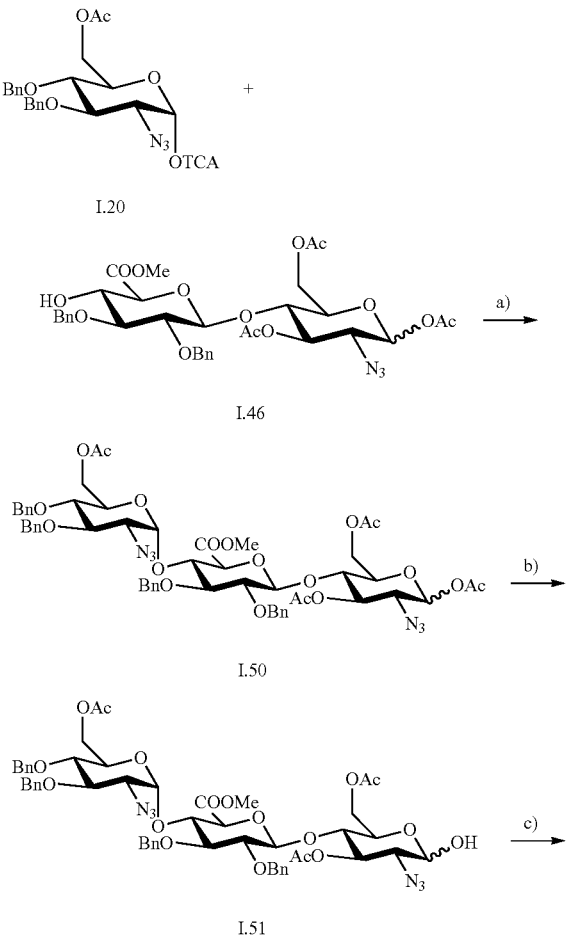

Scheme 9.

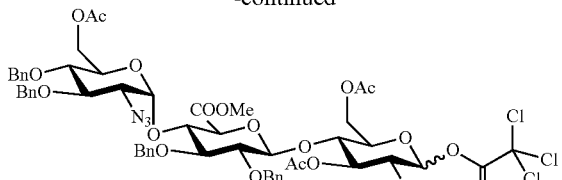

Reagents and conditions: Synthesis of intermediate I.52 a) TBSOTf, dry toluene, 4 Å m.s; -20° C., 1.5 h, 85%; b) EDA, AcOH, THF, 40° C., overnight, 70%; c) Cl$_3$CCN, K$_2$CO$_3$, dry CH$_2$Cl$_2$, overnight, rt, quant.

6-O-acetyl-2-azido-3,4-di-O-benzyl-2-deoxy-α-D-glucopyranosyl-(1→4)-O-(methyl 2,3-di-O-benzyl-β-D-glucopyranosyluronate)-(1→4)-2-azido-1,3,6-triacetyl-2-deoxy-α/β-D-glucopyranose, Intermediate I.50

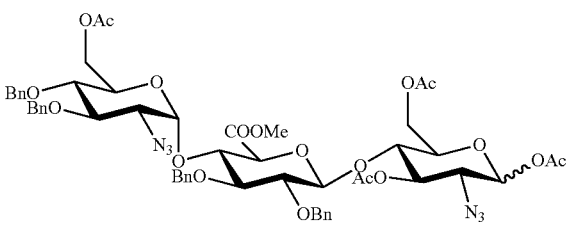

A mixture of trichloroacetimidate I.20 (230 mg, 0.40 mmol, 1.5 eq), intermediate I.46 (190 mg, 0.27 mmol, 1 eq) and freshly activated 4 Å molecular sieves (125 mg) in dry toluene (4 mL) was stirred under N$_2$ atmosphere at room temperature for 30 min. The solution was cooled to -20° C. and TBSOTf (31 μL, 0.135 mmol, 0.5 eq) was added dropwise. The resulting solution was stirred for 1 hour and 30 min, attaining room temperature, then TEA was added to quench the reaction. The whole mixture was filtered through Celite and evaporated in vacuo. The crude was purified by automated flash chromatography (cyclohehane/ethyl acetate 80/20 to 60/40) to get the trisaccharide I.50 (257 mg, 0.23 mmol, 85%) as a white foam (R$_f$ (cyclohexane/ethyl acetate 7:3) 0.55 $^1$H NMR (500 MHz, CDCl$_3$) δ 7.49-7.01 (m, 20H, H Ar), 6.22 (d, J$_{1,2}$=3.6 Hz, 0.8H, H1a), 5.50 (d, J$_{1'',2''}$=3.7 Hz, 1H, H1''), 5.49 (d, J$_{1,2}$=8.3 Hz, 0.2H, H1β), 5.42 (dd, J$_{2,3}$=10.7, J=8.7 Hz, 1H, H3), 4.95 (d, J=10.9 Hz, 1H, CHPh), 4.87-4.77 (m, 5H, 2 CH$_2$Ph, CHPh), 4.71 (d, J=11.5 Hz, 1H, CHPh), 4.55 (d, J=11.0 Hz, 1H, CHPh), 4.34 (d, J$_{1',2'}$=7.8 Hz, 1H, H1'), 4.33-4.31 (m, 1H, H6a), 4.30-4.24 (m, 1H, H6a''), 4.21-4.16 (m, 1H, H6b''), 4.17-4.11 (m, 1H, H6b), 4.06 (dd, J=9.8, J$_{4',5}$=8.8 Hz, 1H, H5'), 3.88-3.83 (m, 2H, H3'', H4), 3.78 (dd, J=3.8, 1.9 Hz, 1H, H5), 3.77 (s, 3H, COOCH$_3$), 3.74 (d, J$_{2',3'}$=9.1 Hz, 1H, H3'), 3.71 (d, J$_{4',5'}$=8.9 Hz, 1H, H4'), 3.54 (dd, J$_{2,3}$=10.7, J$_{1,2}$=3.6 Hz, 1H, H2), 3.50 (m, 2H, H4'', H5''), 3.44 (dd, J$_{2',3'}$=9.1, J$_{1',2'}$=7.8 Hz, 1H, H2'), 3.28 (dd, J$_{2'',3''}$=10.3, J$_{1'',2''}$=3.7 Hz, 1H, H2''), 2.20 (s, 3H, CH$_3$CO), 2.10 (s, 3H, CH$_3$CO), 2.07 (s, 3H, CH$_3$CO), 2.03 (s, 3H, CH$_3$CO) $^{13}$C NMR (126 MHz, CDCl$_3$) δ 170.8 (C=O), 170.3 (2 C=O), 168.8 (C=O), 168.5 (C'OOMe), 138.1 (CqBn), 137.8 (CqBn), 137.6 (2 CqBn), 128.6-127.4 (Ar), 103.2 (C1'), 97.7 (C1''), 90.1 (C1α), 84.0 (C4'), 82.2 (C2'), 80.2 (C4), 77.5 (C5'' or C4''), 75.6, 75.5, 75.4, 75.3, 75.11, 75.08, 74.5 (4 CH$_2$Ph, C5', C3', C3'') 71.1 (C5), 70.0

(C5″ or C4″), 69.8 (C3), 63.4 (C2″), 62.3 (C6″), 61.4 (C6), 60.5 (C2), 52.8 (COOCH$_3$'), 27.1 (CH$_3$CO), 21.2 (CH$_3$CO), 21.0 (CH$_3$CO), 20.9 (CH$_3$CO), 20.8 (CH$_3$CO) HR-MS: calc. for C$_{55}$H$_{62}$N$_6$O$_{19}$Na [M+Na$^+$]: 1133.3967, found 1133.3967).

6-O-Acetyl-2-azido-3,4-di-O-benzyl-2-deoxy-α-D-glucopyranosyl-(1→4)-(methyl 2,3-di-O-benzyl-β-D-glucopyranosyluronate)-(1→4)-2-azido-3,6-di-acetyl-2-deoxy-α/β-D-glucopyranose, Intermediate I.51

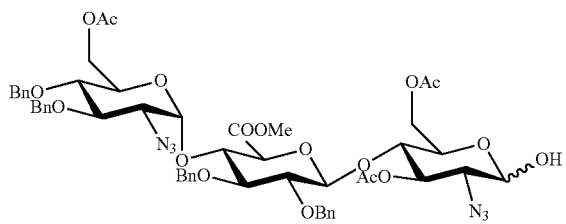

Trisaccharide I.50 (108 mg, 0.097 mmol, 1 eq) was dissolved in THF (0.1 M) and ethylediamine (7.7 μl, 0.116 mmol, 1.2 eq) and acid acetic (6.6 μl, 0.116 mmol, 1.2 eq) were added. Reaction was stirred at 40° C. overnight, then it was diluted with CH$_2$Cl$_2$ and washed with HCl 1 M. The aqueous phase was extracted twice with CH$_2$Cl$_2$. The combined organic layers were washed with NaHCO$_3$ aq sat and Brine, dried over MgSO$_4$ and evaporated. The crude was purified by automatic chromatography (cyclohexane/ethyl acetate 80/20→40/60) achieving Intermediate I.51 in α/β mixture (73 mg, 0.068 mmol, 70%) as a white foam (R$_f$ (cyclohexane/ethyl acetate 6:4) 0.34 $^1$H NMR (500 MHz, CDCl$_3$) δ 7.42-7.26 (m, 20H, H Ar), 5.17 (d, J$_{1,2}$=3.6 Hz, 1H, H1), 5.10 (d, J$_{1,2}$=3.7 Hz, 1H, H1), 4.94-4.82 (m, 6H, 3 CH$_2$Ph), 4.63-4.55 (m, 2H, CHPh), 4.41 (d, J$_{1',2'}$=7.9 Hz, 1H, H1'), 4.38 (dd, J$_{6a,6b}$=12.0, J$_{6a,5}$=1.7 Hz, 1H, H6a), 4.32 (dd, J$_{6a″,6b″}$=12.1, J$_{6a″,5″}$=2.2 Hz, 1H, H6a″), 4.29-4.21 (m, 1H, H6b″), 4.16 (dt, J=10.5, 2.7 Hz, 1H), 4.08-4.02 (m, 1H, H6b), 4.00 (dd, J=10.1, 9.0 Hz, 1H), 3.65 (dd, J=10.3, 8.8 Hz, 1H), 3.59 (dd, J=10.1, 8.9 Hz, 1H), 3.55 (dd, J=10.2, 3.8 Hz, 1H), 3.51-3.41 (m, 4H), 2.05 (s, 3H, CH$_3$CO), 2.04 (s, 3H, CH$_3$CO), 2.01 (s, 3H, CH$_3$CO)).

6-O-Acetyl-2-azido-3,4-di-O-benzyl-2-deoxy-α-D-glucopyranosyl-(1→4)-methyl 2,3-di-O-benzyl-β-D-glucopyranosyluronate-(1→4)-3,6-di-O-acetyl-2-azido-2-deoxy-α/β-D-glucopyranosyl trichloroacetimidate, Intermediate I.52

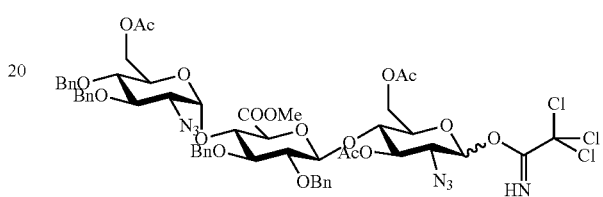

Trichloroacetonitrile (0.460 mL, 1.6 mmol, 10 eq) was added to a solution of Intermediate I.51 (170 mg, 0.16 mmol, 1 eq) and K$_2$CO$_3$ (110 mg, 0.80 mmol, 5 eq) in dry CH$_2$Cl$_2$ (8 mL, 0.1 M) under N$_2$ atmosphere. The mixture was stirred overnight at room temperature, then filtered on a celite pad and evaporated in vacuo. The product, intermediate I.52 obtained as α/β mixture was directly used in the next glycosylation step without further purification. (TLC analysis cyclohexane/ethyl acetate 6:4 ESI-MS: calc. for C$_{55}$H$_{60}$Cl$_3$N$_7$O$_{18}$ [M]: 1211.31, found 1235.58).

(x) Synthesis of Protected Pentasaccharide with Linker

Scheme 10.

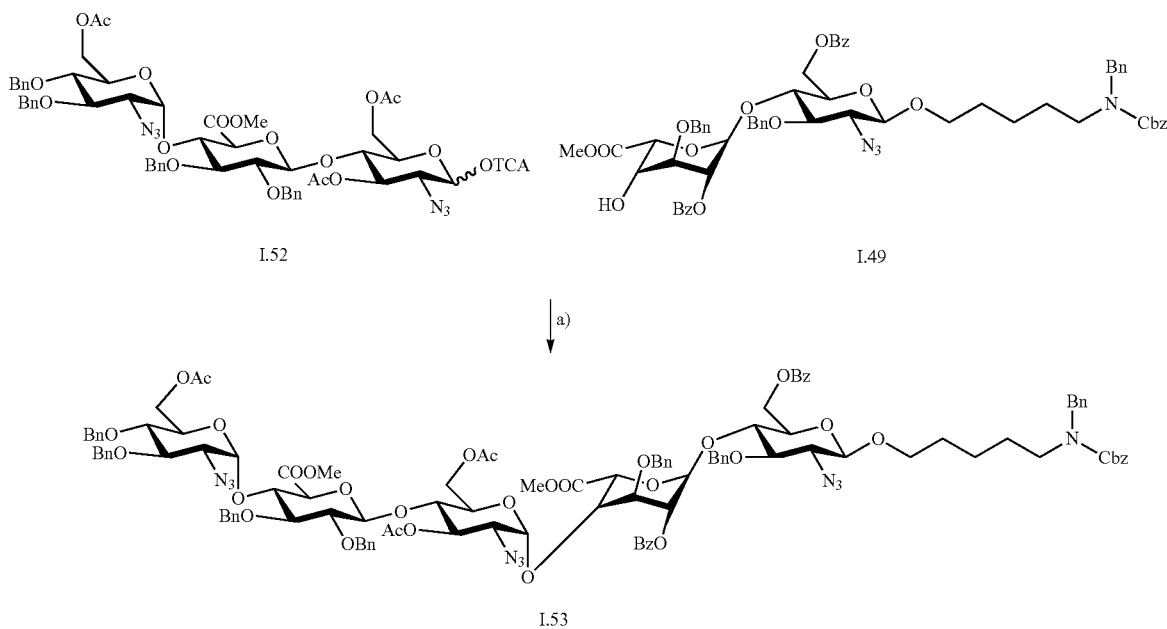

Reagents and conditions: Synthesis of intermediate I.53 a) TfOH 0.1M in dry toluene molecular sieves 4 Å, dry toluene, -40° C.;

N-(Benzyl)-benzyloxycarbonyl-5-aminopentyl 6-O-Acetyl-2-azido-3,4-di-O-benzyl-2-deoxy-α-D-glucopyranosyl-(1→4)-methyl 2,3-di-O-benzyl-β-D-glucopyranosyluronate-(1→4)-3,6-di-O-acetyl-2-azido-2-deoxy-α-D-glucopyranosyl-(1→4)-methyl 2-O-benzoyl-3-O-benzyl-α-L-idopyranosyluronate-(1→4)-2-azido-6-O-benzoyl-3-benzyl-2-deoxy-β-D-glucopyranoside, Intermediate I.53

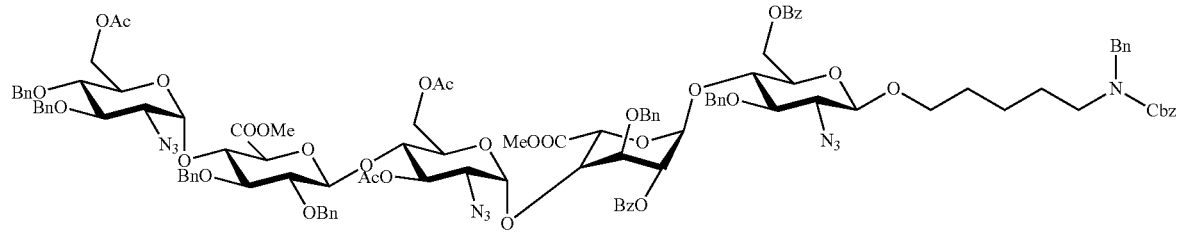

A mixture of intermediate I.52 (85 mg, 0.07 mmol, 1.5 eq), intermediate I.49 (50 mg, 0.046 mmol, 1 eq) and freshly activated 4 Å molecular sieves (65 mg) in dry toluene (2 mL) was stirred under $N_2$ atmosphere at room temperature for 30 min. The solution was cooled to −40° C. and TfOH 0.1 M in dry toluene (0.230 mL, 0.023 mmol, 0.5 eq) was added dropwise. The resulting solution was stirred for 1 hour, during in which the temperature was increased to 5° C., and TEA was added to quench the reaction. The whole mixture was filtered through Celite and concentrated under reduced pressure to get the crude product, which was purified by column chromatography (toluene/acetone 98/2 to 96/4) to get the intermediate I.53 (45 mg, 0.02 mmol, 56%) as a white solid ($R_f$ (toluene/acetone 9:1) 0.51 $^1$H NMR (500 MHz, CDCl$_3$) δ 8.06 (d, J=7.2 Hz, 2H), 7.98 (d, J=7.2 Hz, 2H), 7.55-7.12 (m, 36H, H Ar), 5.68 (d, $J_{1,2}$=5.6 Hz, 1H, H1B), 5.50 (d, $J_{1,2}$=3.8 Hz, 1H, H1E), 5.34-5.27 (m, 1H, H3O), 5.23 (t, J=6.0 Hz, 1H, H2B), 5.15 (br d, J=6.8 Hz, 2H, CH$_2$Cbz), 5.07 (d, $J_{1,2}$=3.6 Hz, 1H, H1C), 4.97 (d, J=10.8 Hz, 1H, CHPh), 4.91-4.74 (m, 6H, CH$_2$Ph), 4.72 (s, 2H, CH$_2$Ph), 4.67 (d, J=5.0 Hz, 1H, H3B), 4.64 (d, J=11.2 Hz, 1H, CHPh), 4.60 (dd, $J_{6a,6b}$=12.1, $J_{6a,5}$=2.2 Hz, 1H, H6), 4.55 (d, J=11.0 Hz, 1H, CHPh), 4.48-4.37 (m, 4H, NCH$_2$Bn, H6, H6E), 4.33 (d, $J_{1,2}$=7.8 Hz, 1H, H1D), 4.29-4.22 (m, 1H, H6), 4.22-4.13 (m, 5H, H1A, H6E, HB, H6, HA), 4.06-3.99 (m, 3H, H4D, HB, H5E), 3.99-3.94 (m, 1H, H5C), 3.87-3.82 (m, 2H, HSD, H3E), 3.74 (s, 3H, CH$_3$OD), 3.71-3.65 (m, 3H, H3D, H4C, OCH), 3.51 (s, 3H, CH$_3$O B), 3.50-3.48 (m, 2H, H4E, HA), 3.44-3.33 (m, 4H, H2D, HA, H2A, OCH), 3.26 (dd, $J_{2,3}$=10.4, $J_{1,2}$=3.8 Hz, 1H, H2E), 3.20 (dd, $J_{2,3}$=10.8, $J_{1,2}$=3.6 Hz, 1H, H2C), 3.18-3.11 (m, 2H, NCH$_2$), 2.03 (s, 3H, CH$_3$CO), 2.02 (s, 3H, CH$_3$CO), 2.02 (s, 3H, CH$_3$CO), 1.59-1.43 (m, 4H, 2 CH$_2$), 1.34-1.22 (m, 2H, CH$_2$) $^{13}$C NMR (126 MHz, CDCl$_3$) δ 170.77, 170.23, 170.07, 169.77, 168.46, 166.11, 165.49, 138.16, 138.14, 137.66, 137.65, 137.47, 137.44, 130.02, 129.95, 129.17, 129.12, 128.7 to 125.4 (Ar), 103.4 (C1D), 102.0 (C1A), 98.3 (C1B), 97.7 (20, C1E and C1C), 83.85, 81.83, 80.26, 77.51, 77.37, 76.34, 75.66, 75.4 (CH$_2$Ph), 75.3 (CH$_2$Ph), 75.2 (CH$_2$Ph), 75.1 (CH$_2$Ph), 74.53, 74.45, 73.29, 73.22, 72.0 (C2B), 71.4 (CB), 69.8 (OCH$_2$), 69.7, 69.4 (C3C), 67.3 (CH$_2$Cbz), 66.2 (C2A), 63.3 (C2E), 62.3 (C6), 62.1 (C6), 61.3 (C6E), 60.8 (C2C), 52.8 (CH$_3$OD), 52.4 (CH$_3$O B), 46.1 (NCH$_2$) 23.22, 20.98 (CH$_3$CO), 20.96 (CH$_3$CO), 20.77 (CH$_3$CO)).

(xi) Synthesis of Pentasaccharide with Linker

Scheme 11.

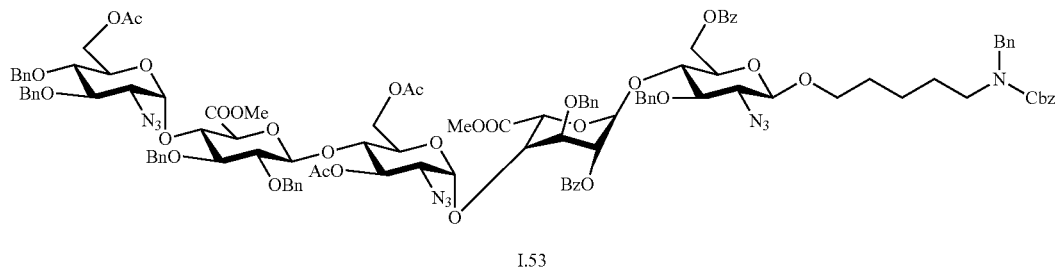

I.53

↓ a)

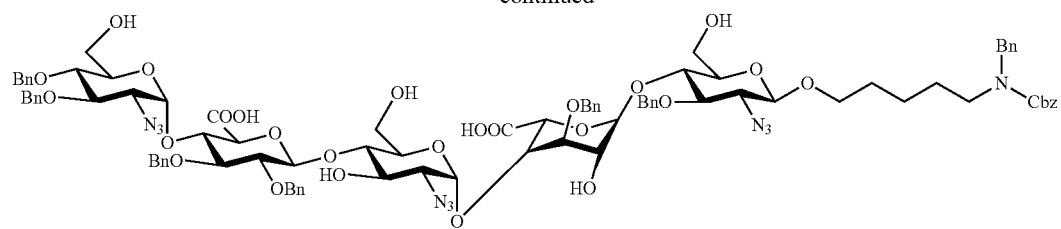
I.54
↓ b)
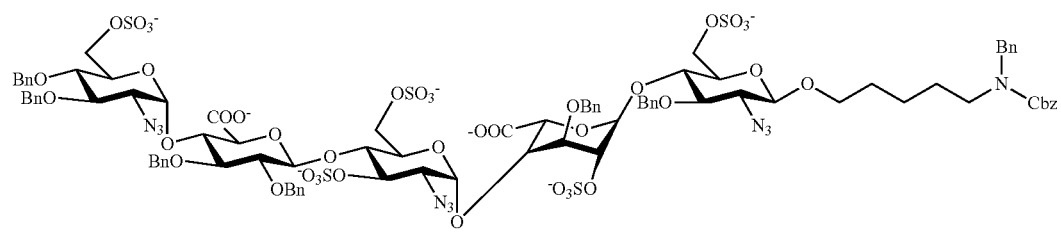
I.55
↓ c)
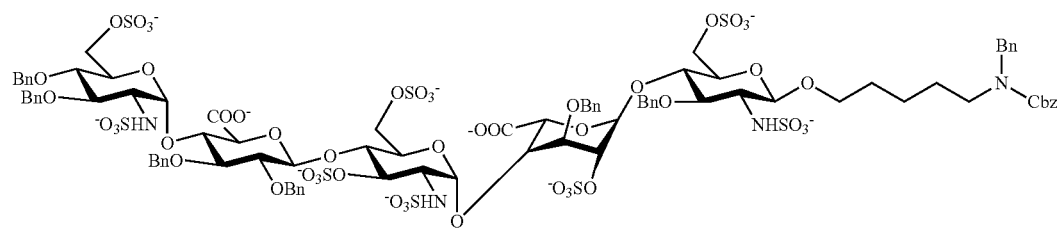
I.56
↓ d)
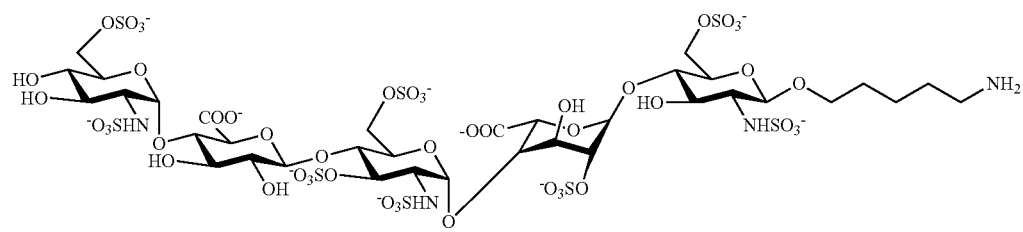
1.1
Reagents and conditions: Synthesis of Example 1.1 a) NaOH 5M in $H_2O$, $CH_3OH$, $CH_2Cl_2$, rt, 80%; b) $SO_3 \cdot NMe_3$, DMF, MW 100° C. c) i. $PMe_3$ 1M in THF, NaOH 1M in $H_2O$, THF, rt; ii. $SO_3 \cdot Py$, Py, TEA, rt; d) $H_2$, Pd/C, Pd(OH)$_2$, EtOH/$H_2O$.

N-(Benzyl)-benzyloxycarbonyl-5-aminopentyl 2-azido-3,4-di-O-benzyl-2-deoxy-α-D-glucopyranosyl-(1→4)-2,3-di-O-benzyl-β-D-glucopyranosyluronic acid-(1→4)-2-azido-2-deoxy-α-D-glucopyranosyl-(1→4)-3-O-benzyl-α-L-idopyranosyluronic acid-(1→4)-2-azido-3-benzyl-2-deoxy-β-D-glucopyranoside, Intermediate I.54

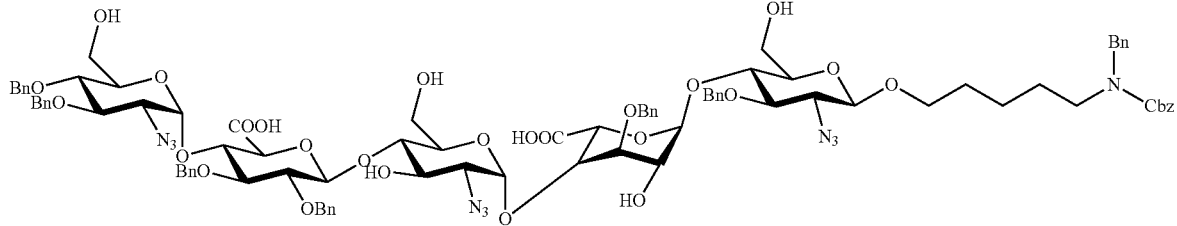

Intermediate I.53 (32 mg, 0.015 mmol, 1 eq) was dissolved in a mixture of methanol/dichloromethane (1 mL/0.73 mL) and 0.35 mL of NaOH 5 M in H₂O were added dropwise. The reaction was stirred at room temperate overnight, then diluted with $CH_2Cl_2$ and washed with HCl 1 M. The aqueous phase was extracted twice with $CH_2Cl_2$. The combined organic phase was dried on $MgSO_4$ and evaporated in vacuo. The crude was dissolved with $CH_2Cl_2$/$CH_3OH$ 1:1 and layered on top of a Sephadex LH-20, which was eluted with the same eluent mixture. Fractions were collected by means of an automated collector every 3 min. Fractions containing the product were evaporated under vacuum giving Intermediate I.54 as a white solid (22.5 mg, 0.012 mmol, 80%) ($R_f$ (dichloromethane/methanol 9:1) 0.40 ¹H NMR (500 MHz, $CD_3OD$) δ 7.42 (d, J=7.2 Hz, 2H), 7.45-7.12 (m, 38H, H Ar), 5.53 (d, $J_{1,2}$=3.8 Hz, 1H, H1E), 5.30 (br s, 1H, H1B), 5.14 (brd, J=17.6 Hz, 2H, $CH_2Cbz$), 5.11 (d, $J_{1,2}$=3.8 Hz, 1H, H1C), 4.97 (d, J=10.8 Hz, 1H, CHPh), 4.93 (d, J=11.2 Hz, 1H, CHPh), 4.91-4.74 (m, H, CHPh), 4.73-4.61 (m, 5H, H1 D, 2 $CH_2Ph$), 4.57 (d, J=11.0 Hz, 1H, CHPh), 4.49 (s, 2H, $NCH_2Bn$), 4.30 (br dd, J=28.9, 7.9 Hz, 1H, H1A), 4.12-3.62 (m, 16H, 6H6, OCH, H2B, H3A, H3B, H3C, H3D, H3E, H4C, H4D, H5D) 3.50-3.21 (m, 10H, OCH, H2D, H2E, H2C, H2A, $NCH_2$), 1.64-1.45 (m, 4H, $2CH_2$), 1.38-1.31 (m, 2H, $CH_2$) ¹³C NMR (126 MHz, $CD_3OD$) 139.9, 139.75, 139.71, 139.58, 139.52 (CqBn), 129.6 to 128.3 (Ar), 103.6 (C1D), 103.2 (C1A), 102.2 (C1B), 99.1 (C1E), 98.3 (C1C), 85.6, 83.3, 82.6, 81.1, 79.8 (C2D), 79.7 (C2B), 77.8, 76.6, 76.1 (3×$CH_2Ph$), 75.7 ($CH_2Ph$), 74.5 ($CH_2Ph$), 73.0, 71.4, 70.5 ($OCH_2$), 68.5 ($CH_2Cbz$) 68.0 (C2A), 65.1 (C2C), 65.0 (C2E), 61.7 (C6), 60.8 (C6), 60.7 (C6), 47.8 ($NCH_2$), 30.2 ($CH_2$), 28.8 ($CH_2$), 24.2 ($CH_2$) ESI-MS: calc. for $C_{92}H_{102}N_{10}O_{27}{}^{2-}$ [M]: 1778.69, found 1778.44).

N-(Benzyl)-benzyloxycarbonyl-5-aminopentyl 2-azido-3,4-di-O-benzyl-2-deoxy-6-O-sulfo-α-D-glucopyranosyl-(1→4)-2,3-di-O-benzyl-β-D-glucopyranosyluronic acid-(1→4)-2-azido-2-deoxy-3,6-di-O-sulfo-α-D-glucopyranosyl-(1→4)-3-O-benzyl-2-O-sulfo-α-L-idopyranosyluronic acid-(1→4)-2-azido-3-benzyl-2-deoxy-6-O-sulfo-β-D-glucopyranoside, Intermediate I.55

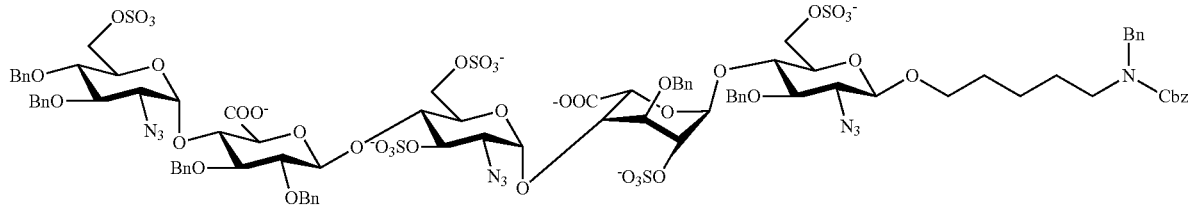

Intermediate I.54 (19 mg, 0.01 mmol, 1 eq) was dissolved in dry DMF (1 mL) and placed into a microwave vial together with $SO_3·NMe_3$ (42 mg, 0.30 mmol, 30 eq) previously dried at Schlenck. Reaction was carried out into the microwave reactor at 100° C. for 2 hours. Then reaction was quenched with TEA, filtered through a 22 μm pore filter and layered on top of a Sephadex LH-20, which was eluted with $CH_2Cl_2$/$CH_3OH$ (1:1) recovering a triethylamine salt of intermediate I.55 as a slight yellow solid (25 mg) ($R_f$ (dichloromethane/methanol/ammonium hydroxide (7:3:1) 0.34) ¹H NMR (500 MHz, $CD_3OD$) δ 7.50-7.15 (m, 40H, H Ar), 5.53 (d, $J_{1,2}$=3.9 Hz, 1H, H1E), 5.41 (brs, 1H, H1B), 5.26 (d, $J_{1,2}$=3.8 Hz, 1H, H1C), 5.15 (brd, J=20.0 Hz, 2H, $CH_2Cbz$), 5.05-4.63 (m, 16H, H1D, H3C, 1H, 5 $CH_2Ph$), 4.55-4.45 (m, 7H, H2B, 2H6, $CH_2Ph$, $NCH_2Bn$), 4.40-4.10 (m, 8H, 4H6, H1A, H3A, 2H), 4.08-3.88 (m, 6H, H4C, 5H), 3.89-3.83 (m, 1H, OCH), 3.80 (t, J=8.7 Hz, 1H), 3.66-3.58 (m, 3H, H2D, 2H), 3.52 (dd, $J_{2,3}$=10.0, $J_{1,2}$=3.7 Hz, 1H, H2C), 3.45-3.39 (m, 1H, OCH), 3.38-3.19 (m, 5H, H2A, H2E, $NCH_2$, H), 1.68-1.43 (m, 4H, $2CH_2$), 1.41-1.25 (m, 2H, $CH_2$) ¹³C NMR (126 MHz, $CD_3OD$) δ 158.5 (C=O), 157.9 (C=O), 140.2, 139.7, 139.4, 139.3, 139.2, 138.1 (6 CqBn), 129.8 to 128.4 (Ar), 102.9 (C1A), 102.8 (C1D), 99.6 (C1B), 98.7 (C1E), 96.0 (C1C), 85.6, 83.5 (C2D), 82.7, 81.2, 79.3, 78.3 (C3C), 77.2, 76.3 (ChPh), 76.0 (ChPh), 75.9 (ChPh), 75.8 (ChPh), 74.98, 74.85, 74.0 (C3A), 73.9 (C2B), 71.3 (C4), 71.2, 70.4 (00H2), 68.4 ($CH_2Cbz$), 68.2 (C2A), 67.4 (C6), 66.98 (C6), 66.5 (C6), 64.9 (C2E), 64.4 (C2C), 51.5 ($NHCH_2Bn$), 47.6 ($NCH_2$), 30.2 ($CH_2$), 28.8 ($CH_2$), 24.2 ($CH_2$)).

N-(Benzyl)-benzyloxycarbonyl-5-aminopentyl 3,4-di-O-benzyl-2-deoxy-2-sulfamido-6-O-sulfo-α-D-glucopyranosyl-(1→4)-2,3-di-O-benzyl-β-D-glucopyranosyluronic acid-(1→4)-2-deoxy-2-sulfamido-3,6-di-O-sulfo-α-D-glucopyranosyl-(14)-3-O-benzyl-2-O-sulfo-α-L-idopyranosyluronic acid-(1→4)-3-benzyl-2-deoxy-2-sulfamido-6-O-sulfo-β-D-glucopyranoside, Intermediate I.56

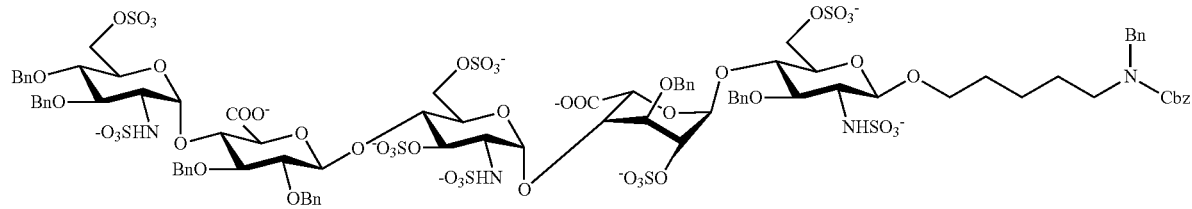

Intermediate I.55 (21 mg, 0.01 mmol, 1 eq) was dissolved in THF (0.5 mL) and treated with NaOH 1M in H$_2$O (0.24 mL, 0.24 mmol, 24 eq). PMe$_3$ 1M in THF (0.30 mL, 0.30 mmol, 30 eq) was added and the reaction was stirred at room temperature overnight. Reaction was quenched with HCl 1 M and evaporated. The crude was dissolved in CH$_2$Cl$_2$/CH$_3$OH 1:1 mixture and layered on top of a Sephadex LH-20, which was eluted with the same eluent mixture. The fractions containing the product were evaporated under vacuum. The amino derivative obtained was dissolved in dry pyridine and TEA and SO$_3$·Py (43 mg, 0.27 mmol, 30 eq) was added in 4 portions. Reaction was left under stirring overnight, then it was diluted with CH$_2$Cl$_2$/CH$_3$OH 1:1 mixture and layered on top of a Sephadex LH-20, which was eluted with the same eluent mixture, intermediate I.56 was obtained as triethylamine salt (24 mg) (R$_f$(dichloromethane/methanol/ammonium hydroxide 7:3:1.2) 0.31)

5-aminopentyl 2-deoxy-2-sulfamido-6-O-sulfo-α-D-glucopyranosyl-(14)-β-D-glucopyranosyluronic acid-(1→4)-2-deoxy-2-sulfamido-3,6-di-O-sulfo-α-D-glucopyranosyl-(1→4)-2-O-sulfo-α-L-idopyranosyluronic acid-(1→4)-2-deoxy-2-sulfamido-6-O-sulfo-β-D-glucopyranoside (Example 1.1)

Intermediate I.56 (29 mg, 0.012 mmol, 1 eq) dissolved in EtOH/H$_2$O 1:1 (1 mL) was hydrogenated in presence of Pd/C (30 mg) and Pd(OH)$_2$ (30 mg). Reaction was carried out in the hydrogenator reactor at 25 bar pressure for 48 h. The suspension was filtered through a 22 μm pore filter and concentrated. The crude was dissolved in water, stirred for 1 h with DOWEX Na$^+$ and after filtration the solvent was evaporated. The crude was purified by reverse phase (H$_2$O/ACN 9:1). Example 1.1 was obtained as a white solid after freeze drying (14 mg, 0.009 mmol, 75%) (R$_f$(Ethyl acetate/methanol/water 4:3:3) 0.32 $^1$H NMR (600 MHz, D$_2$O) β 5.64 (d, J$_{1,2}$=3.8 Hz, 1H), 5.54 (d, J$_{1,2}$=3.5 Hz, 1H), 4.63 (dd, J=8.6, J$_{1,2}$=3.4 Hz, 1H, H1), 4.58 (d, J$_{1,2}$=8.1 Hz, 1H, H1), 4.53 (d, J$_{1,2}$=8.0 Hz, 1H, H1), 4.50 (d, J=11.0 Hz, 1H, H6), 4.43-4.33 (m, 4H, 2H6, H6, 1H) 4.32 (dd, J=7.7, 3.3 Hz, 1H), 4.28 (d, J=10.8 Hz, 1H, H6), 4.22-4.12 (m, 4H, H6, 3H), 4.03-3.96 (m, 1H), 3.94-3.66 (m, 7H, OCH$_2$, 6H), 3.65-3.56 (m, 2H), 3.55-3.38 (m, 4H, H2, H2, 2H)), 3.33 (dd, J=9.5, 8.0 Hz, 1H, H2), 3.27 (dd, J=10.0, 3.8 Hz, 1H, H2), 3.08 (m, 1H, H2), 1.79-1.64 (m, 4H, 2CH$_2$), 1.57-1.47 (m, 2H, CH$_2$) $^{13}$C NMR (151 MHz, D$_2$O) δ 102.4 (C1), 101.5 (C1), 101.0 (C1), 97.4 (C1), 95.8 (C1), 79.0, 76.7, 76.1, 75.9, 75.8, 75.4, 73.1 (C2), 72.8, 72.7 (C2), 72.5, 71.0, 70.9, 70.3, 69.9 (OCH$_2$), 69.6, 69.5, 69.4, 68.8, 66.8 (C6), 66.2 (C6), 65.9 (C6), 60.1 (C2), 58.0 (C2), 56.6 (C2), 27.9 (CH$_2$), 26.1 (CH$_2$), 22.0 (CH$_2$))

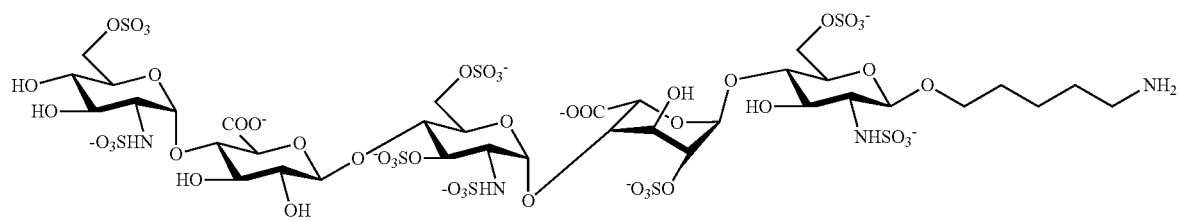

Example 1.2, 5-Aminopentyl 2-deoxy-2-sulfamido-6-O-sulfo-α-D-glucopyranosyl-(1→4)-β-D-glucopyranosyluronic acid-(1→4)-2-deoxy-2-sulfamido-3,6-di-O-sulfo-α-D-glucopyranosyl-(1→4)-2-O-sulfo-α-L-idopyranosyluronic acid-(1→4)-2-deoxy-2-sulfamido-6-O-sulfo-α-D-glucopyranoside

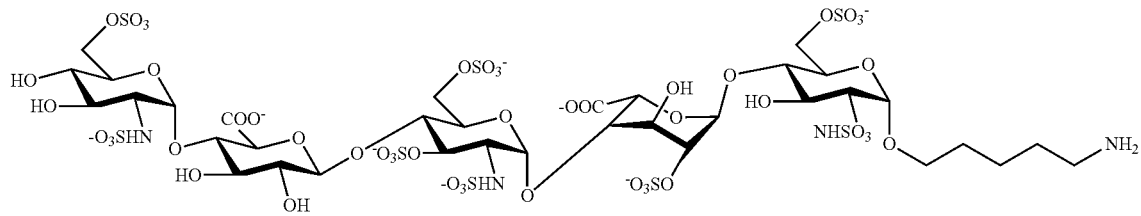

Example 1.2 was obtained utilizing the same synthetic route as in the preparation of example 1.1 but replacing I.43-β with I.43-α

$^1$H NMR (600 MHz, Deuterium Oxide) δ 5.62 (d, J=3.8 Hz, 1H), 5.56 (d, J=3.4 Hz, 1H), 5.28 (s, 1H), 5.15 (d, J=3.6 Hz, 1H), 4.65 (d, J=8.3 Hz, 1H), 4.49 (d, J=11.4 Hz, 1H), 4.41-4.33 (m, 6H), 4.32-4.29 (m, 2H), 4.21-4.12 (m, 4H), 3.65-3.56 (m, 3H), 3.51-3.41 (m, 2H), 3.32-3.26 (m, 1H), 3.08-3.03 (m, 2H), 1.81-1.67 (m, 4H), 1.53-1.48 (m, 2H).

Example 1.3: Methyl 4-O-(5'-aminopentanyl)-2-deoxy-2-sulfamido-6-O-sulfo-α-D-glucopyranosyl-(1→4)-β-D-glucopyranosyluronic acid-(1→4)-2-deoxy-2-sulfamido-3,6-di-O-sulfo-α-D-glucopyranosyl-(1→4)-2-O-sulfo-α-L-idopyranosyluronic acid-(1→4)-2-deoxy-2-sulfamido-6-O-sulfo-α-D-glucopyranoside

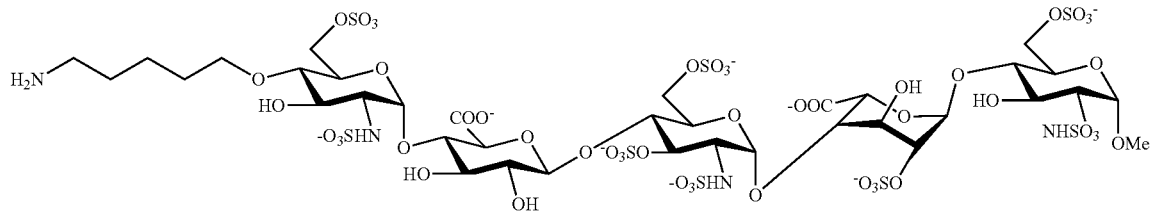

Figure 9:
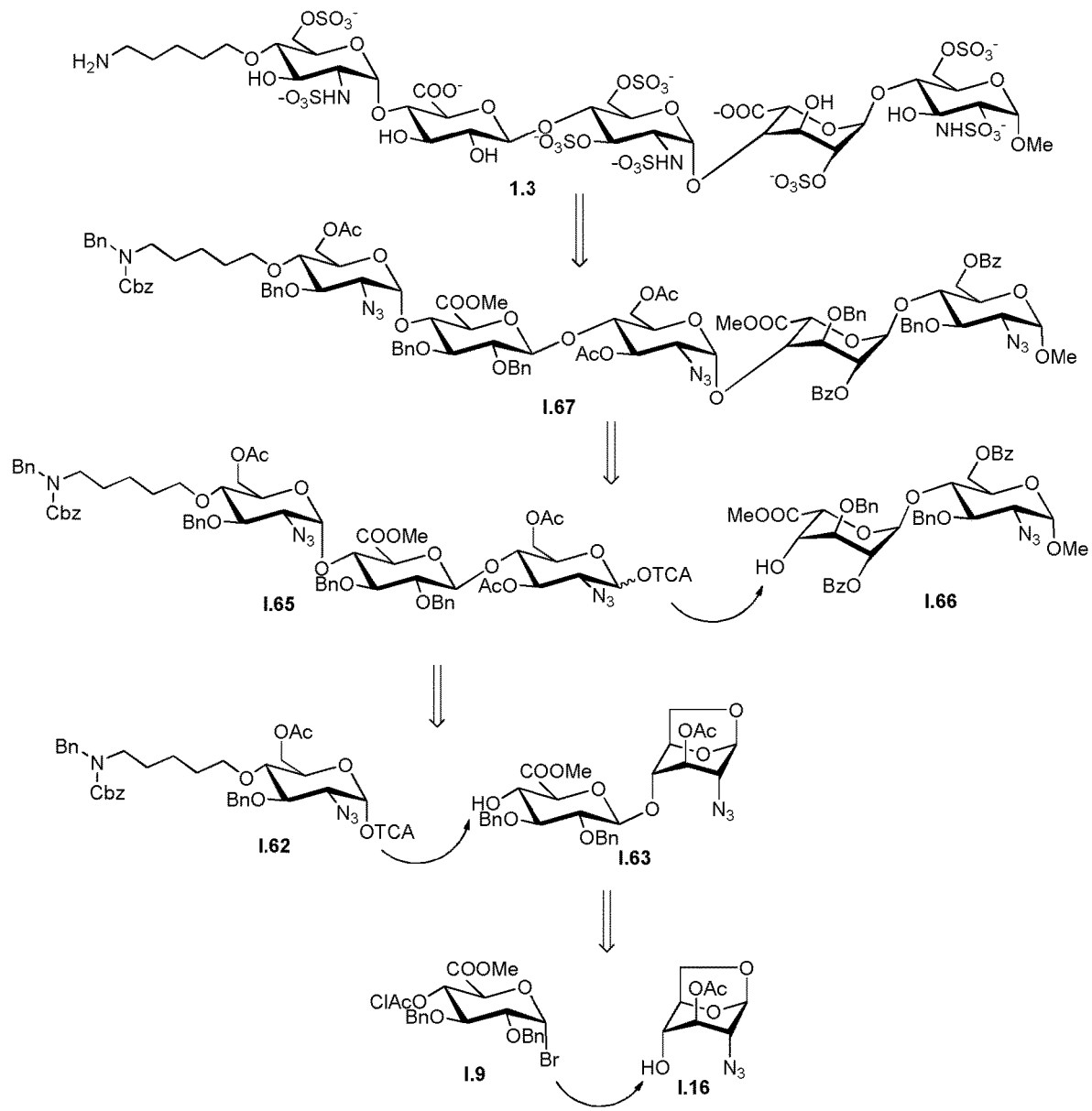
FIG. 9: Retrosynthetic scheme of a pentasaccharide with a linker synthetically incorporated at the non-reducing end

An overview of a synthetic route to this molecule is shown in FIG. 9.

(i) Synthesis of Building Block with Linker at Non-Reducing End

Scheme 12

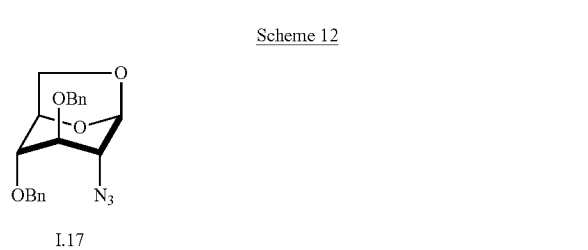

-continued

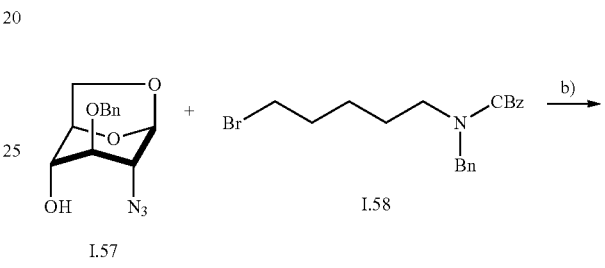

-continued

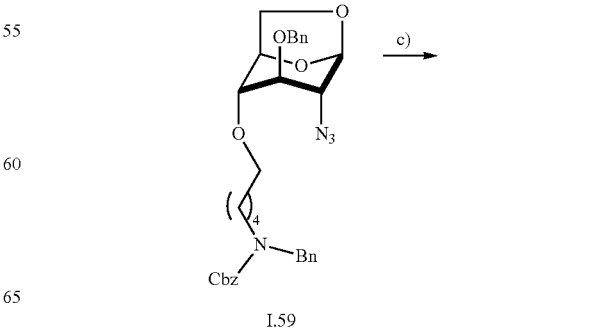

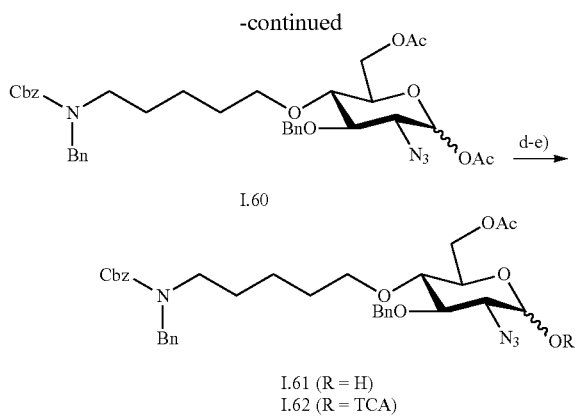

I.60

I.61 (R = H)
I.62 (R = TCA)

Reagents and conditions: Synthesis of intermediate I.61 a) TiCl₄, CH₂Cl₂, 0° C., 45 minutes. 75%. b) NaH, (28), DMF, 0° C. to rt, overnight.68%; c) TBSOTf, Ac₂O, 0° C., 20 minutes, 78%. d) DMAPA, THF, rt, 3 hours. 78%, e) K₂CO₃, Trichloracetonitrile, CH₂Cl₂, rt.

1,6-anhydro-2-azido-3-O-benzyl-2-deoxy-β-D-glucopyranose, Intermediate I.57

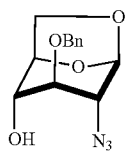

Intermediate I.17 (1.22 g, 3.32 mmol, 1 eq) was dissolved in 45 mL dry CH₂Cl₂ and placed on ice. TiCl₄ (360 µL, 3.32 mmol, 1 eq) was then added slowly. The reaction stirred for 45 minutes on ice when TLC (cyclohexane/EtOAc 2:1 v/v) showed the disappearance of the starting material. The reaction was quenched by pouring it onto a mixture of ice water and stirring it for 15 minutes. The layers were separated and the aqueous layer was extracted with CH₂Cl₂. The combined organic layers were dried on MgSO₄, filtered and concentrated and the resulting syrup was purified using (cyclohexane/EtOAc 8-66%) to give intermediate I.57 as a slightly yellow syrup 720 mg (2.6 mmol, 78%) (¹H NMR (500 MHz, CDCl₃) δ 7.39-7.29 (m, 5H, Ar), 5.45 (bs, J=1.7 Hz, 1H, H1), 4.66-4.59 (m, 2H, CH₂Bn), 4.56-4.51 (m, 1H, H5), 4.23 (dd, J=7.3, 1.1 Hz, 1H, H6a), 3.78 (dd, J=7.3, 5.9 Hz, 1H, H6b), 3.71-3.66 (m, 1H, H4), 3.60 (p, J=1.6 Hz, 1H, H3), 3.52 (bs, J=1.7 Hz, 1H, H2), 2.72 (d, J=10.5 Hz, 1H, 4-OH). In agreement with literature, *J. Org. Chem.* 1989, 54 (6), 1346-1353).

N-benzyl-N-benzyloxycarbonyl-5-bromo-aminopentane, Intermediate I.58

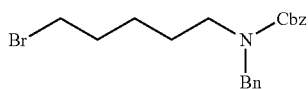 [SMILES: O=C(OCc1ccccc1)N(CCCCCBr)Cc1ccccc1]

Intermediate I.42 (580 mg, 1.77 mmol, 1 eq) was dissolved in 18 mL dry CH₂Cl₂ and the reaction flask was covered in aluminium foil to exclude light before cooling on ice. NBS (470 mg, 2.66 mmol, 1.5 eq) and PPh₃ (700 mg, 8.07 mmol, 1.5 eq) were then added in a single portion and the reaction stirred for one hour when TLC (9:1 v/v cyclohexane/EtOAc) showed the complete conversion of the starting material. The mixture was concentrated while protected from light aid the crude material was then purified by column chromatography using 9:1→7:3 cyclohexane/EtOAc to give intermediate I.43 as a slightly yellow syrup, 600 mg (1.54 mmol, 87%) (¹H NMR (500 MHz, CDCl₃) δ 7.41-7.23 (m, 9H), 7.20-7.14 (m, 1H), 5.18 (d, J=12.0 Hz, 2H), 4.50 (d, J=8.8 Hz, 2H), 3.44-3.09 (m, 4H), 1.80 (dt, J=38.8, 7.3 Hz, 2H), 1.57-1.47 (m, 2H), 1.43-1.30 (m, 2H). In agreement with literature *J. ACS Cent. Sci.* 2017, 3 (3), 224-231.

1,6-anhydro-4-O-(5'-N-benzyl-W-carboxybenzylpentanyl)-2-azido-3-O-benzyl-2-deoxy-β-D-glucopyranose, Intermediate I.59

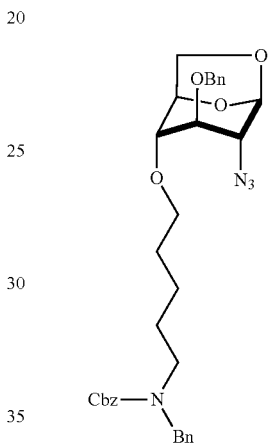

Intermediate I.57 (147 mg, 0.53 mmol, 1 eq) was dissolved in 2 mL dry DMF and cooled on ice before NaH (60% in mineral oil, 53 mg, 1.33 mmol, 2.5 eq) was added. After stirring for 45 minutes the flask was covered in aluminium foil to exclude light and a solution containing the bromide linker I.58 (320 mg, 0.82 mmol, 1.5 eq) dissolved in 2 mL dry DMF was added dropwise to the mixture. The reaction was warmed to room temperature, stirring overnight. The following day the reaction was cooled on ice and quenched with H₂O. The mixture was extracted twice with CH₂Cl₂ and the combined organic phases were dried on MgSO₄, filtered and concentrated. The resulting crude was purified using flash chromatography (cyclohexane cyclohexane/EtOAc 8-50%) to yield intermediate I.59 as a clear oil (210 mg, 0.36 mmol, 68%) (R$_f$=0.2 (cyclohexane/EtOAc, 4/1 v/v) HRMS: calc for: C₃₃H₃₈N₄O₆Na: 609.2689 [M+Na]⁺; Found: 609.2678 ¹H NMR (500 MHz, CDCl₃) δ 7.39-7.14 (m, 15H, Ar), 5.48 (s, 1H, H1), 5.18 (d, J=15.2 Hz, 2H, NCH₂Bn), 4.67 (d, J=11.9 Hz, 1H, CH₂Bn), 4.63-4.54 (m, 2H, H5, CH₂Bn), 4.50 (d, J=9.1 Hz, 2H, OCH₂Bn), 4.06 (d, J=7.2 Hz, 1H, H6a), 3.78-3.72 (m, 1H, H6b), 3.60 (s, 1H, H3), 3.52-3.31 (m, 2H, CH₂ Linker), 3.30-3.13 (m, 4H, H2, H4, CH₂ Linker), 1.61-1.48 (m, 4H, CH₂ Linker×2), 1.36-1.25 (m, 2H. CH₂ Linker) ¹³C NMR (126 MHz, CDCl₃) δ 137.92 (Ar), 137.33 (Ar), 128.55 (Ar), 128.53 (Ar), 128.44 (Ar), 128.05 (Ar), 127.90 (Ar), 127.81 (Ar), 127.76 (Ar), 127.25 (Ar), 100.62 (C1), 77.33 (C4), 76.26 (C3), 74.27 (C5), 72.41 (CH₂Bn), 69.44 (CH₂ Linker), 67.15 (NCH₂Bn), 65.34 (C6), 59.74 (C2), 50.53/50.24 (CH₂ Linker rotamer), 47.08/46.16 (CH₂ Linker rotamer), 29.33 (CH₂=Linker), 27.91/27.45 (CH₂ Linker rotamer), 23.31 (CH₂ Linker)).

1,6-di-O-acetyl-4-O-(5'-N-benzyl-N'-carboxybenzyl-pentanyl)-2-azido-3-O-benzyl-2-deoxy-α/β-D-glucopyranose, Intermediate I.60

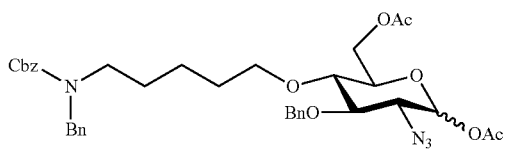

Intermediate I.59 (180 mg, 0.31 mmol, 1 eq) was dissolved in Ac₂O (3 mL) and placed on ice. TBSOTf (7.1 µL, 0.03 mmol, 0.1 eq) was then added and the reaction stirred for 15 minutes before quenching with 0.1 mL NEt₃ followed by the slow addition of MeOH (4 mL). The mixture stirred for 15 minutes on ice before being diluted with toluene and the solvents evaporated. The crude was coevaporated a further three times with toluene before the crude was loaded onto a column and purified with 5:1→2:1 cyclohexane/EtOAc to give intermediate I.60 as a clear oil (177 mg, 0.26 mmol, 83%, inseparable mixture of anomers, ~α/β 2:1 ($R_f$=0.4 (cyclohexane/EtOAc, 3/1 v/v) HRMS: calc for $C_{37}H_{44}N_4O_9Na$: 711.3006 [M+Na]⁺, Found: 711.3023 Selected peaks for the α anomer: ¹H NMR (400 MHz, CDCl₃) δ 7.42-7.13 (m, 20H, Ar), 6.20 (d, J=3.6 Hz, 1H, H1a), 5.17 (d, J=10.1 Hz, 2H, NCH₂Bn), 4.94-4.81 (m, 2H, CH₂Bn), 4.48 (bs, J=5.5 Hz, 2H, OCH₂Bn), 4.23 (bs, J=4.9 Hz, 2H, H6a, H6b), 3.89-3.74 (m, 3H, H3, H5, CH₂ Linker), 3.58-3.35 (m, 3H, H2, H4, CH₂ Linker), 3.21 (d, J=24.1 Hz, 2H, CH₂ Linker), 2.16 (s, 3H, COOMe), 2.07 (s, 3H, COOMe), 1.51 (bs, 4H, CH₂ Linker×2), 1.31-1.20 (m, 2H, CH₂ Linker) ¹³C NMR (101 MHz, CDCl₃) δ 170.86 (Carbonyl), 169.06 (Carbonyl), 138.00 (Ar), 137.65 (Ar), 128.67 (Ar), 128.58 (Ar), 128.20 (Ar), 128.11 (Ar), 128.06 (Ar), 127.94 (Ar), 127.43 (Ar), 127.31 (Ar), 90.66 (C1 alpha), 80.58 (C3), 78.19 (C4), 75.85 (CH₂Bn), 73.68 (CH₂ Linker), 71.72 (C5), 67.46 (NCH₂Bn), 62.87 (C2), 62.68 (C6), 50.77 (OCH₂Bn), 47.31/46.38 (CH₂ Linker rotamer), 30.36 (CH₂ Linker), 27.72 (CH₂ Linker), 23.66 (CH₂ Linker), 21.25 (COCH₃), 21.09 (COCH₃)).

6-O-acetyl-4-O-(5'-N-benzyl-N'-carboxybenzyl-pentanyl)-2-azido-3-O-benzyl-2-deoxy-α/β-D-glucopyranose, Intermediate I.61

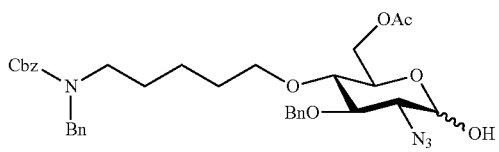

Intermediate I.60 (750 mg, 1.09 mmol, 1 eq) was dissolved in 11 mL dry THF and DMAPA (0.7 mL, 5.45 mmol, 5 eq) was added at room temperature. The reaction stirred until TLC analysis showed that no remaining SM was visible. The reaction was diluted with CH₂Cl₂ and was washed with 1 M HCl. The aqueous layer was reextracted with CH₂Cl₂ and the combined organic layers were dried on MgSO₄, filtered and concentrated. The crude was purified using 3:1→2:1 cyclohexane/EtOAc to give intermediate I.61 as a clear oil (568 mg, 0.88 mmol, 81%, inseparable mixture of anomers) ($R_f$=0.19 (cyclohexane/EtOAc 2/1 v/v) HRMS: calc for $C_{35}H_{42}N_4O_8Na$: 669.2900 [M+Na]⁺, Found: 669.2911 ¹H NMR (500 MHz, CDCl₃, selected peaks) 7.37-7.14 (m, 20H, Ar), 5.30-5.27 (m, 1H, H1a), 5.17 (d, J=13.8 Hz, 2H, NCH₂Bn), 4.91-4.73 (m, 2H, CH₂Bn), 4.48 (d, J=10.1 Hz, 2H, OCH₂Bn), 4.33 (d, J=12.0 Hz, 1H, H6aα), 4.22-4.10 (m, 1H, H6bα), 4.10-4.01 (m, 1H, H5a), 3.92 (t, J=9.8 Hz, 1H, H3a), 3.83-3.68 (m, 2H, CH₂ Linker), 3.56-3.00 (m, 7H, H2a6, H4a6, CH₂ Linker), 2.07 (s, 3H, COCH₃), 1.55-1.41 (m, 4H, CH₂ Linker×2), 1.29-1.14 (m, 2H, CH₂ Linker) ¹³C NMR (126 MHz, CDCl₃, selected peaks) δ 170.87 (Carbonyl), 137.84 (Ar), 128.66 (Ar), 128.63 (Ar), 128.62 (Ar), 128.10 (Ar), 128.06 (Ar), 127.94 (Ar), 127.46 (Ar), 127.39 (Ar), 127.29 (Ar), 92.17 (C1α), 79.98 (C3α), 78.70 (C4α), 75.61 (CH₂Bn), 73.36 (CH₂ Linker), 69.55 (C5α), 67.31 (NCH₂Bn), 64.01 (C2α), 62.97 (C6α), 50.33 (OCH₂Bn), 47.19/46.25 (CH₂ Linker rotamer), 30.19 (CH₂ Linker rotamer), 28.18/27.72 (CH₂ Linker rotamer), 23.51/23.48 (CH₂ Linker rotamer), 21.00 (COCH₃)).

6-O-acetyl-4-O-(5'-N-benzyl-N'-carboxybenzyl-pentanyl)-2-azido-3-O-benzyl-2-deoxy-α/β-D-glucopyranose, Intermediate I.62

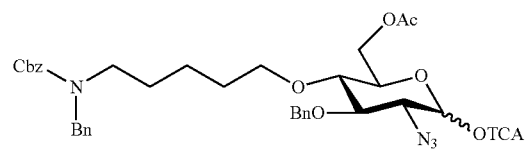

Intermediate I.61 (135 mg, 0.21 mmol, 1 eq) was dried in the presence of K₂CO₃ (160 mg, 1.16 mmol, 5.5 eq) under vacuum for two hours before the addition of 2 mL dry CH₂Cl₂. Trichloroacetonitrile (0.2 mL, 1.99 mmol, 10 eq) was added at room temperature and the reaction continued stirring under N₂ overnight. The following day the mixture was passed through a pad of celite and the filtrate was concentrated (rotovap waterbath temperature <25° C.) and the crude Intermediate I.62 was used immediately with no further analysis (ii) Synthesis of Trisaccharide Intermediate with Linker at Non-Reducing End Scheme 13

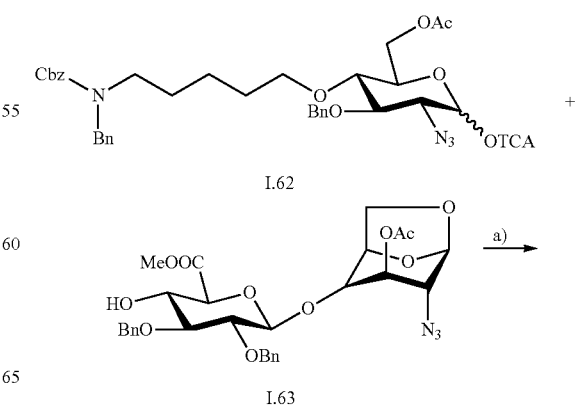

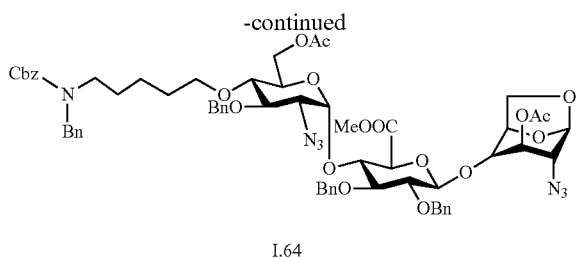

I.64

Reagents and Conditions: Syntesis of intermediate I.64 b) TBSOTf, toluene, -25° C., 1.5 h 6-O-acetyl-4-O-(5'N-benzyl-5'N-carboxybenzyl-pentanyl)-2-azido-3-O-benzyl-2-deoxy-α-D-glucopyranosyl-(1→4)-methyl-2,3-di-O-benzyl-β-D-glucopyranosyluronate-(1→4)-1,6-anhydro-2-azido-3-O-acetyl-2-deoxy-β-D-glucopyranose, Intermediate I.64

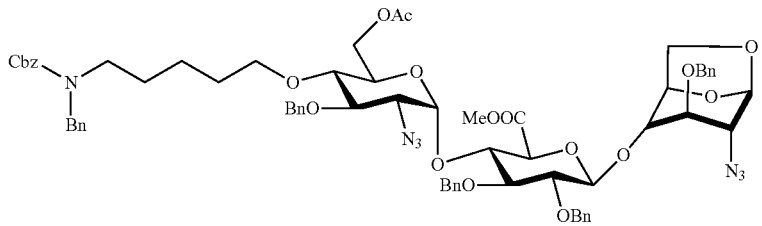

Crude TCA intermediate (1.62, 1.5 eq) and commercially available disaccharide 1.63 (100 mg, 0.14 mmol, 1 eq) were dried together in the presence of 340 mg 4 Å MS under vacuum for 6 hours before addition of 5 mL dry toluene. The mixture stirred for 45 minutes at room temperature before cooling to −25° C. TBSOTf (18.4 μL, 0.07 mmol, 0.5 eq) was then added and the reaction stirred slowly warming until no more donor was visible on TLC. The reaction was quenched with the addition of NEt$_3$ and the mixture was passed through a pad of celite. The pad was washed with CH$_2$Cl$_2$ until the filtrate ran clear which was then concentrated. The crude residue was purified using 7/36/4 cyclohexane/EtOAc to give intermediate I.64 as a yellow foam.

Product co-elutes as a trisaccharide with contaminants likely being residual glycosylation impurities (R$_f$=0.29 (3/2 v/v cyclohexane/EtOAc) HRMS calc for: C$_{64}$H$_{73}$N$_7$O$_{18}$Na: 1250.4910. Found: 1250.4895. Selected peaks for major product: $^1$H NMR (400 MHz, CDCl$_3$) δ 7.41-7.11 (m, 25H, Ar), 5.50 (d, J=3.7 Hz, 1H, H"1), 5.47 (bs, J=1.7 Hz, 1H, H1), 5.24-5.21 (m, 1H, H2), 5.19-5.12 (m, 2H, NCH$_2$Bn), 5.02 (d, J=10.9 Hz, 2H, CH$_2$Bn), 4.85-4.78 (m, 3H, CH$_2$Bn), 4.73 (d, J=11.0 Hz, 1H, CH$_2$Bn), 4.67 (d, J=7.6 Hz, 1H, H'1), 4.57-4.53 (m, 1H, H5), 4.47 (bs, J=6.6 Hz, 2H, OCH$_2$Bn), 4.21 (bs, J=3.7 Hz, 2H, H6"a, H6"b), 4.16-4.06 (m, 1H, H'4), 4.03-3.99 (m, 1H, H6a), 3.97 (d, J=9.6 Hz, 1H, H'5), 3.84-3.72 (m, 7H, COOMe, CH$_2$ Linker, H6b, H'3, H"3), 3.71 (bs, 1H, CH$_2$ Linker), 3.68-3.61 (m, 2H, H4, H'2), 3.53-3.49 (m, 1H, H"5), 3.42-3.32 (m, 1H, CH$_2$ Linker), 3.27-3.15 (m, 4H, CH$_2$ Linker, H3, H"2, H"4), 2.10 (s, 3H, COCH$_3$), 2.07 (s, 3H, COCH$_3$), 1.54-1.42 (m, 4H, CH$_2$ Linker×2), 1.25 (m, 2H, CH$_2$ Linker) $^{13}$C NMR (101 MHz, CDCl$_3$) δ 170.78 (Carbonyl), 169.24 (Carbonyl), 168.31 (Carbonyl), 138.25 (Ar), 138.19 (Ar), 137.98 (Ar), 137.81 (Ar), 129.13 (Ar), 128.63 (Ar), 128.57 (Ar), 128.54 (Ar), 128.46 (Ar), 128.39 (Ar), 128.32 (Ar), 128.24 (Ar), 128.03 (Ar), 127.90 (Ar), 127.88 (Ar), 127.74 (Ar), 127.66 (Ar), 127.51 (Ar), 127.39 (Ar), 125.39 (Ar), 103.24 (C'1), 100.32 (01), 97.77 (C"1), 83.87 (C'3), 81.53 (C'2), 79.77 (O"3), 78.23 (O"2), 75.88 (C4), 75.30 (CH$_2$Bn), 75.09 (CH$_2$Bn), 74.99 (C'4), 74.88 (CH$_2$Bn), 74.51 (C'S), 73.72 (C5), 73.07 (CH$_2$ Linker), 70.51 (C2), 69.72 (C"5), 67.13 (NCH$_2$Bn), 64.91 (C6), 62.25 (C"6), 58.91 (C3), 50.61 (OCH$_2$Bn), 47.16/46.21 (CH$_2$ Linker rotamer), 30.15 (CH$_2$ Linker), 28.18/27.69 (CH$_2$ Linker rotamer), 23.43 (CH$_2$ Linker), 21.10 (COCH$_3$), 20.96 (COCH$_3$)).

Scheme 14

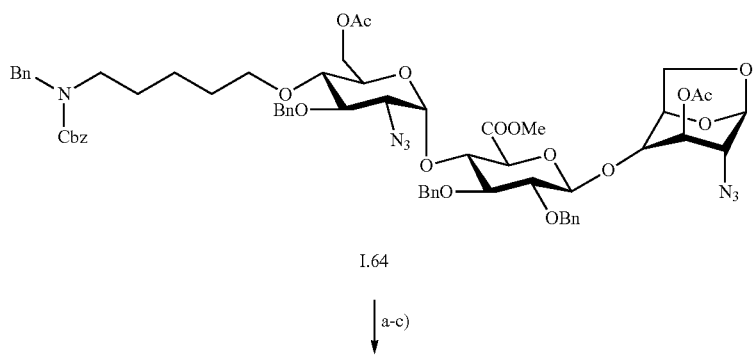

I.64

↓ a-c)

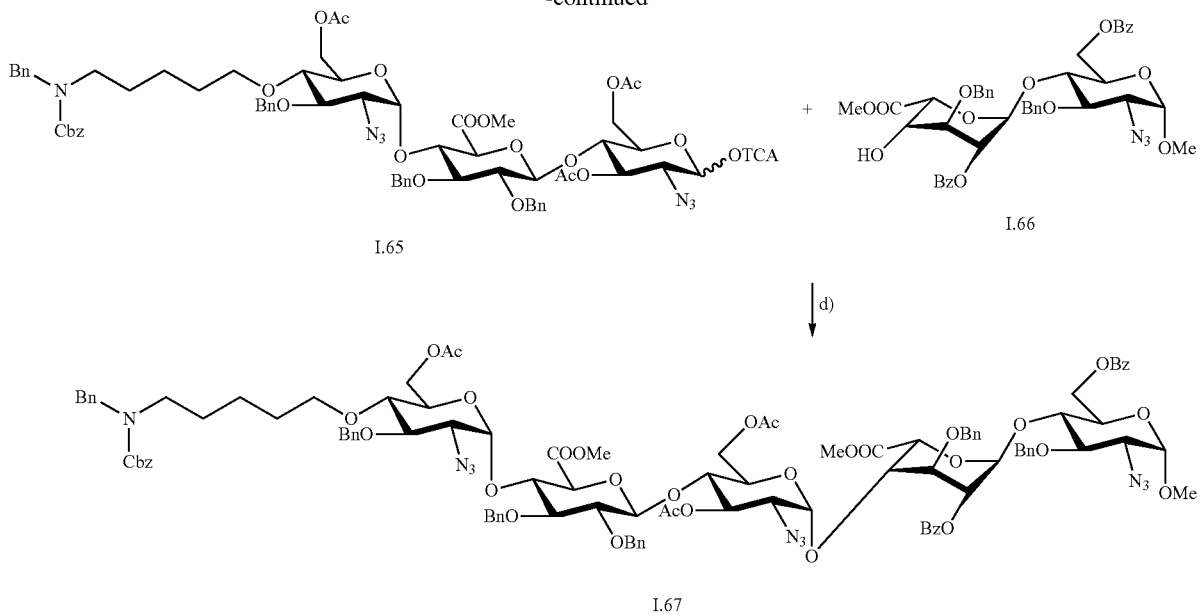

Reagents and Conditions: Synthesis of intermediate I.67 a) TBSOTf, Ac₂O, 0° C., 30 minutes, 76%. b) DMAPA, THF, rt. 71%, c) K₂CO₃, Trichloracetonitrile, CH₂Cl₂, rt. over night, d) TfOH 0.1M in dry toluene molecular sieves, 4 Å, dry toluene, -40° C. slowly warming to room temp.

6-O-acetyl-2-azido-3-O-benzyl-4-O-(5'-benzyl-5'-benzyloxycarbonyl-aminopentanyl)-2-deoxy-α-D-glucopyranosyl-(1→4)-O-(methyl 2,3-di-O-benzyl-β-D-glucopyranosyluronate)-(1→4)-3,6-di-O-acetyl-2-azido-2-deoxy-α/β-D-glucopyranolactol
Intermediate I.65

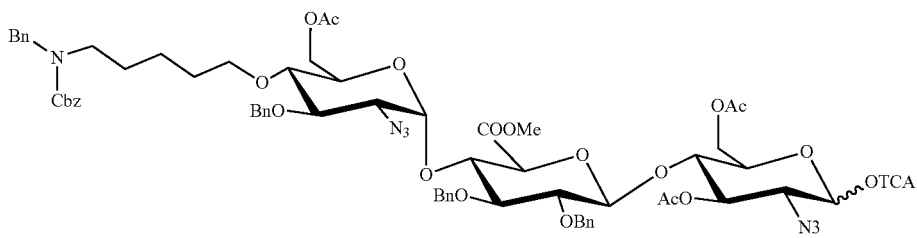

Intermediate I.64 (175 mg, 0.14 mmol, 1 eqv.) was dissolved in Ac₂O (1.5 mL) and placed on ice. TBSOTf (4.6 µL, 0.01 mmol, 0.1 eqv.) was then added. The reaction stirred for 30 minutes when TLC (cHex/EtOAc 3/2 v/v) showed no remaining starting material. 0.2 mL NEt₃ was then added followed by MeOH. The mixture was diluted with toluene and the solvents were removed in vacuo. The crude was coevaporated twice with additional toluene. The resulting crude syrup was purified with column chromatography (cHex/EtOAc 7:33:2 v/v) to give 6-O-acetyl-2-azido-3-O-benzyl-4-O-(5'-benzyl-5'-benzyloxycarbonyl-aminopentanyl)-2-deoxy-α-D-glucopyranosyl-(1→4)-O-(methyl 2,3-di-O-benzyl-β-D-glucopyranosyluronate)-(1→4)-1,3,6-tri-O-acetyl-2-azido-2-deoxy-α/β-D-glucopyranose as a white foam (143 mg, 0.11 mmol, 76%, mixture of anomers). $R_f$=0.64 (3/2 cHex/EtOAc v/v)

HRMS calc. For $C_{68}H_{79}N_7NaO_{21}$: 1352.5227 [M+Na]⁺. Found: 1352.5277.

¹H NMR (500 MHz, CDCl₃, selected peaks) b 7.43-7.12 (m, 25H, Ar), 6.23 (d, J=3.8 Hz, 1H, H1), 5.48 (d, J=3.6 Hz, 1H, H1''), 5.42 (dd, J=10.6, 8.6 Hz, 1H, H3), 5.18-5.14 (m, 2H, NCH₂), 4.94 (d, J=11.0 Hz, 1H, BnCH₂), 4.84-4.78 (m, 3H, BnCH₂), 4.74-4.70 (m, 2H, BnCH₂), 4.51-4.45 (m, 2H, OCH₂), 4.36-4.30 (m, 2H, H6a, H1'), 4.27-4.23 (m, 1H, H6a''), 4.20-4.14 (m, 2H, H6b, H6b''), 4.08-4.00 (m, 1H, H5'), 3.88-3.83 (m, 1H, H3'), 3.79-3.73 (m, 5H, COOMe, H5, H3''), 3.75-3.67 (m, 3H, CH₂ Linker×1, H4, H4'), 3.55 (dd, J=10.7, 3.7 Hz, 1H, H2), 3.47-3.43 (m, 1H, H2'), 3.43-3.37 (m, 2H, CH₂ Linker×1, H5''), 3.26-3.08 (m, 4H, CH₂ Linker, H2'', H4''), 2.20 (s, 3H, OAc), 2.11 (s, 3H, OAc), 2.07 (s, 3H, OAc), 2.07 (s, 3H, OAc).

¹³C NMR (126 MHz, CHCl₃, selected peaks) δ 170.62 (Carbonyl), 170.12 (Carbonyl), 170.09 (Carbonyl), 168.60 (Carbonyl), 168.31 (Carbonyl), 137.93 (Ar), 137.64 (Ar), 137.59 (Ar), 137.48 (Ar), 128.52 (Ar), 128.48 (Ar), 128.44 (Ar), 128.40 (Ar), 128.33 (Ar), 127.91 (Ar), 127.78 (Ar), 127.72 (Ar), 127.68 (Ar), 127.56 (Ar), 127.29 (Ar), 127.27 (Ar), 103.09 (C1'), 97.46 (C1''), 89.92 (C1), 83.87 (C4'), 82.07 (C2'), 79.78 (C4), 78.04 (C4''), 75.34 (C3'', BnCH2× 3), 74.79 (C5'), 74.40 (C3'), 73.11 (CH2 Linker), 70.99 (C5), 69.81 (C3, C5''), 67.14 (NCH2), 63.06 (C2''), 62.19 (C6''), 61.28 (C6), 60.31 (C2), 52.69 (COOMe), 30.04 (CH2 Linker), 23.30 (CH$_2$ Linker), 21.01 (OAc), 20.83 (OAc×2), 20.67 (OAc).

The isolated intermediate (121 mg, 0.10 mmol, 1 eqv.) was dissolved in 1 mL dry THF. DMAPA (38 µL, 0.3 mmol, 3 eqv.) was then added at room temperature. The reaction stirred until TLC showed no remaining starting material (cHex/EtOAc 3/2 v/v). The reaction was diluted with CH$_2$Cl$_2$ and was washed with 1M HCl. The aqueous layer was extracted again with CH$_2$Cl$_2$. The combined organic layers were dried on MgSO$_4$, filtered and the filtrate was concentrated. The crude syrup was then purified with column chromatography (cHex/EtOAc, 7:3→3:2 v/v) to give 6-O-acetyl-2-azido-3-O-benzyl-4-O-(5'-benzyl-5'-benzyloxycarbonyl-aminopentanyl)-2-deoxy-α-D-glucopyranosyl-(1→4)-O-(methyl 2,3-di-O-benzyl-β-D-glucopyranosyluronate)-(1→4)-3,6-di-O-acetyl-2-azido-2-deoxy-α/β-D-glucopyranolactol as a white foam. (91 mg, 0.07 mmol, 71%)

Rf=0.29 (2/1 cHex/EtOAc v/v)

HRMS calc. for C$_{66}$H$_{77}$N$_7$NaO$_{20}$: 1310.5121 [M+Na+]. Found: 1310.5137.

(Ar), 127.13 (Ar), 103.05 (O1'), 97.46 (C1''), 94.09 (C1), 83.81 (C4'), 81.80 (C2'), 79.78 (C4), 78.05 (C4''), 75.35 (BnCH$_2$), 75.22 (BnCH$_2$, C3'), 74.79 (C5'), 74.44 (O3''), 73.10 (CH$_2$ Linker), 71.32 (C5), 69.81 (O5''), 69.71 (C3), 67.14 (NCH$_2$), 63.06 (C2''), 62.18 (C6''), 61.22 (C6), 60.60 (C6), 52.61 (COOMe), 30.03 (CH$_2$ Linker), 23.30 (CH$_2$ Linker), 20.83 (OAc), 20.80 (OAc), 20.67 (OAc).

Methyl 6-O-acetyl-2-azido-3-O-benzyl-4-O-(5'-benzyl-5'-benzyloxycarbonyl-aminopentanyl)-2-deoxy-α-D-glucopyranosyl-(1→4)-O-(methyl 2,3-di-O-benzyl-β-D-glucopyranosyluronate)-(1→4)-3,6-di-O-acetyl-2-azido-2-deoxy-α-glucopyranosyl-(1→4)-(methyl 2-O-benzoyl-3-O-benzyl-α-L-idopyranosyluronate)-(1→4)-2-azido-6-O-benzoyl-3-O-benzyl-2-deoxy-α-D-glucopyranoside, Intermediate I.67

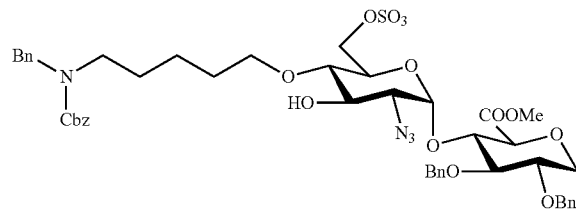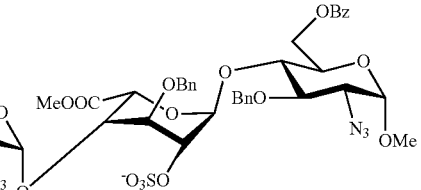

The crude (110 mg, 0.085 mmol, 1 eqv.) was dried with K$_2$CO$_3$ (118 mg, 0.85 mmol, 10 eqv.) for 3 hours before the addition of 1 mL dry CH$_2$Cl$_2$. Trichloroacetonitrile (90 µL, 0.85 mmol, 10 eqv.) was then added, and the reaction stirred overnight at room temperature. The following day the mixture was filtered through a pad of celite. The filtrate was concentrated on a rotary evaporator (water bath temperature <25° C.) and the crude material of intermediate I.65 was isolated.

R$_f$=0.68 (3/2 cHex/EtOAc+1% NEt$_3$ v/v/v)

HRMS calc. for C68H77Cl3N8Na20: 1453.4217 [M+Na+] Found: 1453.4269.

$^1$H NMR (400 MHz, CDCl$_3$, selected peaks) δ 8.80 (d, J=1.8 Hz, 1H, NH), 8.77 (s, 1H, NH), 7.41-7.11 (m, 25H, Ar), 6.41 (d, J=3.6 Hz, 1H, H1a), 5.67 (d, J=8.4 Hz, 1H, H1l3), 5.59-5.48 (m, 1H, H3), 5.49 (d, J=3.8 Hz, 1H, H1''), 5.16 (d, J=10.1 Hz, 2H, NCH$_2$), 4.98 (d, J=10.9 Hz, 1H, BnCH$_2$), 4.86-4.66 (m, 5H, BnCH$_2$), 4.51-4.44 (m, 2H, OCH$_2$), 4.36 (d, J=8.1 Hz, 1H, H1'), 4.33-4.30 (m, 1H, H6a), 4.28-4.23 (m, 1H, H6a''), 4.18-4.12 (m, 2H, H6b, H6b''), 4.08-4.02 (m, 2H), 3.89-3.82 (m, 2HH5', H3''), 3.76 (bs, 3H, COOMe), 3.74-3.68 (m, 3H, CH$_2$ Linker×1H, H4', H4), 3.65 (dd, J=10.7, 3.7 Hz, 1H, H2), 3.48-3.30 (m, 3H, CH$_2$ Linker×1H, H5'', H2'), 3.26-3.11 (m, 4H, CH$_2$ Linker, H2'', H4''), 2.10 (d, J=1.1 Hz, 3H, OAc), 2.07 (s, 3H, OAc), 2.03 (s, 3H, OAc), 1.56-1.40 (m, 4H, CH$_2$ Linker×2), 1.29-1.16 (m, 2H, CH$_2$ Linker).

$^{13}$C NMR (101 MHz, CDCl$_3$, selected peaks) δ 170.62 (Carbonyl), 170.02 (Carbonyl), 169.86 (Carbonyl), 168.30 (Carbonyl), 160.52 (C=NH), 137.94 (Ar), 137.61 (Ar), 137.51 (Ar), 128.52 (Ar), 128.47 (Ar), 128.43 (Ar), 128.39 (Ar), 128.36 (Ar), 128.33 (Ar), 127.91 (Ar), 127.77 (Ar), 127.66 (Ar), 127.58 (Ar), 127.47 (Ar), 127.28 (Ar), 127.27

Intermediate I.65 (100 mg, 0.075 mmol, 1.5 eqv.) was dried in the presence of commercially available I.66 (40 mg, 0.05 mmol, 1 eqv.) and 90 mg 4 Å MS. Dry toluene was then added and the mixture stirred at room temperature for 1 hour. The mixture was then cooled to −40° C. TBSOTf (0.1 M solution in dry toluene) was then added slowly. The reaction stirred slowly, warming to room temperature. TLC showed no remaining donor and the reaction was quenched by the addition of NEt$_3$. The mixture was passed through a pad of celite and washed with CH$_2$Cl$_2$. The solvents were removed, and the crude was taken up in CH$_2$Cl$_2$ and washed with 1 M HCl, sat. aq. NaHCO$_3$ and brine. The organic layer was dried on MgSO$_4$, filtered and the filtrate was concentrated. The crude syrup was purified using column chromatography (Tol/Ace 100/0→85/15 v/v) to give intermediate I.67 (11 mg, 0.005 mmol, 10%).

Rf 0.35 (9/1 Tol/Ace v/v)

[α]$_D$+47.5 (c=1, CHCl$_3$)

$^1$H NMR (600 MHz, CDCl$_3$) δ 8.09 (d, J=7.6 Hz, 2H, Ar), 8.01 (d, J=7.6 Hz, 2H, Ar), 7.51 (s, 2H, Ar), 7.44-7.13 (m, 39H, Ar), 5.73 (d, J=5.9 Hz, 1H, H1'), 5.47 (d, J=3.7 Hz, 1H, H1''''), 5.32 (s, 1H, H3''), 5.27 (t, J=6.3 Hz, 1H, H2'), 5.16 (d, J=18.8 Hz, 1H, NCH$_2$), 5.11 (d, J=3.4 Hz, 1H, H1''), 4.99-4.94 (m, 2H, BnCH$_2$), 4.83-4.70 (m, 8H, H1, BnCH$_2$×7), 4.64 (d, J=11.2 Hz, 1H, BnCH$_2$), 4.60 (s, 1H, H4'), 4.58 (d, J=12.6 Hz, 1H, H6a), 4.49-4.41 (m, 4H, OCH$_2$, H6b, H6a''), 4.34 (d, J=7.8 Hz, 1H, H1'''), 4.24 (d, J=11.6 Hz, 1H, H6a''''), 4.19 (dd, J=12.4, 3.7 Hz, 1H, H6b''), 4.18-4.09 (m, 4H, H6b'''', H3, H3', H4''), 4.05-4.00 (m, 2H, H5, H5'''), 4.01-3.96 (m, 1H, H4), 3.92-3.87 (m, 1H, H3), 3.85 (d, J=9.7 Hz, 1H, H3'''), 3.81 (d, J=10.8 Hz, 1H, H5''), 3.76-3.65 (m, 7H, COOMe, CH$_2$ Linker, H4'', H4''', H3''''), 3.53 (s, 3H, COOMe), 3.43-3.38 (m, 4H, H2'', H5'''', CH$_2$ Linker), 3.36

(s, 3H, COOMe), 3.26-3.11 (m, 5H, CH$_2$ Linker, H2, H2"", H4""), 2.07 (s, 3H, OAc), 2.04 (s, 3H, OAc), 2.02 (s, 3H, OAc), 1.50 (s, 4H, CH$_2$ Linker×2), 1.26 (s, 2H, CH$_2$ Linker).

$^{13}$C NMR (151 MHz, CDCl$_3$) δ 170.64 (Carbonyl), 170.08 (Carbonyl), 169.98 (Carbonyl), 169.70 (Carbonyl), 168.34 (Carbonyl), 166.04 (Carbonyl), 165.31 (Carbonyl), 129.89 (Ar), 129.84 (Ar), 129.81 (Ar), 129.02 (Ar), 128.64 (Ar), 128.53 (Ar), 128.49 (Ar), 128.32 (Ar), 128.24 (Ar), 128.06 (Ar), 127.93 (Ar), 127.83 (Ar), 127.69 (Ar), 127.52 (Ar), 127.21 (Ar), 103.21 (C1+"), 98.38 (C1), 98.23 (C1'), 97.61 (C2"), 97.45 (C1""), 83.71 (C4"), 81.68 (C2"), 79.78 (C4"), 78.46 (C3), 78.03 (C4'''), 76.55 (C4), 75.70 (C3""), 75.42 (BnCH$_2$), 75.36 (BnCH$_2$), 75.18 (BnCH$_2$), 75.05 (BnCH$_2$), 74.83 (C5"), 74.46 (BnCH$_2$), 74.38 (C3"), 73.11 (CH$_2$ Linker), 73.03 (C3'), 72.14 (C2'), 71.50 (C4'), 69.78 (C5""), 69.65 (C5), 69.26 (C3"), 69.09 (C5'), 67.15 (NCH$_2$), 63.32 (C2), 63.05 (C2""), 62.31 (C6), 62.18 (C6""), 61.28 (C6"), 60.66 (C2"), 55.38 (COOMe), 52.57 (OMe), 52.22 (COOMe), 30.04 (CH$_2$ Linker), 23.29 (CH$_2$ Linker), 20.82 (OAc×2), 20.63 (OAc).

MALDI TOF calc. for: C$_{108}$H$_{118}$N$_{10}$NaO$_{32}$: 2089.7806. [M+Na]$_+$ Found: 2089.7584.

Utilising the deprotection, reduction and sulfatation steps depicted in Scheme 11, would then transform Intermediate I.67 to Example 1.3

Example 2: Preparation of Heparin Fragment Fractions by Depolymerization of Heparin

Example 2.1-2.3: Heparin Fragment Fractions Prepared by Depolymerization of Heparin Followed by Fractionation Oligosaccharides, predominantly of the size of eight sugar units (octa), were prepared by partial nitrous acid cleavage of native heparin followed by fractionation by gel chromatography. An octasaccharide produced by nitrous cleavage is the shortest fragment that can contain a functional active sequence (Thunberg L. et al, FEBS Letters 117 (1980), 203-206).

Depolymerization of heparin: 10 g of heparin sodium was dissolved in 36 ml of water by stirring overnight. 0.30 g NaNO$_2$ was added to the heparin solution and allowed to dissolve. The solution was acidified to pH 2.5 by addition of 4M HCl. After a total reaction time of 2 h at room temperature, the solution was neutralized by addition of 4M NaOH.

The degradation mixture was separated based on molecular size by gel permeation chromatography (GPC), where portions of 3 ml was applied to the column (HiLoad 26/600 Superdex 30 µg, mobile phase 0.15 M NaCl) at a flow rate of 2.5 ml/min. The collected fractions (3 ml) were analyzed for aldehyde by the MBTH reaction, essentially as described in Smith R. L. and Gilkerson E (1979), Anal Biochem 98, 478-480. Abroad peak centred on the elution position of the octasaccharide was collected. The combined oligosaccharide elution fractions from several preparative runs were concentrated by evaporation to a volume of 18 ml and re-chromatographed on the same column. For all re-chromatographic runs three fractions, representing deca- (2.3), octa- (2.2) and hexasaccharide fragments (2.1), were collected and pooled.

Figure 7:
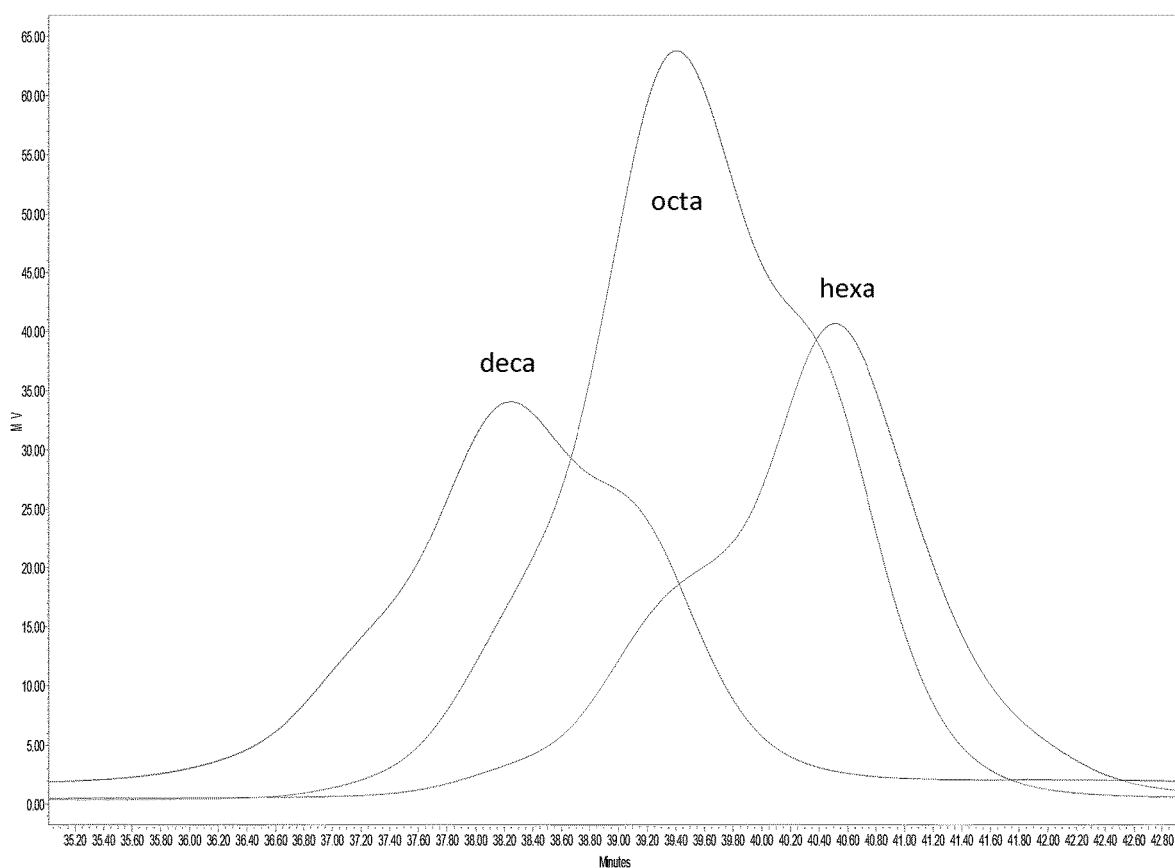
FIG. 7: Analytical chromatography of isolated oligosaccharide fractions

The collected fractions 2.1-2.3 were analysed by Evaluation Method A (see FIG. 7). The "hexa" fraction consists of a major peak representing hexasaccharide and a shoulder representing octasaccharide. The "octa" fraction consists of a major peak representing octasaccharide with a shoulder representing hexasaccharide and a minor shoulder representing decasaccharide. The "deca" fraction consists of a major peak representing decasaccharide with a shoulder representing octasaccharide and a minor shoulder representing dodecasaccharide.

The concentration of the heparin fragment fractions (see Table 2) was determined by Evaluation Method B.

TABLE 2

Analysis of the concentrations of the oligosaccharide fractions

| | | Example 2.1 "Hexa" | Example 2.2 "Octa" | Example 2.3 "Deca" |
|---|---|---|---|---|
| concentration | mg/ml | 4.0 | 6.2 | 3.6 |

Example 3: Determination of Anti-FXa Activity of Heparin Fragment Fractions in Solution Anti-FXa activity was determined by Evaluation Method C on example 1.2 (alpha), 1.1 (beta), 2.1, 2.2 and 2.3 (see Table 3). All heparin fragments tested were in solution and not immobilized to a surface.

TABLE 3

Anti-FXa activity of the heparin fragments. As a comparison, the anti-FXa activity for heparin API (Heparin Sodium Active Pharmaceutical Ingredient) is ~200 IU/mg (according to pharmacopoeias (USP, Ph. Eur.)).

| Example | anti-FXa activity IU/mg |
|---|---|
| 2.1 ("Hexa") | 5 |
| 2.2 ("Octa") | 12 |
| 2.3 ("Deca") | 20 |
| 1.2 (synthetic penta with α-linker) | 330 |
| 1.1 (synthetic penta with β-linker) | 385 |

As expected, depolymerization of heparin (with anti-FXa activity approximately 200 IU/mg) into oligosaccharides substantially reduced the anti-FXa activity. Since an octasaccharide is the smallest fragment derived from heparin by nitrous acid that can contain a functional active sequence (Thunberg L. et al, FEBS Letters 117 (1980), 203-206), the anti-FXa activity of the hexasaccharide fraction presumably comes from the presence of some larger fragments (octasaccharides) in that fraction. The synthesized pentasaccharide compounds had higher anti-FXa activities than native heparin. This is expected due to the high proportion of active sequence present in these compounds.

Example 4: Anti-FXa Activity; Effect of Example 2.2 (Octasaccharide Fraction) in Solution The anti-FXa activity of an octasaccharide fraction (Example 2.2) was analyzed according to Evaluation Method D. After 0, 5, 10, 20 and 30 min, samples (2×250 µl) from each mixture were transferred to test tubes on ice. An incubation mixture without addition of the octasaccharide fraction was used as control. The results are presented in Table 4 below; showing that the octasaccharide has the ability to inhibit FXa in solution.

Example 5: Anti-FIIa Activity; Effect of Example 2.2 (Octasaccharide Fraction) in Solution The anti-FIIa activity of the octasaccharide fraction (Example 2.2) was analyzed according to Evaluation Method E.

An incubation mixture without addition of the octasaccharide fraction was used as control. After 0, 5, 10, 20 and 30 min, duplicate samples (250 µl) from each mixture were transferred to test tubes on ice. At the end of the incubation period the residual FIIa activity was measured by adding the FIIa-substrate (final concentration 0.25 mM). The enzymatic activity declined at equal rate in the presence and absence of the octasaccharide fraction, showing that the octasaccharide at the concentration tested had no catalytic effect on the AT-mediated inhibition of FIIa, see Table 4 below.

TABLE 4

Effect of example 2.2 (octasaccharide) in solution on the inhibition of FXa and of FIIa in the presence of AT. The control is an incubation mixture without octasaccharide.

| Time | Residual FXa activity (mOD/min) | | Residual FIIa activity (mOD/min) | |
| --- | --- | --- | --- | --- |
| (min) | 2.2 | Control | 2.2 | Control |
| 0* | 262 | 268 | 273 | 265 |
| 0** | 4 | 229 | ND | ND |
| 5 | 5 | 188 | 224 | 219 |
| 10 | 3 | 162 | 208 | 189 |
| 20 | 3 | 118 | 167 | 145 |
| 30 | 2 | 88 | 170 | 142 |

ND = Not determined.
*Analyzed immediately before addition of octasaccharide,
**Analyzed immediately after addition of octasaccharide Accordingly, it may be noted that that the octasaccharide fraction, when in solution, does not display an appreciable catalytic effect on the AT-mediated inhibition of FIIa.

Example 6: Immobilization of Heparin Fragments to a Layer by Layer Coating on a Surface General Coating Process The luminal surface of a section of PVC tubing was coated with a layer-by-layer coating of cationic polymer and anionic polymer using essentially the method described by Larm et al. in EP0086186A1, EP0495820B1 and EP0086187A1 (all incorporated herein by reference in their entirety). Specifically, the luminal surface of the tubing was firstly cleaned with isopropanol and an oxidizing agent. The coating bilayers were built-up by alternating adsorption of a cationic polymer (polyamine, 0.05 g/L in water) and an anionic polymer (dextran sulfate, 0.1 g/L in water). The polyamine was crosslinked with a difunctional aldehyde (crotonaldehyde).

The anionic polymer is a dextran sulfate which has a MW of 4000 kDa when measured according to Evaluation Method K and has a high charge density (6.2 µeq/g) when measured according to Evaluation Method L. The dextran sulfate was added in a solution of high salt concentration (NaCl, 1.7 M).

Example 6.1: Immobilization of Octasaccharide

PVC tubing (I.D. 3 mm) was coated according to the general procedure described above with sixteen ml of the "octa" fraction (example 2.2) diluted with 84 ml of 0.05 M NaCl, the octa fraction was then immobilized to the outermost layer of polyamine via reductive amination, essentially as described by Larm et al in EP0086186A1 and EP0495820B1.

Example 6.2: Immobilization of Heparin (Positive Control)

PVC tubing (I.D. 3 mm) was coated according to the general procedure described above with heparin prepared as described in EP0086186 and U.S. Pat. No. 6,461,665. The heparin has a disperse molecular weight distribution where the average heparin chain length is more than 18 sugar units and therefore has the ability to inhibit both FXa and FIIa in solution. The heparin was bound to the outermost layer of polyamine on the PVC tubing via reductive amination, as performed above for Example 6.1.

Example 6.3: Immobilization of a Synthetic Pentasaccharide with a Linker, Example 1.1

Example 1.1 is reacted with a commercially available N-Hydroxysuccinimide Ester of 6,6-Dimethoxyhexanoic Acid and thereafter deprotected according to the procedure described in Pozsgay *J. Org. Chem.*, 63(17), 1998, 5983-5999. The aldehyde functionlized spacer can be bound to a surface according to the general procedure described above, see FIG. 6.

Example 7: Immobilization of Heparin Fragments to an Alternative Layer-by-Layer Coating on a Surface General Coating Process The process followed was essentially as described in Example 6. In this case the cationic polymer used was Epomin P-1050 (Nippon Shokubai, 70 kDa) and that the anionic polymer used was a dextran sulfate (Tdb Consultancy) with low charge density (3 µeq/g) when measured with Evaluation Method L. The dextran sulfate was applied with a salt concentration of either 0.25 or 0.5 M.

Example 7.1: Immobilization of Octasaccharide

PVC tubing (I.D. 3 mm) was coated according to the general procedure described above where the dextran sulfate was applied at a NaCl concentration of 0.25 M. The octasaccharide fraction (Example 2.2) was then immobilized to the outermost layer of polyamine via reductive amination, as described in Example 6.1.

Example 7.2: Immobilization of Octasaccharide Using a Higher Salt Concentration PVC tubing (I.D. 3 mm) was coated according to the general procedure described above in Example 7.1, where the dextran sulfate was applied at a NaCl concentration of 0.50 M.

Figure 8:
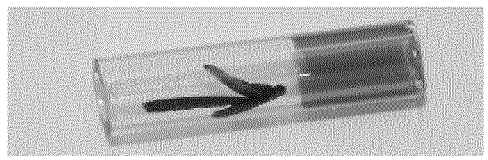
FIG. 8: Toluidine blue staining of coated PVC

Example 8: Evaluation by Toluidine Staining of PVC Tubing Coated with Heparin Fragments PVC tubing coated according to Example 6.1, 7.1 and 7.2 were subjected to a toluidine blue staining test as set out in Evaluation Method I. An intense blue/violet color was observed on the luminal surface of the tubing indicating an extensive covalent attachment of the heparin fragments. The homogenous staining obtained for tested tubing indicates formation of a uniform coating, see FIG. 8.

Example 9: Evaluation of Heparin Density of PVC Tubing Coated with Heparin Fragments The heparin densities of Examples 6.1, 6.2, 7.1 and 7.2 were determined by Evaluation Method H and the results are shown in Table 5 below.

Example 10: Evaluation of Heparin Activity of PVC Tubing Coated with Heparin Fragments The heparin activity of the octasaccharide coated surfaces described in Example 6.1, 7.1 and 7.2 was determined by Evaluation Method J; a heparin coated PVC tubing (Example 6.2) was utilized as positive control. The heparin activity (pmol AT/cm$^2$) of Example 6.2 was taken to be 100% activity and the activity of the other coated surfaces were expressed relative to this. The results are shown in Table 5 below.

TABLE 5

Evaluation of the octasaccharide coated surfaces as described in Examples 6 and 7.

| Example | Heparin density (μg/cm$^2$) | Heparin activity (%) |
|---|---|---|
| 6.1 | 5.6 | 7 |
| 6.2 | 6.3 | 100 |
| 7.1 | 5.1 | 0.2 |
| 7.2 | 5.6 | 0.7 |

Although the heparin density values of the octasaccharide coatings (Example 6.1, 7.1 and 7.2) and the heparin coating (Example 6.2) were similar, the AT binding capacity (heparin activity; 'HA') of the octasaccharide coatings was low compared to the heparin coating. However, this is to be expected considering the relatively low anti-FXa activity exhibited by the octasaccharide fraction in solution (Example 2.2 in Table 3). Thus, the octasaccharide fragments appear to substantially retain their AT-binding capacity after immobilization.

Example 11: Evaluation of Anti-FXa Activity of PVC Tubing Coated with Heparin Fragments The anti-FXa activity of PVC tubing coated according to Example 6.1 was evaluated according to Evaluation Method F, using Example 6.2 as positive control. The results are shown in Table 6 below.

TABLE 6

Inhibition of FXa in loops of octasaccharide-coated and uncoated tubing, plus a test tube control. The coated surfaces catalyzed rapid inhibition of FXa in contrast to the uncoated PVC and test tube controls

| Example | Residual FXa activity (mOD/min) | Inhibition of FXa activity (%) |
|---|---|---|
| Test tube control | 182 | N/A |
| Negative control uncoated PVC | 178 | 0 |
| Immobilized octasaccharide (6.1) | 22 | 87 |

It can be seen from Table 6 that the various examples performed as expected. The octasaccharide coated surface was effective in catalysing inhibition of FXa—this property is therefore maintained regardless of whether the octasaccharide is immobilised or in solution (see Example 5, Table 4). The uncoated plain PVC loop control and the test tube control were ineffective in catalysing inhibition of FXa.

Also as expected, the heparin coated positive control (Example 6.2), having an average heparin chain length of substantially more than 18 sugar units, was capable of effectively inhibiting FXa when immobilized (residual FXa activity 1.4 mOD/min, inhibition of FXa activity 99%).

Example 12: Evaluation of Anti-FIIa Activity of PVC Tubing Coated with Heparin Fragments Loops of PVC tubing coated according to Example 6.1, 6.2, 7.1 and 7.2 were evaluated according to Evaluation Method G. As a positive control the same reaction mixture was incubated in PVC tubing coated with heparin (Example 6.2, where the average heparin chain length is substantially longer than 18 sugar units and therefore this coating is expected to inhibit both FXa and FIIa in solution). The results are shown in Table 7.

TABLE 7

Inhibition of FIIa in loops of octasaccharide-coated and uncoated tubing, plus a test tube control. Results are normalized to uncoated PVC tubing

| Example | Residual FIIa activity (mOD/min) | Inhibition of FIIa activity (%) |
|---|---|---|
| 6.1 | 9.2 | 96 |
| 7.1 | 47 | 80 |
| 7.2 | 46 | 80 |
| Uncoated PVC tubing | 230 | 0 |
| Test tube | 300 | N/A |

The results show that these fragments of heparin, devoid of the capacity to catalyse the inhibition of FIIa by AT in solution, are surprisingly capable of catalysing this same reaction when they are immobilized to a surface. The immobilized fragments are organized in a way which may allow them to act synergistically, to accomplish that which requires substantially longer molecules in solution.

The effect could be seen with all octasaccharide coated examples (6.1, 7.1, 7.2), although the coating used in Example 6.1 shows higher inhibition compared to Example 7.1 and 7.2.

As expected, the heparin coated positive control (Example 6.2), having an average heparin chain length of substantially more than 18 sugar units, was capable of effectively inhibiting FIIa when immobilized (residual FIIa activity 1.4 mOD/min, inhibition of FIIa activity 99%).

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. An anticoagulant surface which surface has covalently bound thereto a plurality of fragments of heparin, wherein said fragments consist of 5-18 saccharide units and at least some of said plurality of fragments comprise polysaccharide sequence A:

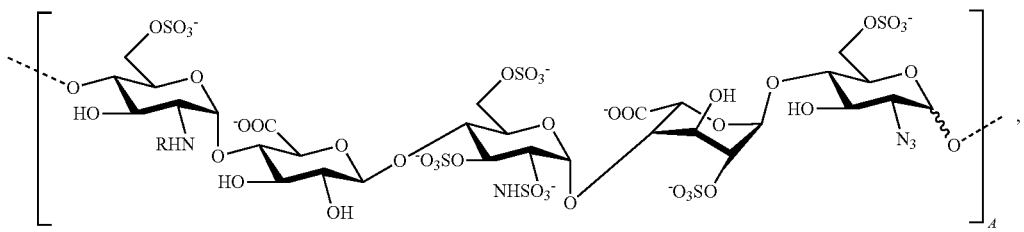

wherein R=Ac or SO$_3$-
which surface catalyses the inhibition of FIIa and FXa by AT, and wherein the surface has a heparin fragment concentration of at least 1 μg/cm2.

2. A surface according to claim 1 wherein the surface inhibits FIIa activity by at least 50% when measured according to Evaluation Method G.

3. A surface according to claim 1 wherein the surface inhibits FXa activity by at least 50% when measured according to Evaluation Method F.

4. A surface according to claim 1 wherein the fragments of heparin are heterogeneous in structure.

5. A surface according to claim 1 wherein said fragments of heparin are homogeneous in structure and all comprise polysaccharide sequence A.

6. A surface according to claim 1 wherein said fragments of heparin are fragments of native heparin produced by a process comprising degrading native heparin.

7. A surface according to claim 1 wherein said fragments of heparin are synthetically produced.

8. A surface according to claim 1 wherein the fragments of heparin are covalently bound to the surface via a linker.

9. A surface according to claim 8 wherein the linker comprises a thioether or a 1,2,3-triazole.

10. A surface according to claim 8 wherein a spacer is positioned between the linker and the surface.

11. A surface according to claim 1 wherein the fragments of heparin are single-point attached.

12. A surface according to claim 11 wherein the fragments of heparin are end-point attached.

13. A surface according to claim 12 wherein the fragments of heparin are covalently bound to the surface via their reducing end.

14. A surface according to claim 13 wherein the fragments of heparin are covalently bound to the surface via position C1 of their reducing end.

15. A surface according to claim 13 wherein the surface comprises amine groups which are reacted with the reducing end of the heparin fragments.

16. A surface according to claim 1 which has heparin activity of at least 1 pmol/cm$^2$ of surface, at least 2 pmol/cm$^2$ of surface, at least 3 pmol/cm$^2$ of surface, at least 4 pmol/cm$^2$ of surface, or at least 5 pmol/cm$^2$ of surface for binding of AT, suitably measured according to Evaluation Method J.

17. A surface according to claim 1 which has a heparin concentration of at least 2 μg/cm$^2$, at least 4 μg/cm$^2$, at least 5 μg/cm$^2$, or at least 6 μg/cm$^2$, suitably measured according Evaluation Method H.

18. A surface according to claim 1 wherein said fragments of heparin consist of at least 6 saccharide units.

19. A surface according to claim 1 wherein said fragments of heparin consist of no more than 16 saccharide units.

20. A surface according to claim 19 wherein said fragments of heparin consist of no more than 14 saccharide units.

21. A surface according to claim 20 wherein said fragments of heparin consist of no more than 10 saccharide units.

22. A surface according to claim 1 wherein said fragments of heparin consist of 5 saccharide units.

23. A surface according to claim 1 wherein said fragments of heparin are not covalently bound to the surface via a linker comprising a thioether nor a linker comprising a 1,2,3-triazole.

24. A surface according to claim 23 wherein the fragments of heparin are not covalently bound to the surface via any linker.

25. A surface according to claim 1 wherein the fragments of heparin are covalently bound to the surface via a linker and the linker comprises formula (I)

$$(CH_2)_n NHCO(CH_2)_m \qquad (I)$$

wherein n is 1 to 20 and m is 1 to 20.

26. A surface according to claim 25 wherein n is 5 and m is 4.

27. A solid object comprising a surface according to claim 1.

28. A solid object according to claim 27 wherein the surface comprises a layer by layer coating, the outer coating layer being a cationic polymer to which the fragments of heparin are covalently bound.

29. A solid object according to claim 28 wherein the layer by layer coating is an alternating layer of cationic and anionic polymers.

30. A solid object according to claim 28 wherein the cationic polymer layers are layers of cationic polymeric amines.

31. A solid object according to claim 29 wherein the anionic polymer layers are layers of dextran sulfate.

32. A solid object according to claim 27 which is a medical device.

* * * * *